United States Patent
Zhang et al.

(10) Patent No.: US 10,065,962 B2
(45) Date of Patent: Sep. 4, 2018

(54) AMINO PRYAN RING DERIVATIVE AND COMPOSITION AND USE THEREOF

(71) Applicant: Sichuan Haisco Pharmaceutical Co., Ltd., Sichuan Province (CN)

(72) Inventors: Chen Zhang, Sichuan Province (CN); Jianmin Wang, Sichuan Province (CN); Caihu Li, Sichuan Province (CN); Yonggang Wei, Sichuan Province (CN)

(73) Assignee: SICHUAN HAISCO PHARMACEUTICAL CO., LTD, Sichuan Providence (CN)

( * ) Notice: Subject to any disclaimer, the term of this patent is extended or adjusted under 35 U.S.C. 154(b) by 0 days.

(21) Appl. No.: 15/319,591

(22) PCT Filed: May 14, 2015

(86) PCT No.: PCT/CN2015/078923
§ 371 (c)(1),
(2) Date: Dec. 16, 2016

(87) PCT Pub. No.: WO2015/192701
PCT Pub. Date: Dec. 23, 2015

(65) Prior Publication Data
US 2017/0121338 A1  May 4, 2017

(30) Foreign Application Priority Data
Jun. 17, 2014 (CN) .......................... 2014 1 0269691

(51) Int. Cl.
C07D 487/04 (2006.01)
A61K 31/4162 (2006.01)
A61K 9/00 (2006.01)

(52) U.S. Cl.
CPC .......... *C07D 487/04* (2013.01); *A61K 9/0053* (2013.01); *A61K 31/4162* (2013.01)

(58) Field of Classification Search
None
See application file for complete search history.

(56) References Cited

U.S. PATENT DOCUMENTS 8,143,289 B2 * 3/2012 Biftu .................... C07D 487/04
514/338

FOREIGN PATENT DOCUMENTS

| WO | 2007126745 A3 | 11/2007 |
|---|---|---|
| WO | 2008060488 A1 | 5/2008 |
| WO | 2009025784 A1 | 2/2009 |
| WO | 2010056708 A1 | 5/2010 |
| WO | 2011028455 A1 | 3/2011 |
| WO | 2011037793 A1 | 3/2011 |
| WO | 2011103256 A1 | 8/2011 |
| WO | 2014018350 A1 | 1/2014 |

OTHER PUBLICATIONS

Patani et al. (Chemical Reviews, 1996, vol. 96, 3147-3176).*
Chinese Office Action dated Sep. 11, 2017 for Chinese patent application No. 201580001776.8.
Extended European Search Report dated Sep. 26, 2017 for European patent application No. 15809919.2.
Office Action dated May 5, 2017 for Chinese patent application No. 201580001776.8.
Office Action and Search Report dated Feb. 2, 2018 for Taiwan patent application No. 104128089.
Patani et al; "Bioisosterism: A Rational Approach in Drug Design"; Chem. Rev. 1996, 96; 3147-3176.

* cited by examiner

*Primary Examiner* — Kamal Saeed
(74) *Attorney, Agent, or Firm* — Ohlandt, Greeley, Ruggiero & Perle, LLP

(57) ABSTRACT

The present disclosure relates to an amino pyran ring derivative and a composition and use thereof, and in particular, to an amino pyran ring derivative represented by general formula (I) or a stereoisomer, a pharmaceutically acceptable salt or a prodrug thereof, a pharmaceutical composition comprising the derivative, and their medical use in the manufacture of a di-peptidyl peptidase IV (DPP-IV) inhibitor,

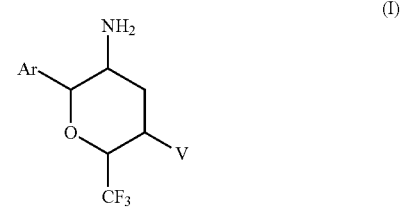

in formula (I) the substituents are defined the same as those in the specification.

18 Claims, 13 Drawing Sheets

AMINO PRYAN RING DERIVATIVE AND COMPOSITION AND USE THEREOF

TECHNICAL FIELD

The present invention relates to an amino pyran ring derivative and a composition and use thereof, and in particular, to an amino pyran ring derivative represented by general formula (I) or a pharmaceutically acceptable salt or stereoisomer thereof, a pharmaceutical composition comprising the derivative or a pharmaceutically acceptable salt or stereoisomer thereof, and their use as a therapeutic agent, particularly as a di-peptidyl peptidase IV (DPP-IV) inhibitor.

BACKGROUND ART

Diabetes mellitus (DM) has become a serious medical and healthcare issue worldwide. According to the statistics provided by the international Diabetes Federation (IDF), the population of the diabetes patients in the world reached 382 million in 2013, incurring a global medical cost of $548.0 billion, which represents 11% of the total medical expense all over the world. The global medical expense associated with diabetes is expected to reach $627.3 billion in 2035. Insulin is a hormone required for the transformation of sucrose, starch and other food into enemy, and the body's inability to secrete or properly utilize insulin is generally the cause of diabetes. Diabetes is in general classified into type I diabetes (also called insulin-dependent diabetes mellitus, IDDM) and type II diabetes (also called non-insulin-dependent diabetes mellitus NIDDM). Type II diabetes is the most common type and represents around 90% of all diabetes worldwide. The incidence of type II diabetes shows a tendency to keep increasing, because of unhealthy life style in modern society, such as reduced physical exercise and high-calorie diet. The huge market potential has promoted many pharmaceutical companies and research institutes to develop new anti-diabetes targets and medicines.

Currently approved and marketed medicines for type II diabetes mainly include insulin and its analogs, sulfonylureas, biguanides, thiazolinediones (TZDs), α-glucosidase inhibitors, dextrin analogues, incretin analogs, di-peptidyl peptidase IV (DPP-IV) inhibitors, and the like. However, patients taking these hypoglycemic drugs for a long term still fail to have a desired reduction in glycated hemoglobin (HbA1c), and suffer side effects from these drugs, such as hypoglycemia, body weight gain, and cardiovascular risks, which increase the burden on diabetes patients. Hence, there is an urgent demand for a new hypoglycemic drug against type II diabetes that has high efficacy and fewer side effects.

Di-peptidyl peptidase IV (DPP-IV, EC3.4.14.5) is a serine protease which hydrolytically cleaves an N-terminal dipeptide at the last $2^{nd}$ position from the N-terminus of an L-proline- or L-alanine-containing polypeptide. Although functions of DPP-IV have not been fully elucidated, it is believed to be a major physiological modulating factor for certain modulatory polypeptides, neuropeptides, circulating hormones, and chemotactic factors. Although DDP-IV is a multi-specific enzyme and has a diverse range of substrates, the most common substrates thereof are incretins that include glucagon like peptide-1 (GLP-1) and glucose-dependent insulinotropic polypeptide (GIP). Incretins are intestine hormones secreted within a few minutes after intake of nutrients and promoting the processing of the taken nutrients. GLP-1 and GIP show the same effects on β-cells and may improve β-cell functioning, including promoting glucose-dependent insulin secretion, inducing β-cell proliferation and enhancing anti-apoptosis function (Diabetes and Vascular Disease Research 2006 3:159).

Unlike GIP, GLP-1 still promotes insulin secretion in type II diabetes. Therefore, increasing GLP-1 is a promising therapeutic means against type II diabetes (Pharmacol Rev 60:470-512, 2008). GLP-1 may considerably lower the blood sugar level in type II diabetes patients (Lancet, 2002, 359:824-830), but will be rapidly hydrolyzed and inactivated in vivo as a substrate of DPP-IV. Hence, development of DPP-IV inhibitors has great significance for diabetes therapies.

Until now studies on DPP-IV inhibitors have made tremendous advances, and DPP-IV inhibitors including Sitagliptin, Saxagliptin and Alogliptin have been approved and used in clinical settings. DPP-IV inhibitors are highly characteristic in that, since incretins are secreted only after food intake in bodies, DPP-IV inhibitors do not tend to inappropriately increase the insulin level and lead to hypoglycemia, a side effect common to many hypoglycemic drugs. Recent clinical data show that inhibition of DPP-IV may increase insulin secretion, lower blood sugar concentration, and improve functions of β-cells of pancreatic islets (Diabetes, 1998, 47:1253-1258). Typical side effects of DPP-IV inhibitors include respiratory infection, throat pain, diarrhea, common cold-like symptoms, headache, dizziness, and the like. However, in general, DPP-IV inhibitors have good safety and tolerance, and till now patients taking DPP-IV inhibitors have not been found to have severe body weight gain or potential symptoms like body weight loss and edema. In recent years, long-acting DPP-IV inhibitors have drawn particular interest, as they are easy to use and have an ideal hypoglycemic effect, making them more acceptable by type II diabetes patients. A phase-II clinical trial shows that a qw DPP-IV inhibitor Omarigliptin developed by Merck can remarkably lower the blood sugar level. Another qw DPP-IV inhibitor Trelagliptin developed by Takeda Pharmaceutical Co. Ltd. has met the safety and efficacy requirements in the phase-III clinical trial, for which a new drug application has been filed in Japan.

Diabetes (mainly type II diabetes) has its global incidence increasing year by year, and has become the $3^{rd}$ most threatening non-infectious disease to human health and life following cardiovascular diseases and cancer. Treatment of diabetes has laid down an enormous burden upon families and the society. Therefore, there is a great need for more new and better DPP-IV inhibitors to meet the demand of patients for clinically useful medicines.

Until now several studies on DPP-IV inhibitors have been reported:

(1) US 2007232676 discloses compounds having the following structure, as a DPP-IV inhibitor:

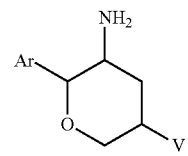

wherein Ar may be a phenyl group substituted with 1 to 5 substituents selected from halogen, hydroxyl, a $C_{1-6}$ alkyl, and the like; V is selected from groups like

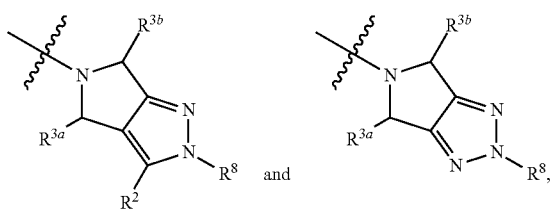

where $R^{3a}$ and $R^{3b}$ are independently selected from hydrogen and a $C_{1-4}$ alkyl substituted with 1 to 5 fluorine atoms; $R^2$ is selected from groups like hydrogen, hydroxyl, halogen, and carboxyl; $R^8$ is selected from groups like hydrogen and —$(CH_2)_p$-phenyl but excludes methylsulfonyl. The detailed descriptions in this patent document are not considered as part of the present invention.

(2) US 20100120863 discloses use of compounds having the following structure as a DPP-IV inhibitor for the treatment or prevention of type II diabetes:

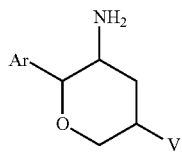

wherein Ar is a phenyl group substituted with hydrogen, alkyl or the like; V is selected from groups like

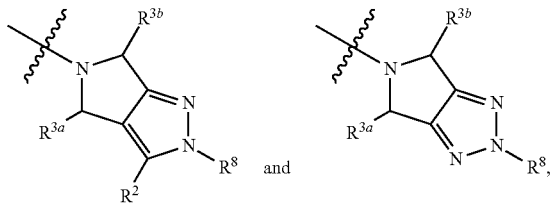

where $R^{3a}$ and $R^{3b}$ are independently selected from hydrogen and a $C_{1-4}$ alkyl substituted with 1 to 5 fluorine atoms; $R^2$ is selected from groups like hydrogen, hydroxyl, halogen, and carboxyl; $R^8$ is selected from groups like —$SO_2$—$C_{1-6}$ cycloalkyl and —$SO_2$—$C_{1-6}$ alkyl. The detailed descriptions in this patent document are not considered as part of the present invention.

(3) WO 2011103256 discloses that compounds having the following structure have a DPP-IV inhibitor function, for use as a drug for the treatment and/or prevention of diabetes:

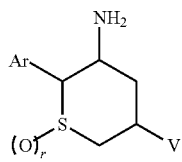

wherein Ar is a phenyl optionally substituted with 1 to 5 groups selected from halogen, cyano, hydroxyl, etc.; V is selected from groups like

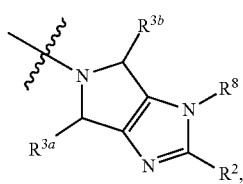

where $R^2$ is selected from groups like hydrogen, hydroxyl, cyano, halogen, alkyl, alkoxy, and carbonyl; $R^{3a}$ and $R^{3b}$ are selected from hydrogen and a $C_{1-4}$ alkyl optionally substituted with 1 to 5 fluorine atoms; $R^8$ is selected from groups like hydrogen, alkyl, aryl, cycloalkyl, heteroaryl, and —$SO_2$—$C_{1-6}$ alkyl. The detailed descriptions in this patent document are not considered as part of the present invention.

(4) WO2007126745 discloses compounds having the following structure as a DPP-IV inhibitor for the treatment of diabetes:

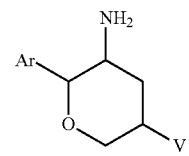

wherein Ar is a substituted or unsubstituted phenyl group, and when substituted, the phenyl is substituted with 1 to 3 substituents selected from halogen, hydroxyl, $C_{1-6}$ alkyl or the like; V is selected from groups like

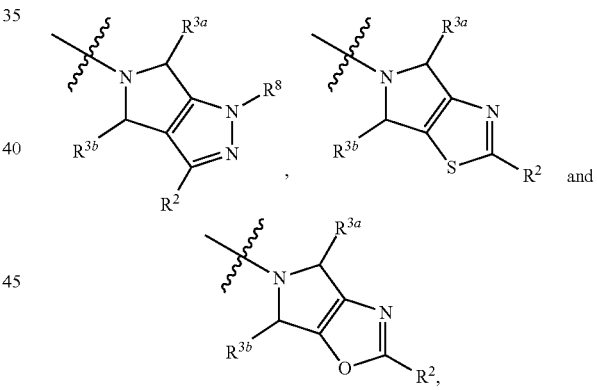

where $R^2$ is selected from groups like hydrogen, hydroxyl, halogen, alkenyl, alkynyl, aryl and heteroaryl; $R^{3a}$ and $R^{3b}$ are selected from hydrogen and a $C_{1-4}$ alkyl substituted with 1 to 5 fluorine atoms; $R^8$ is selected from groups like H, cycloalkyl, phenyl, and alkyl. The detailed descriptions in this patent document are not considered as part of the present invention.

In addition, WO2011103256, WO2008060488, WO2007087231, WO2011037793, WO2011028455, and WO2009025784 also disclose compounds as DPP-IV inhibitors for treatment of diabetes.

SUMMARY OF INVENTION

An object of the present invention is to provide a novel DPP-IV inhibitors, specifically, compounds represented by general formula (I), which are shown in research to have good inhibitory activity and selectivity on DPP-IV and thus have a prospect of being used for treating or alleviating type II diabetes or similar diseases.

The present invention relates to an amino pyran ring derivative represented by general formula (I) or a stereoisomer, a pharmaceutically acceptable salt or a prodrug thereof:

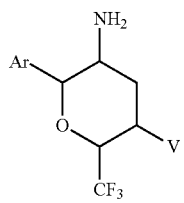

wherein
V is selected from the following groups:

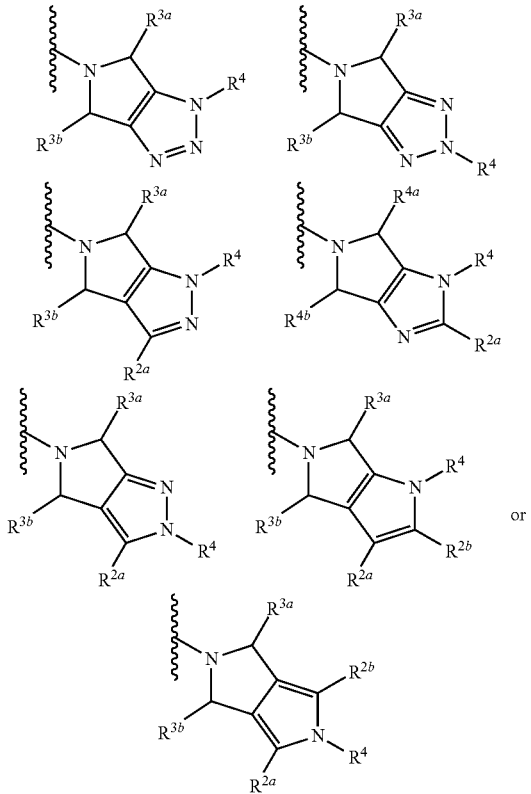

Ar is a phenyl substituted with 0 to 5 preferably 2,5-difluorophenyl or 2,4,5-trifluorophenyl;

$R^1$ is selected from H, F, Cl, Br, I, hydroxyl, cyano, $C_{1-8}$ alkyl, $C_{1-8}$ alkoxy, $C_{2-8}$ alkenyl, $C_{2-8}$ alkynyl, —$(CH_2)_m$—$C_{3-15}$ cycloalkyl, —$(CH_2)_m$—(3- to 15-membered heterocycloalkyl), —$(CH_2)_m$—$C_{6-10}$ aryl, —$(CH_2)_m$—(6- to 10-membered heteroaryl), —$(CH_2)_m$—C(=O)—$R^5$, —$(CH_2)_m$—NR$^6$R$^7$, —$(CH_2)_m$—C(=O)—NR$^6$R$^7$, —$(CH_2)_m$—O—C(=O)—NR$^6$R$^7$, —$(CH_2)_m$—S(=O)$_n$—$R^8$, —$(CH_2)_m$—NR$^9$—S(=O)$_n$—$R^8$, —$(CH_2)_m$—NR$^9$—C(=O)—NR$^6$R$^7$ or —$(CH_2)_m$—NR$^9$—C(=O)—$R^5$, wherein the alkyl, alkoxy, alkenyl, alkynyl, cycloalkyl, heterocycloalkyl, aryl or heteroaryl is optionally further substituted with 0 to 5 substituents selected from F, Cl, Br, I, —CH$_2$F, —CHF$_2$, —CF$_3$, hydroxyl, $C_{1-4}$ alkyl or $C_{1-4}$ alkoxy, the heterocycloalkyl or heteroaryl has 1 to 5 atoms or groups selected from N, O or S(=O)$_n$; $R^1$ is selected from H or F, $R^{2a}$ and $R^{2b}$ are each independently selected from H, F, Cl, Br, I, hydroxyl, cyano, $C_{1-8}$ alkyl, $C_{1-8}$ alkoxy, $C_{2-8}$ alkenyl, $C_{2-8}$ alkynyl, —$(CH_2)_m$—$C_{3-15}$ cycloalkyl, —$(CH_2)_m$—(3- to 15-membered heterocycloalkyl), —$(CH_2)_m$—$C_{6-10}$ aryl, —$(CH_2)_m$—(6- to 10-membered heteroaryl), —$(CH_2)_m$—C(=O)—$R^5$, —$(CH_2)_m$—NR$^6$R$^7$, —$(CH_2)_m$—C(=O)—NR$^6$R$^7$, —$(CH_2)_m$—O—C(=O)—NR$^6$R$^7$, —$(CH_2)_m$—S(=O)$_n$—$R^8$, —$(CH_2)_m$—NR$^9$—S(=O)$_n$—$R^8$, —$(CH_2)_m$—NR$^9$—C(=O)—NR$^6$R$^7$ or —$(CH_2)_m$—NR$^9$—C(=O)—$R^5$, wherein the alkyl, alkoxy, alkenyl, alkynyl, cycloalkyl, heterocycloalkyl, aryl or heteroaryl is optionally further substituted with 0 to 3 substituents selected from F, Cl, Br, I, —CH$_2$F, —CHF$_2$, —CF$_3$, hydroxyl, $C_{1-4}$ alkyl or $C_{1-4}$ alkoxy, and the heterocycloalkyl or heteroaryl has 1 to 5 atoms or groups selected from N, O or S(=O)$_n$; preferably, $R^{2a}$ and $R^{2b}$ are each independently selected from H, $C_{1-6}$ alkyl, —$(CH_2)_m$—$C_{3-6}$ cycloalkyl or —$(CH_2)_m$—(3- to 8-membered heterocycloalkyl), wherein the alkyl, cycloalkyl or heterocycloalkyl is optionally further substituted with 0 to 3 substituents selected from F, Cl, Br, I, —CH$_2$F, —CHF$_2$, —CF$_3$, hydroxyl, $C_{1-4}$ alkyl or $C_{1-4}$ alkoxy, and the heterocycloalkyl or heteroaryl has 1 to 3 atoms or groups selected from N, O or S(=O)$_n$; more preferably, $R^{2b}$ is selected from H, and $R^{2a}$ is selected from H, $C_{1-6}$ alkyl or —$(CH_2)_m$—$C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are each independently selected from H, F, Cl, Br, I, hydroxyl, cyano or $C_{1-8}$ alkyl, wherein the alkyl is optionally further substituted with 0 to 5 substituents selected from F, Cl, Br, I, —CH$_2$F, —CHF$_2$, —CF$_3$, hydroxyl, $C_{1-4}$ alkyl or $C_{1-4}$ alkoxy; $R^{3a}$ and $R^{3b}$ are preferably each independently selected from H or $C_{1-2}$ alkyl, wherein the alkyl is optionally further substituted with 0 to 3 substituents selected from F, hydroxyl or $C_{1-4}$ alkoxy; more preferably, $R^{3a}$ and $R^{3b}$ are each independently H;

$R^{4a}$ and $R^{4b}$ are each independently selected from H, F, Cl, Br, I, hydroxyl, cyano or $C_{1-8}$ alkyl, wherein the alkyl is optionally further substituted with 0 to 5 substituents selected from F, Cl, Br, I, —CH$_2$F, —CHF$_2$, —CF$_3$, hydroxyl, $C_{1-4}$ alkyl or $C_{1-4}$ alkoxy, and $R^{4a}$ and $R^{4b}$ are not at the same time H;

$R^4$ is selected from H, cyano, $C_{1-8}$ alkyl, $C_{1-8}$ alkoxy, $C_{2-8}$ alkenyl, $C_{2-8}$ alkynyl, —$(CH_2)_m$—$C_{3-15}$ cycloalkyl, —$(CH_2)_m$—(3- to 15-membered heterocycloalkyl), —$(CH_2)_m$—$C_{6-10}$ aryl, —$(CH_2)_m$-(6- to 10-membered heteroaryl), —$(CH_2)_m$—C(=O)—$R^5$, —$(CH_2)_m$—NR$^6$R$^7$, —$(CH_2)_m$—C(=O)—NR$^6$R$^7$, —$(CH_2)_m$—O—C(=O)—NR$^6$R$^7$, —$(CH_2)_m$—S(=O)$_n$—$R^8$, —$(CH_2)_m$—NR$^9$—S(=O)$_n$—$R^8$, —$(CH_2)_m$—NR$^9$—C(=O)—NR$^6$R$^7$ or —$(CH_2)_m$—NR$^9$—C(=O)—$R^5$, wherein the alkyl, alkoxy, alkenyl, alkynyl, cycloalkyl, heterocycloalkyl, aryl or heteroaryl is optionally further substituted with 0 to 3 substituents selected from F, Cl, Br, I, —CH$_2$F, —CHF$_2$, —CF$_3$, hydroxyl, $C_{1-4}$ alkyl or $C_{1-4}$ alkoxy, and the heterocycloalkyl or heteroaryl has 1 to 5 atoms or groups selected from N, O or S(=O)$_n$;

$R^4$ is preferably selected from H or —$(CH_2)_m$—S$(=O)_n$—$R^8$; more preferably, $R^4$ is S$(=O)_2$—$CH_3$;

$R^5$ is selected from hydroxyl, $C_{1-8}$ alkyl, $C_{1-8}$ alkoxy, $C_{3-15}$ cycloalkyl, $C_{6-10}$ aryl, 6- to 10-membered heteroaryl, —O—$C_{3-15}$ cycloalkyl, —O—$C_{6-10}$ aryl or —O-(6- to 10-membered heteroaryl); preferably $C_{1-8}$ alkyl or $C_{1-8}$ alkoxy, more preferably $C_{1-8}$ alkoxy;

$R^6$, $R^7$ and $R^9$ are each independently selected from H, $C_{1-8}$ alkyl, $C_{3-15}$ cycloalkyl, $C_{6-10}$ aryl, 6- to 10-membered heteroaryl or 3- to 15-membered heterocycloalkyl; preferably each independently selected from H or $C_{1-8}$ alkyl;

$R^8$ is selected from $C_{1-8}$ alkyl, $C_{3-15}$ cycloalkyl, $C_{6-10}$ aryl, 6- to 10-membered heteroaryl, or 3- to 15-membered heterocycloalkyl; preferably $C_{1-8}$ alkyl, $C_{3-15}$ cycloalkyl 3- to 15-membered heterocycloalkyl, more preferably $C_{1-8}$ alkyl; wherein the alkyl, cycloalkyl, heterocycloalkyl, aryl or heteroaryl is optionally further substituted with 0 to 5 fluorine atoms, and the heterocycloalkyl or heteroaryl has 1 to 5 atoms or groups selected from N, O or S$(=O)_n$;

m is selected from 0, 1 or 2, preferably 0 or 1, more preferably 0 and n is selected from 0, 1 or 2, preferably 0 or 2, more preferably 2.

In a preferred embodiment of the present invention, provided is an amino pyran ring derivative represented by general formula (I) or a stereoisomer, a pharmaceutically acceptable salt or a prodrug thereof, wherein $R^1$ is selected from H or F;

$R^{2a}$ and $R^{2b}$ are each independently selected from H, $C_{1-6}$ alkyl, $C_{3-6}$ cycloalkyl or 3 to 8-membered heterocycloalkyl, wherein the alkyl, cycloalkyl or heterocycloalkyl is optionally further substituted with 0 to 3 substituents selected from F, Cl, Br, I, —$CH_2F$, —$CHF_2$, —$CF_3$, hydroxyl, $C_{1-4}$ alkyl or $C_{1-4}$ alkoxy, and the heterocycloalkyl has 1 to 3 atoms or groups selected from N, O or S$(=O)_2$; preferably, $R^{2a}$ and $R^{2b}$ are each independently selected from H, $C_{1-6}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are preferably each independently selected from H or $C_{1-2}$ alkyl, wherein the alkyl is optionally further substituted with 0 to 3 substituents selected from F, hydroxyl or $C_{1-4}$ alkoxy; preferably, $R^{3a}$ and $R^{3b}$ are each independently H;

$R^4$ is selected from H or —S$(=O)_2$—$R^8$; preferably —S$(=O)_2$—$R^8$;

$R^8$ is selected from $C_{1-6}$ alkyl, $C_{3-6}$ cycloalkyl, $C_{6-10}$ aryl, 6 to 10-membered heteroaryl or 3 to 8-membered heterocycloalkyl; preferably $C_{1-2}$ alkyl, 4- to 6-membered heterocycloalkyl or $C_{3-6}$ cycloalkyl, more preferably $C_{1-2}$ alkyl; wherein the alkyl, cycloalkyl, heterocycloalkyl, aryl or heteroaryl is optionally further substituted with 0 to 5 fluorine atoms, and the heterocycloalkyl or heteroaryl has 1 to 5 atoms or groups selected from N, O or S$(=O)_2$.

In a preferred embodiment of the present invention, provided is an amino pyran ring derivative represented by general formula (I) or a stereoisomer, a pharmaceutically acceptable salt or a prodrug thereof, wherein V is selected from the following groups:

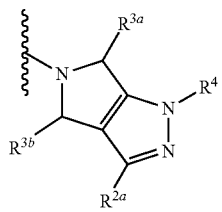 or 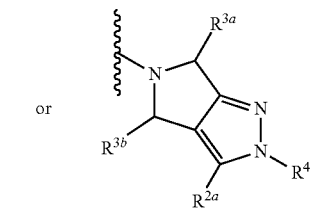

Ar is selected from 2,5-difluorophenyl or 2,4,5-trifluorophenyl $R^{2a}$ is selected from H, $C_{1-6}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy; preferably, $R^{2a}$ is selected from H, $C_{1-2}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are each independently selected from H or $C_{1-2}$ alkyl, wherein the alkyl is optionally further substituted with 0 to 3 substituents selected from F, hydroxyl or $C_{1-4}$ alkoxy; preferably, $R^{3a}$ and $R^{3b}$ are each independently H;

$R^4$ is —S$(=O)_2R^8$; preferably —S$(=O)_2$—$CH_3$;

$R^8$ is selected from $C_{1-2}$ alkyl, 3- to 6-membered heterocycloalkyl, or $C_{3-6}$ cycloalkyl; wherein the alkyl, heterocycloalkyl, or cycloalkyl is optionally further substituted with 0 to 5 fluorine atoms, and the heterocycloalkyl has 1 to 3 atoms or groups selected from N, O or S$(=O)_2$.

In a preferred embodiment of the present invention, provided is an amino pyran ring derivative represented by general formula (I) or a stereoisomer, a pharmaceutically acceptable salt or a prodrug thereof, wherein $R^{2a}$ is selected from H, $C_{1-2}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy; preferably, $R^{2a}$ is H or $C_{1-2}$ alkyl, wherein the alkyl is optionally further substituted with 0 to 3 substituents selected from F, hydroxyl, $C_{1-4}$ alkyl or $C_{1-4}$ alkoxy; more preferably, $R^{2a}$ is H or methyl.

In a preferred embodiment of the present invention, provided is an amino pyran ring derivative represented by general formula (I) or a stereoisomer, a pharmaceutically acceptable salt or a prodrug thereof, wherein V is selected from

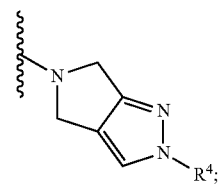

Ar is 2,5-difluorophenyl or 2,4,5-trifluorophenyl;

$R^{2a}$ is selected from H, $C_{1-6}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy; preferably, $R^{2a}$ is H, $C_{1-2}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are each independently selected from H or $C_{1-2}$ alkyl, wherein the alkyl is optionally further substituted with 0 to 3 substituents selected from F, hydroxyl or $C_{1-4}$ alkoxy; preferably, $R^{3a}$ and $R^{3b}$ are each independently H;

$R^4$ is —S(=O)$_2$—R$^8$; preferably —S(=O)$_2$—CH$_3$;

$R^8$ is selected from $C_{1-2}$ alkyl, 3- to 6-membered heterocycloalkyl, or $C_{3-6}$ cycloalkyl; wherein the alkyl, heterocycloalkyl, or cycloalkyl is optionally further substituted with 0 to 5 fluorine atoms, and the heterocycloalkyl has 1 to 3 atoms or groups selected from N, O or S(=O)$_2$.

In a preferred embodiment of the present invention, provided is an amino pyran ring derivative represented by general formula (I) or a stereoisomer, a pharmaceutically acceptable salt or a prodrug thereof, wherein V is selected from

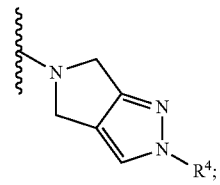

Ar is 2,5-difluorophenyl or 2,4,5-trifluorophenyl;

$R^{2a}$ is selected from H, $C_{1-6}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy; preferably, $R^{2a}$ is H, $C_{1-2}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are each independently selected from H or $C_{1-2}$ alkyl, wherein the alkyl is optionally further substituted with 0 to 3 substituents selected from F, hydroxyl or $C_{1-4}$ alkoxy; preferably; $R^{3a}$ and $R^{3b}$ are each independently H;

$R^4$ is —S(=O)$_2$—R$^8$;

$R^8$ is selected from $C_{1-2}$ alkyl, $C_{3-6}$ cycloalkyl, or 4- to 6-membered heterocycloalkyl; wherein the alkyl, cycloalkyl, or heterocycloalkyl is optionally further substituted with 0 to 5 fluorine atoms, the heterocycloalkyl has 1 to 3 atoms or groups selected from N, O or S(=O)$_2$.

In a preferred embodiment of the present invention, provided is an amino pyran ring derivative represented by general formula (I) or a stereoisomer, a pharmaceutically acceptable salt or a prodrug thereof, wherein $R^8$ is selected from methyl, ethyl,

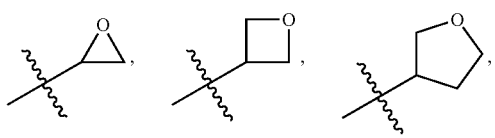

cyclopropyl, cyclobutyl, or cyclopentyl; preferably methyl; and these groups are optionally further substituted with 0 to 5 fluorine atoms.

In a preferred embodiment of the present invention, provided is an amino pyran ring derivative represented by general formula (I) or a stereoisomer, a pharmaceutically acceptable salt or a prodrug thereof, wherein $R^8$ is selected from methyl, ethyl,

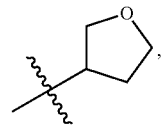

cyclopropyl, cyclobutyl, or cyclopentyl.

In a preferred embodiment of the present invention, provided is an amino pyran ring derivative represented by general formula (I) or a stereoisomer, a pharmaceutically acceptable salt or a prodrug thereof, wherein V is selected from

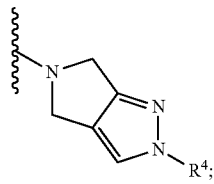

Ar is 2,5-difluorophenyl or 2,4,5-trifluorophenyl;

$R^{2a}$ is selected from H, $C_{1-6}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy; preferably, $R^{2a}$ is H, $C_{1-2}$ alkyl, or $C_{3-6}$ cycloalkyl, wherein the alkyl or cycloalkyl is optionally further substituted with 0 to 3 substituents selected from F, hydroxyl, $C_{1-4}$ alkyl or $C_{1-4}$ alkoxy;

$R^{3a}$ and $R^{3b}$ are each independently selected from H or $C_{1-2}$ alkyl, wherein the alkyl is optionally further substituted with 0 to 3 substituents selected from F, hydroxyl or $C_{1-4}$ alkoxy; preferably; $R^{3a}$ and $R^{3b}$ are each independently H;

$R^4$ is —S(=O)$_2$—R$^8$;

$R^8$ is selected from methyl, ethyl,

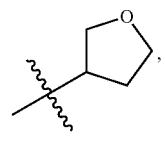

cyclopropyl, cyclobutyl, or cyclopentyl.

In a preferred embodiment of the present invention, provided is an amino pyran ring derivative represented by general formula (I) or a stereoisomer, a pharmaceutically acceptable salt or a prodrug thereof, wherein the amino pyran ring derivative is selected from:
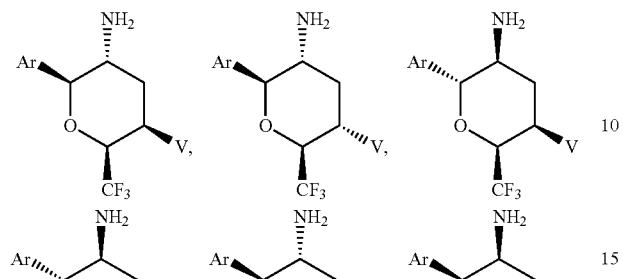
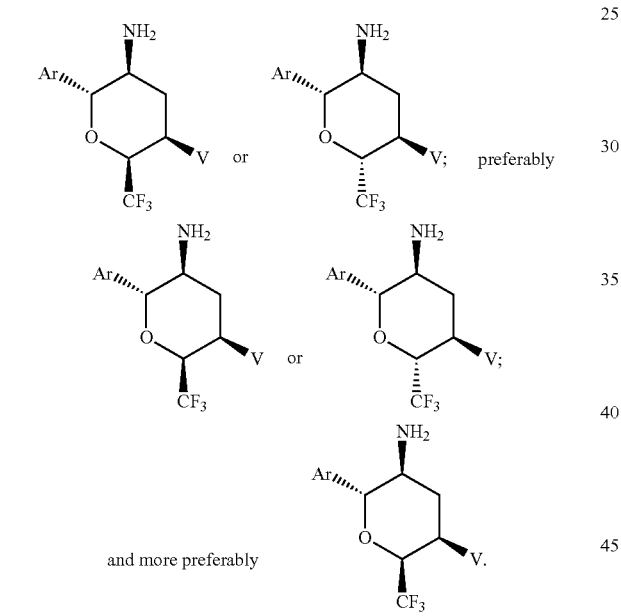
and more preferably
In a preferred embodiment of the present invention, the compound of the present invention is selected from, but not limited to:
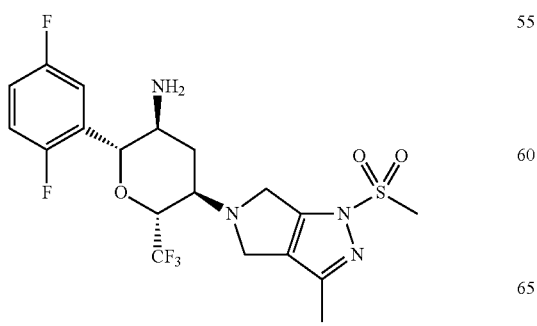
-continued
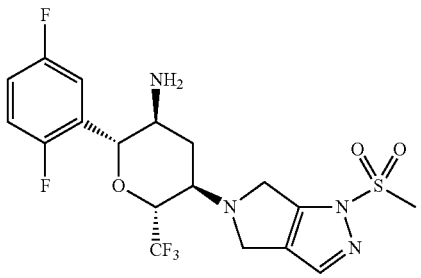
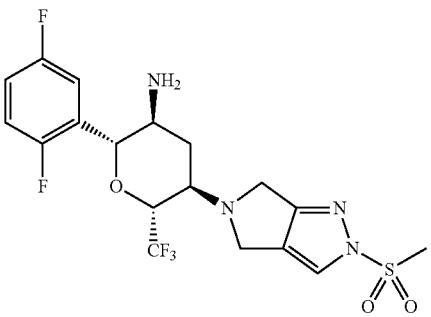
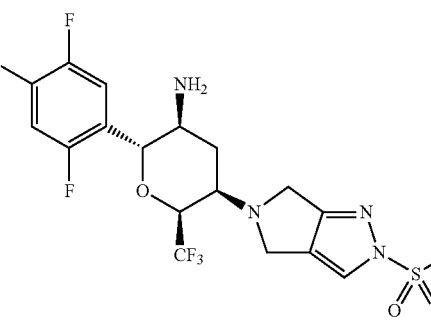
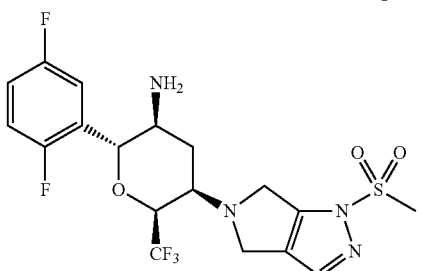

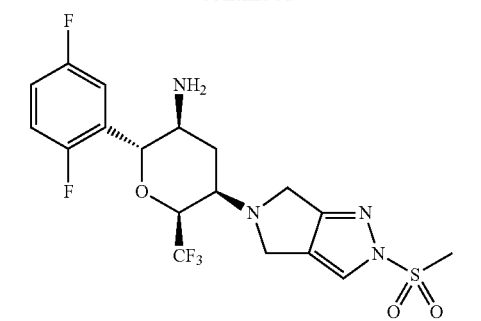
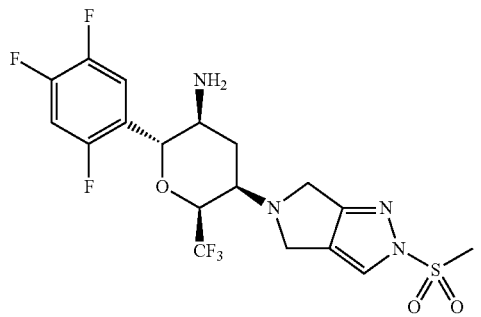
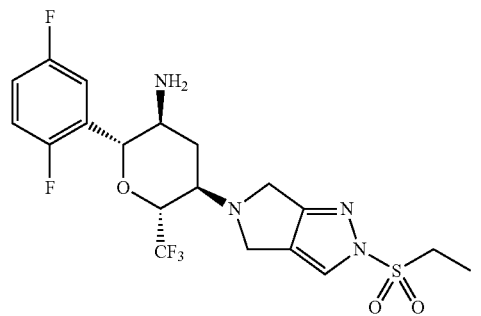
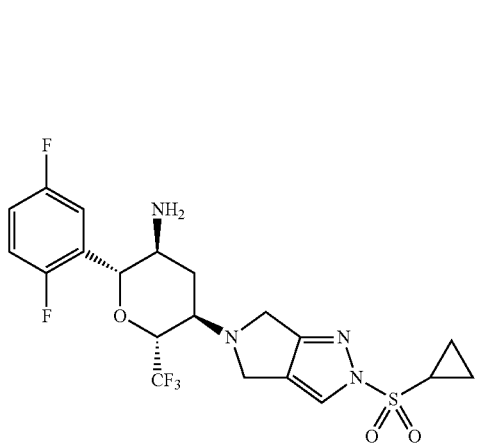
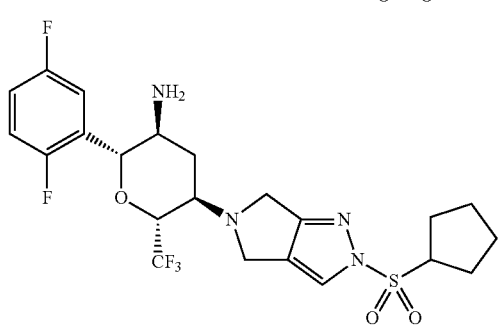
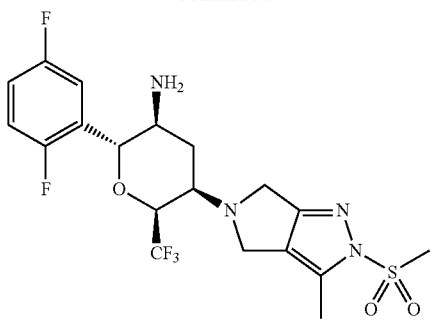
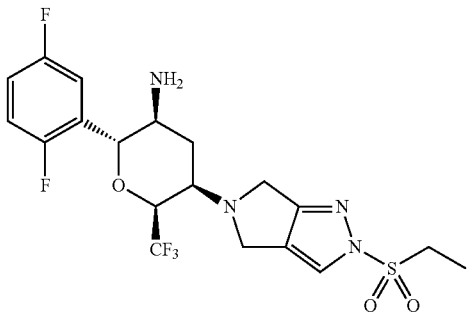
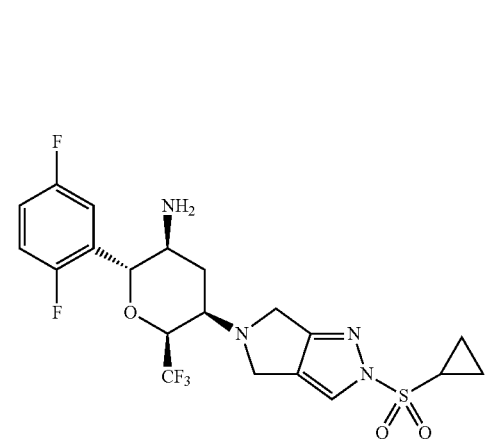
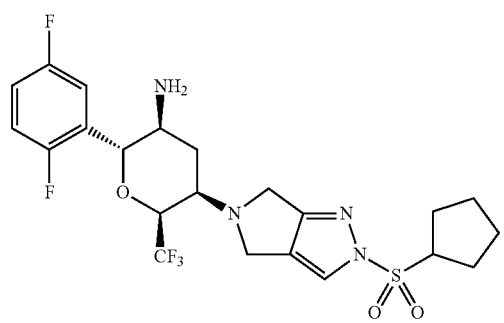
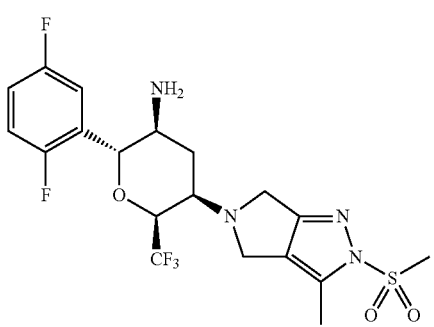

15
-continued

16
-continued

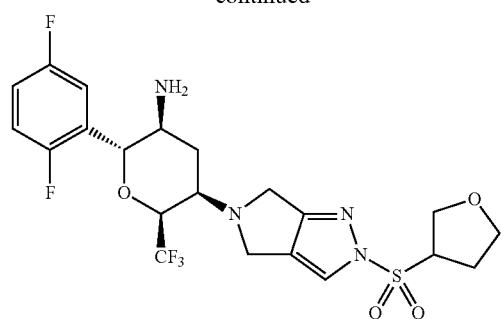
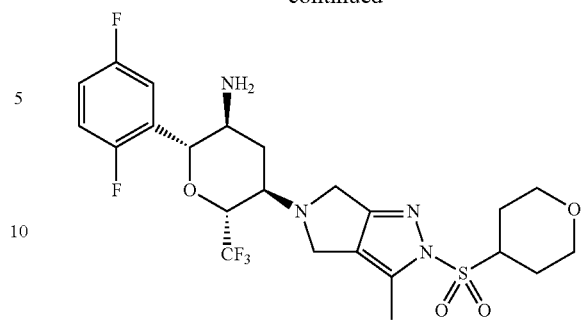
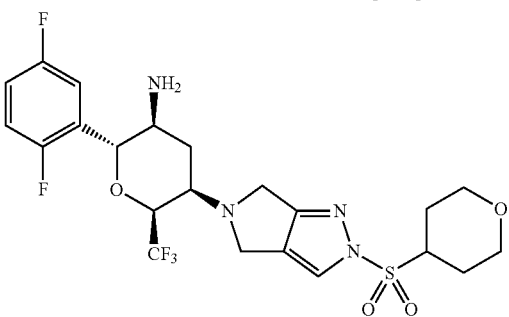
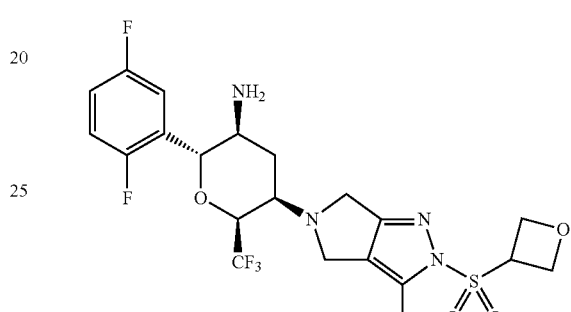
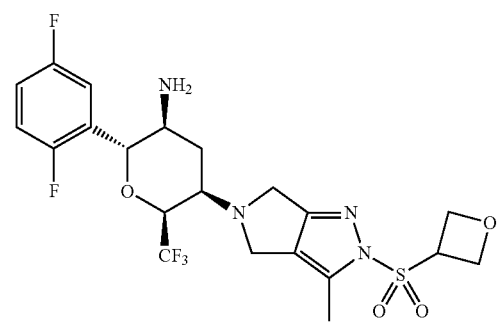
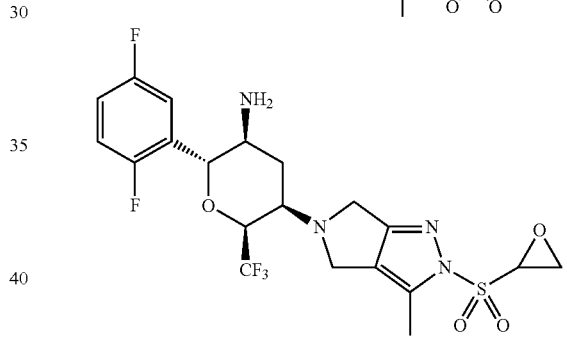
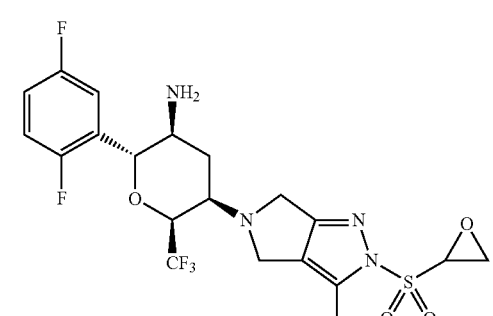
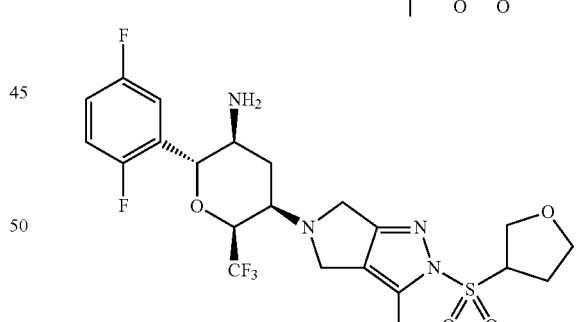
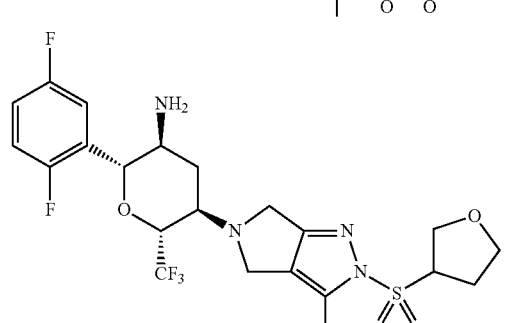
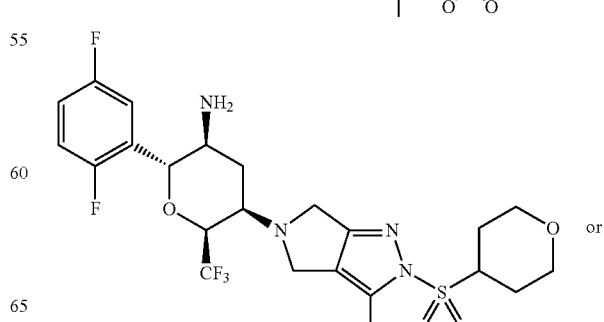
or -continued
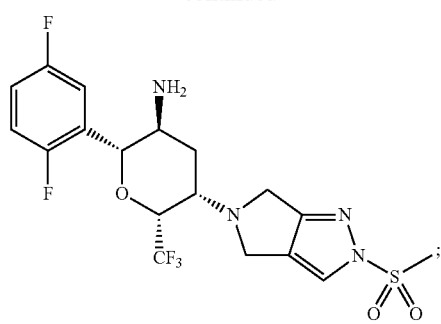
preferably
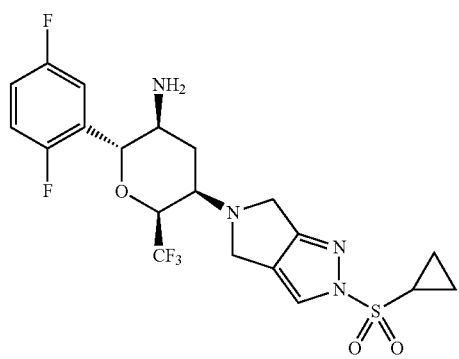
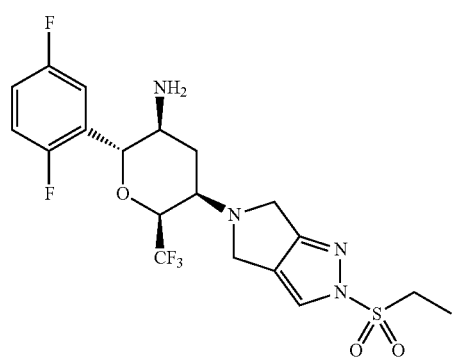
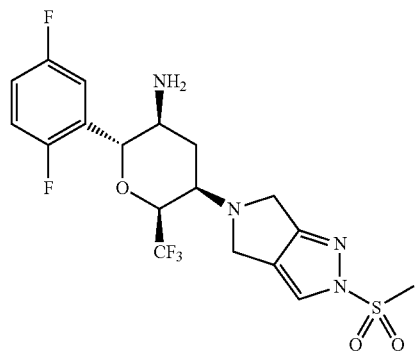
-continued
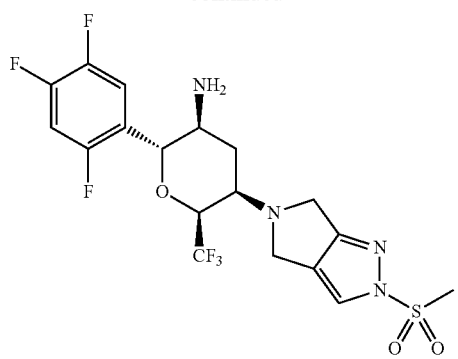
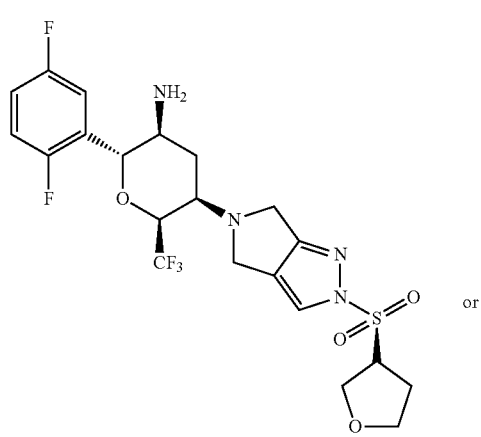
or
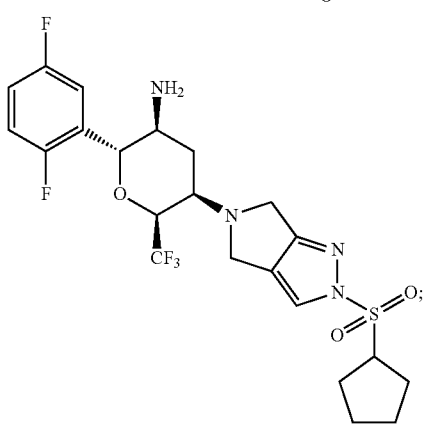
and more preferably
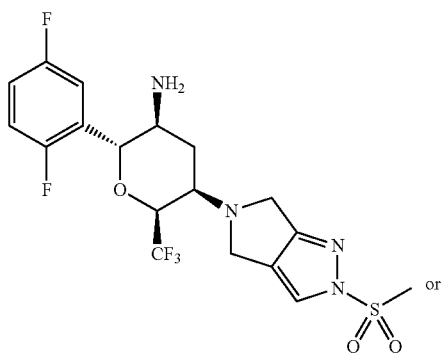
or

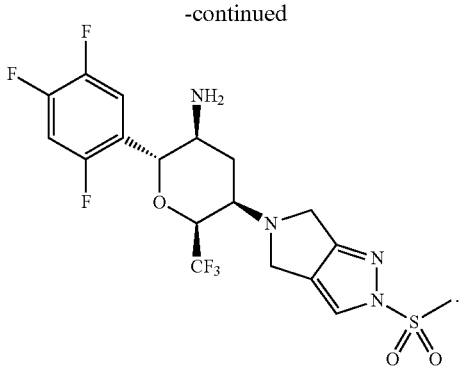

The present invention further relates to a pharmaceutical composition, comprising: an effective amount of the amino pyran ring derivative represented by general formula (I) or a stereoisomer, a pharmaceutically acceptable salt or a prodrug thereof in accordance with any of the embodiment of the present invention described above; and pharmaceutically acceptable carrier(s) or excipient(s).

The present invention further relates to use of a compound represented by general formula (I) or a stereoisomer, a pharmaceutically acceptable salt, a composition thereof, or a prodrug thereof in the manufacture of a DPP-IV inhibitor.

According to the use of the present invention, the DPP-IV inhibitor is used to manufacture a medicament for treating a metabolic disease, wherein the metabolic disease is selected from diabetes, diabetic retinopathy, diabetic neuropathy, diabetic nephropathy, insulin resistance, hyperglycemia, hyperinsulinism, elevated levels of fatty acids or glycerol, hyperlipidemia, obesity, hypertriglyceridemia, X-syndrome, diabetic complications, atherosclerosis, or hypertension.

According to the use of the present invention, the diabetes is type II diabetes.

The present invention further relates to a method for treating a metabolic disease, comprising: administering an amino pyran ring derivative represented by general formula (I) or a stereoisomer, a pharmaceutically acceptable salt, or a prodrug thereof; or any pharmaceutical composition according to the present invention.

According to the method of the present invention, the metabolic disease is selected from diabetes, diabetic retinopathy, diabetic neuropathy, diabetic nephropathy, insulin resistance, hyperglycemia, hyperinsulinism, elevated levels of fatty acids or glycerol, hyperlipidemia, obesity, hypertriglyceridemia, X-syndrome, diabetic complications, atherosclerosis, or hypertension.

According to the method of the present invention, the diabetes is type II diabetes.

Unless otherwise indicated, the terms used throughout the description and claims have the following meanings.

All of the carbon, hydrogen, oxygen, sulfur, nitrogen or halogen involved in the groups and compounds according to the present invention include their isotopes. All of the carbon, hydrogen, oxygen, sulfur, nitrogen or halogen involved in the groups and compounds according to the present invention are optionally further replaced by one or more of their corresponding isotopes, wherein the carbon isotopes include $^{12}C$, $^{13}C$ and $^{14}C$, the hydrogen isotopes include protium (H), deuterium (D, also known as heavy hydrogen) and tritium (T, also known as superheavy hydrogen), the oxygen isotopes include $^{16}O$, $^{17}O$ and $^{18}O$, the sulfur isotopes include $^{32}S$, $^{33}S$, $^{34}S$ and $^{36}S$, the nitrogen isotopes include $^{14}N$ and $^{15}N$, the fluorine isotopes include $^{19}F$, the chlorine isotopes include $^{35}Cl$ and $^{37}Cl$, and the bromine isotopes include $^{79}Br$ and $^{81}Br$.

"Alkyl" means a linear or branched saturated aliphatic hydrocarbyl, having in the main chain 1 to 20 carbon atoms, preferably 1 to 12 carbon atoms, more preferably 1 to 8 carbon atoms, even more preferably 1 to 6 carbon atoms, further preferably 1 to 4 carbon atoms, and most preferably 1 to 2 carbon atoms. Examples of alkyl include, but are not limited to, methyl, ethyl, n-propyl, isopropyl, n-butyl, isobutyl, sec-butyl, t-butyl, n-pentyl, 2-pentyl, 3-pentyl, 2-methyl-2-butyl, 3-methyl-2-butyl, 3-methyl-1-butyl, n-hexyl, 2-hexyl, 3-hexyl, 2-methyl-2-pentyl; 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, 2-methylhexyl, 3-methylhexyl, 4-methylhexyl, 5-methylhexyl, 2,2-dimethylpentyl, 2,3-dimethylpentyl, 2,4-dimethylpentyl, 3,3-dimethylpentyl, 2-ethylpentyl, 3-ethylpentyl, n-octyl, 2,2-dimethylhexyl, 2,3-dimethylhexyl, 2,4-dimethylhexyl, 2,5-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, n-decyl, and the like. The alkyl may be substituted or unsubstituted. If substituted, the substituent(s) may be on any available connecting position(s), and the substituents are preferably 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl heterocycloalkyl, a bridged ring, a spirocyclic group, a fused ring, hydroxyalkyl, =O, carbonyl, an aldehyde group, a carboxyl group, a carboxylate ester, —$(CH_2)_m$—C(=O)—$R^a$, —O—$(CH_2)_m$—C(=O)—$R^a$, —$(CH_2)_m$—C(=O)—$NR^bR^c$, —$(CH_2)_mS(=O)_nR^a$, —$(CH_2)_m$-alkenyl-$R^a$, $OR^d$ or —$(CH_2)_m$-alkynyl-$R^a$ (where m, n are 0, 1 or 2), arylthio, thiocarbonyl, silyl, or —$NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

"Alkoxy" means —O—alkyl, wherein the alkyl is as defined above. Alkoxy may be substituted or unsubstituted. Examples of alkoxy include, but are not limited to, methoxy, ethoxy, n-propoxy, isopropoxy, n-butoxy, isobutoxy, sec-butoxy, t-butoxy, n-pentyloxy, n-hexyloxy, and the like. If substituted, the substituents are preferably 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —$(CH_2)_m$—C(=O)—$R^a$, —O—$(CH_2)_m$—C(=O)—$R^a$, —$(CH_2)_m$—C(=O)—$NR^bR^c$, —$(CH_2)_mS(=O)_nR^a$, —$(CH_2)_m$-alkenyl-$R^a$, $OR^d$ or —$(CH_2)_m$-alkynyl-$R^a$ (where m, n are 0, 1 or 2), arylthio, thiocarbonyl, silyl, or —$NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

"Alkoxyalkyl" means an alkyl attached to an alkoxy, and may be substituted or unsubstituted. Non-limiting examples of alkoxyalkyl include methoxymethyl, methoxyethyl, ethoxymethyl, ethoxyethyl, propoxymethyl, propoxyethyl, 2-propoxymethyl, butoxypropyl, t-butoxyethyl, pentyloxyethyl, hexyloxyethyl, cyclopropoxymethyl, cyclopropoxyethyl, cyclopropoxypropyl, and cyclohexyloxymethyl. If substituted, the substituents are preferably 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; and R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

"Alkenyl" means an alkyl as defined above having at least one carbon-carbon double bond, which has preferably 2 to 20 carbon atoms, more preferably 2 to 12 carbon atoms, and even more preferably 2 to 8 carbon atoms in the main chain, the alkenyl may be substituted or unsubstituted. Non-limiting examples thereof include vinyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 2-octenyl, 1-nonenyl, 3-nonenyl, 1-decenyl, 4-decenyl, 1,3-butadienyl, 1,3-pentadienyl, 1,4-pentadienyl 1,4-hexadienyl, 3-hendecenyl, 4-dodecenyl, 4,8,12-tetradecatrienyl, and the like. If substituted, the substituents are preferably 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

"Alkynyl" means an alkyl as defined above having at least one carbon-carbon triple bond, which has preferably 2 to 20 carbon atoms, more preferably 2 to 8 carbon atoms, and even more preferably has 2 to 4 carbon atoms in the main chain. The alkynyl may be substituted or unsubstituted. Non-limiting examples thereof include ethynyl, -propynyl, 2-propynyl, butynyl, 2-butynyl, 3-butynyl, 1-methyl-2-propynyl, 4-pentynyl, 3-pentynyl, 1-methyl-2-butynyl, 2-hexynyl, 3-hexynyl, 2-heptynyl, 3-heptynyl, 4-heptynyl, 3-octynyl, 3-nonynyl, 4-decynyl, 3-hendecynyl, 4-dodecynyl, and the like. If substituted, the substituents are preferably one or more groups independently selected from F, Cl, Br, I, alkyl, cycloalkyl, alkoxy; haloalkyl, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; and R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

"Amino" means —HN$_2$, which may be substituted or =substituted, If substituted, the substituents are preferably 1 to 3 groups independently selected from alkyl, cycloalkyl, haloalkyl, thiol, hydroxyl, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; and R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

"Alkylthio" means —S-alkyl or —S-(unsubstituted cycloalkyl). Non-limiting examples thereof include methylthio, ethylthio, propylthio, butylthio, and the like.

"Acyl" or "carbonyl" means —C(=O)—R$^a$, where R$^a$ is as defined above.

An "aldehyde group" means —C(=O)—H.

"Halogen" means fluorine, chlorine, bromine, or iodine.

"Hydroxyl" means —OH.

"Cyano" means —C≡N.

"Isocyano" means —N≡C.

"Nitro" means —NO$_2$.

A "carboxyl group" means —C(=O)—OH.

A "carboxylate ester" means —C(=O)—O—R$^d$, where R$^d$ is selected from alkyl, cycloalkyl or heterocycloalkyl.

"Haloalkyl" means an alkyl defined above substituted with a halogen. Non-limiting examples thereof include monofluoromethyl, difluoromethyl, trifluoromethyl, monobromomethyl, dibromomethyl, tribromomethyl, 1-fluoroeth-2-yl, 2-fluoroeth-2-yl, 1,1-difluoroeth-2-yl, 1,2-difluoroeth-2-yl, 1,1,1-trifluoroeth-2-yl, 1-bromoeth-2-yl, 2-bromoeth-2-yl, 1,1,1-tribromoeth-2-yl, and the like.

"Mercapto" means —SH.

"Thiol" means a hydrocarbon in which one or more hydrogen atoms in an alkyl are replaced by mercapto(s). Non-limiting examples thereof include methanethiol, ethanethiol, 1,2-dithiol.

"Thionyl" or "thiocarbonyl" means —C(=S)—R$^a$, where R$^a$ is as defined above.

"Hydroxyalkyl" refers to an alkyl substituted with one or more, preferably 1, 2 or 3, hydroxyls, wherein the alkyl is preferably a lower alkyl. Non-limiting examples thereof include hydroxymethyl, 2-hydroxyethyl, 1-hydroxyethyl, 2-dihydroxypropyl, 1,3-dihydroxypropyl, 2,3-dihydroxypropyl and the like.

"Cycloalkyl" means a saturated or unsaturated non-aromatic cyclic group which may be substituted or unsubstituted, wherein the cyclic carbon atoms include 3 to 20 carbon atoms, preferable 3 to 10 carbon atoms, and more preferably 3 to 8 carbon atoms. Non-limiting examples thereof include cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, 1,5-cyclobutadienyl, 1,4-cyclohexadienyl, cycloheptatrienyl, and the like. If substituted, the substituents may be 1 to 5 groups selected from F, Cl, Br, I alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, $-(CH_2)_m-C(=O)-R^a$, $-O-(CH_2)_m-C(=O)-R^a$, $-(CH_2)_m-C(=O)-NR^bR^c$, $-(CH_2)_mS(=O)_nR^a$, $-(CH_2)_m$-alkenyl-$R^a$, $OR^d$ or $-(CH_2)_m$-alkynyl-$R^a$ (where m, n are 0, 1 or 2), arylthio, thiocarbonyl, silyl, or $-NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

"Heterocycloalkyl" means a substituted or unsubstituted, saturated or unsaturated, non-aromatic ring group at least having 1 to 5 heteroatoms selected from N, O or S, wherein the non-aromatic ring may be a 3- to 10-membered monocyclic ring, or a 4- to 20-membered spiro, fused, or bridged ring(s). The optional N and S substituted in the ring of a heterocycloalkyl may be oxidized to various oxidative states. A 3- to 12-membered heterocycle is preferred. Non-limiting examples of heterocycloalkyl include epoxyethyl, oxacyclobutyl, oxacyclopentyl, oxacyclohexyl, oxacyclooctyl, azacyclopropyl, azacyclobutyl, azacyclopentyl, azacyclohexyl, azacyclopropenyl, 1,3-dioxolanyl, 1,4-dioxolanyl, 1,3-dioxolanyl, 1,3-dioxanyl, 1,3-dithianyl, azacycloheptenyl, morpholinyl, piperazinyl, pyridinyl, furyl, thiophenyl, pyrrolyl, pyranyl, N-alkylpyrrolyl, pyrimidinyl, pyrazinyl, pyridazinyl, imidazolyl, piperidinyl, thiomorpholinyl, dihydropyranyl, thiadiazolyl, oxazolyl, oxadiazolyl, pyrazolyl, 1,4-diazacyclohexadienyl.

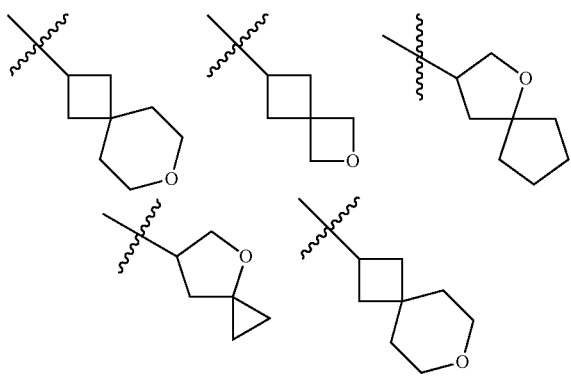

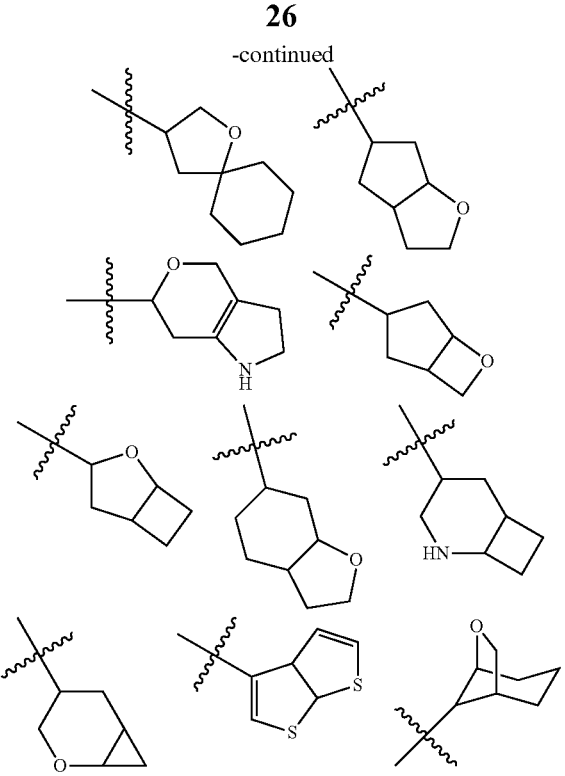

and the like.

If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, $-(CH_2)_m-C(=O)-R^a$, $-O-(CH_2)_m-C(=O)-R^a$, $-(CH_2)_m-C(=O)-NR^bR^c$, $-(CH_2)_mS(=O)_nR^a$, $-(CH_2)_m$-alkenyl-$R^a$, $OR^d$ or $-(CH_2)_m$-alkynyl-$R^a$ (where m, n are 0, 1 or 2), arylthio, thiocarbonyl, silyl, or $-NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

"Spirocyclic" means a 5- to 20-membered polycyclic group in which substituted or unsubstituted monocyclic rings share one common carbon atom (called spiro atom), which may contain 0 to 5 double bonds and may have 0 to 5 heteroatoms selected from N, O or S(=O)$_n$. It is preferable 6- to 14-membered, more preferably 6- to 12-membered, and even more preferably 6- to 10-membered. Non-limiting examples thereof include:

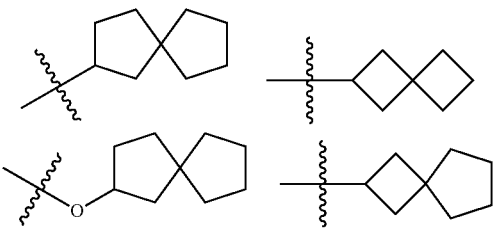

-continued

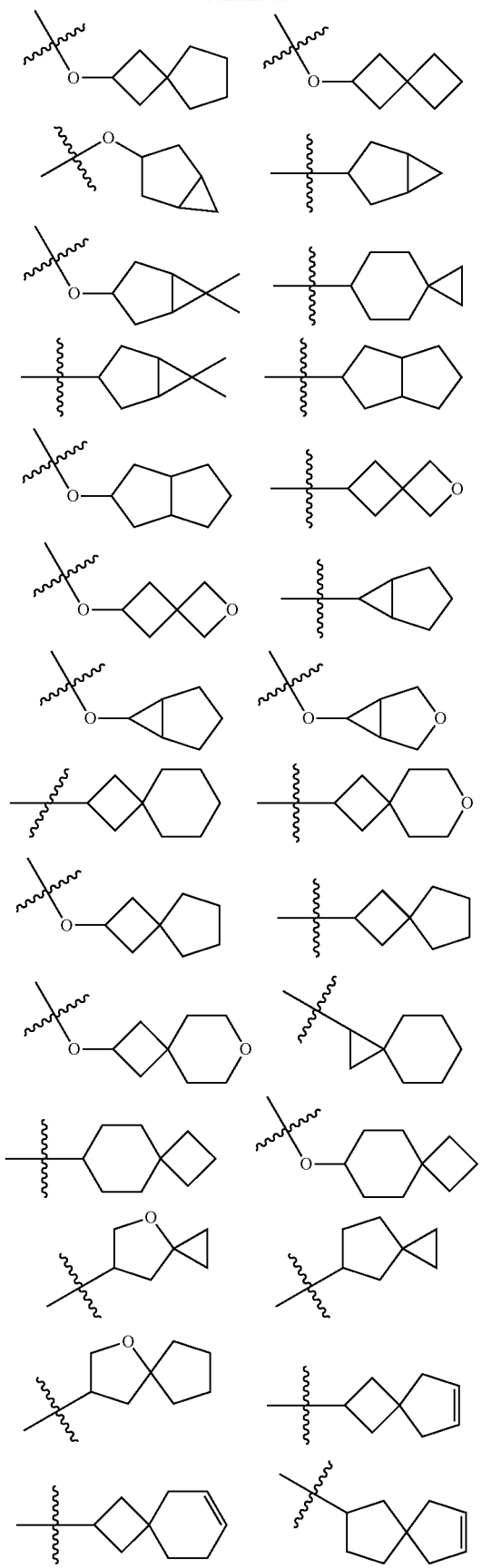

-continued

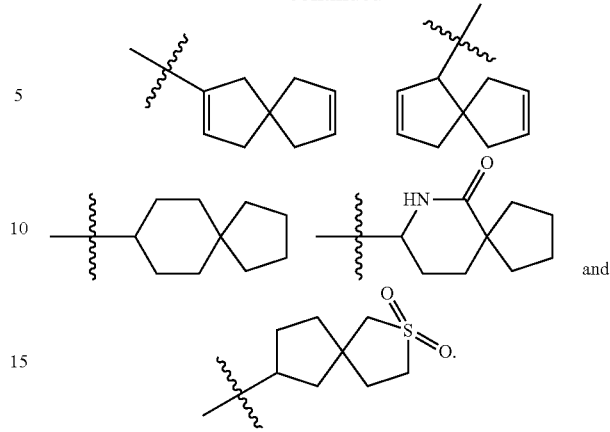

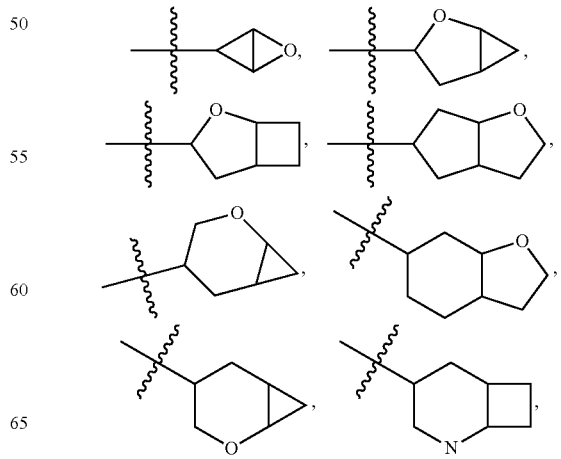

If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, $-(CH_2)_m-C(=O)-R^a$, $-O-(CH_2)_m-C(=O)-R^a$, $-(CH_2)_m-C(=O)-NR^bR^c$, $-(CH_2)_mS(=O)_nR^a$, $-(CH_2)_m$-alkenyl-$R^a$, $OR^d$ or $-(CH_2)_m$-alkynyl-$R^a$ (where m, n are 0, 1 or 2), arylthio, thiocarbonyl, silyl, or $-NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

A "fused ring" means a polycyclic system in which each ring shares a pair of adjacent carbon atoms with another ring in the system, and one or more rings in the system may have 0 or more double bonds and may be substituted or unsubstituted. Each ring in a fused ring system may have 0 to 5 heteroatoms selected from N, $S(=O)_n$ or O. It is preferable 5- to 20-membered, more preferably 5- to 14-membered, even more preferably 5- to 12-membered, and further preferably 5- to 10-membered. Non-limiting examples of a fused ring include:

-continued

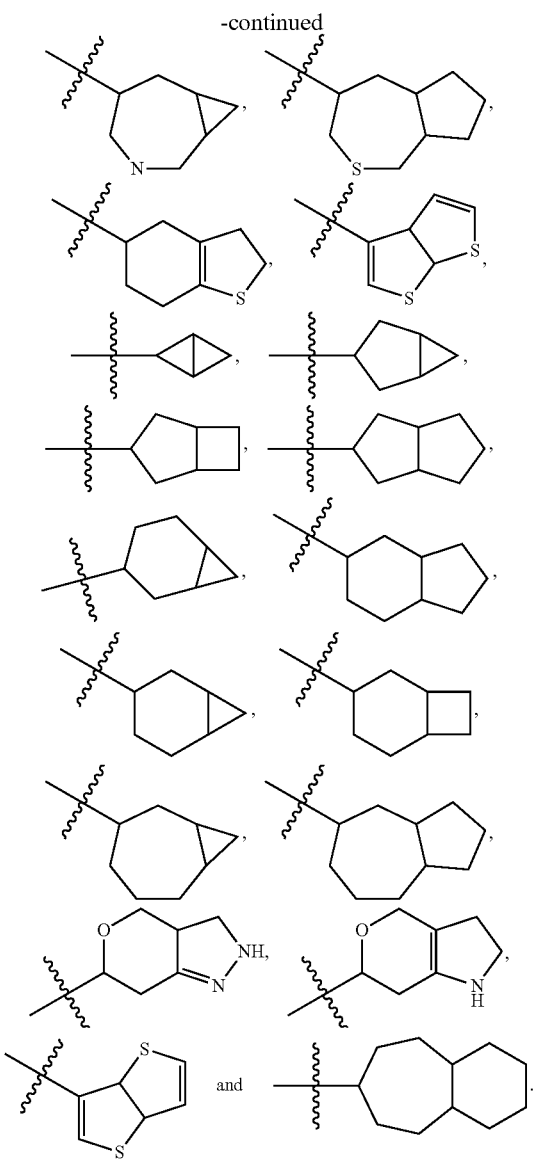

If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —$(CH_2)_m$—C(=O)—$R^a$, —O—$(CH_2)_m$—C(=O)—$R^a$, —$(CH_2)_m$—C(=O)—$NR^bR^c$, —$(CH_2)_mS(=O)_nR^a$, —$(CH_2)_m$-alkenyl-$R^a$, $OR^d$ or —$(CH_2)_m$-alkynyl-$R^a$ (where m, n are 0, 1 or 2), arylthio, thiocarbonyl, silyl, or —$NR^bR^c$, wherein $R^b$ and $R^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively $R^b$ and $R^c$ may form a 5- or 6-membered cycloalkyl or heterocycloalkyl; and $R^a$ and $R^d$ are each independently selected from aryl, heteroaryl, alkyl, alkoxy, cycloalkyl, heterocycloalkyl, carbonyl, an ester group, a bridged ring, a spirocyclic group, and a fused ring.

A "bridged ring" means a polycyclic group in which two carbon atoms that are not adjacent are bridged. It can have 0 or more double bonds, and may be substituted or unsubstituted. Any ring in a bridged ring system may have 0 to 5 heteroatoms or group selected from N, S(=O)$_n$ or O (where n is 1, or 2). The ring atoms contain 5 to 20 atoms, preferably 5 to 14 atoms, more preferably 5 to 12 atoms, and further preferably 5 to 10 atoms. Nonlimiting examples of a bridge ring include:

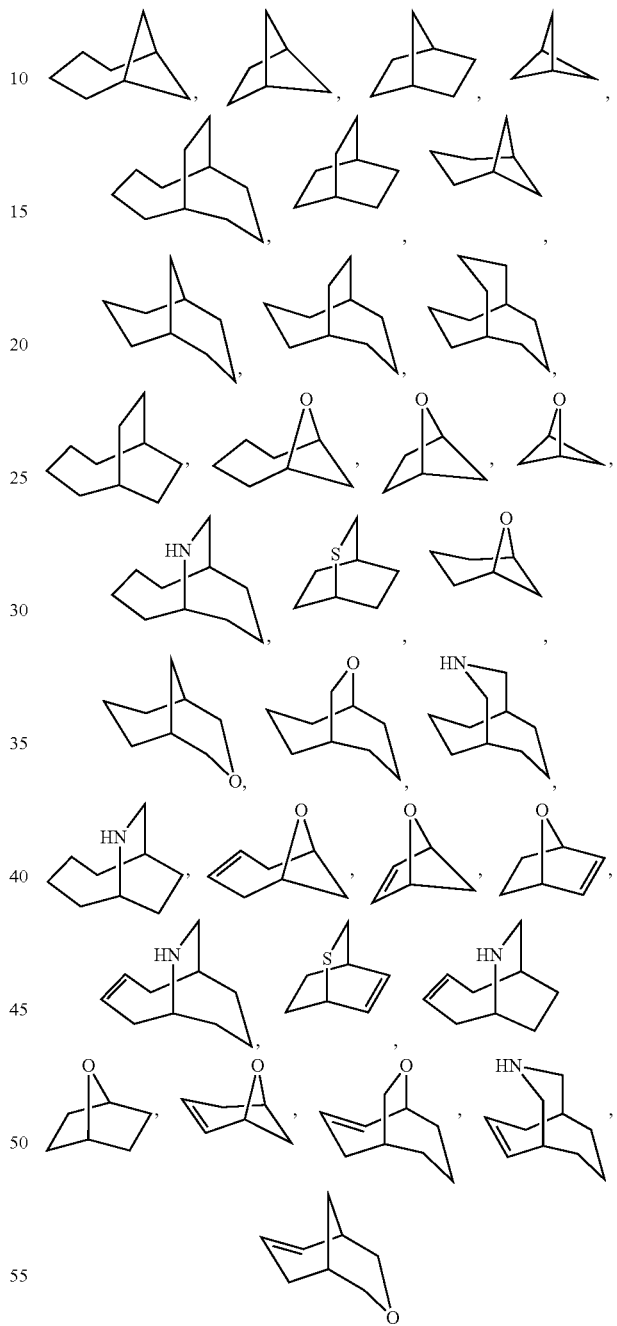

and adamantane. If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —$(CH_2)_m$—C(=O)—$R^a$, —O—$(CH_2)_m$—C(=O)—$R^a$, —$(CH_2)_m$—C(=O)—$NR^bR^c$, —$(CH_2)_mS(=O)_nR^a$, —$(CH_2)_m$-alkenyl-$R^a$, $OR^d$ or —$(CH_2)_m$-alkynyl-$R^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; and R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

"Benzyl" means —CH$_2$-phenyl, wherein the phenyl may be substituted or unsubstituted. Non-limiting examples thereof include —CH$_2$-phenyl, —CH$_2$-(p-tolyl), and the like.

"Aryl" means a substituted or unsubstituted 6- to 14-membered cyclic aromatic group, including monocyclic aromatic groups and fused-ring aromatic groups. It is preferably a 6- to 14-membered aromatic ring, more preferably 6- to 10-membered aromatic ring. Non-limiting examples thereof include phenyl, naphthyl, anthracyl, phenanthryl, and the like. The aryl ring may be fused to a heteroaryl, a heterocycloalkyl or a cycloalkyl, wherein the ring attached to the core structure is the aryl ring, and non-limiting examples thereof include "Heteroaryl" means a substituted or unsubstituted 5- to 14-membered aromatic ring containing 1 to 5 heteroatoms or groups selected form N, O, or S(=O)$_n$. It is preferably a 5- to 10-membered heteroaromatic ring, more preferably a 5- to 6-membered heteroaromatic ring. Non-limiting examples of heteroaryl include, but not limited to, pyridyl, furyl, thiophenyl, pyridyl, pyranyl, N-alkylpyrrolyl, pyrimidinyl, pyrazinyl, pyridazinyl, imidazolyl, piperidinyl, morpholinyl, thiomorpholinyl, 1,3-dithianyl, benzimidazole, piperidinyl, benzimidazole, benzopyridinyl, pyrropyridinyl, and the like. The heteroaryl ring may be fused to an aryl, a heterocycloalkyl or a cycloalkyl, wherein the ring attached to the core structure is the heteroaryl ring, and non-limiting examples thereof include

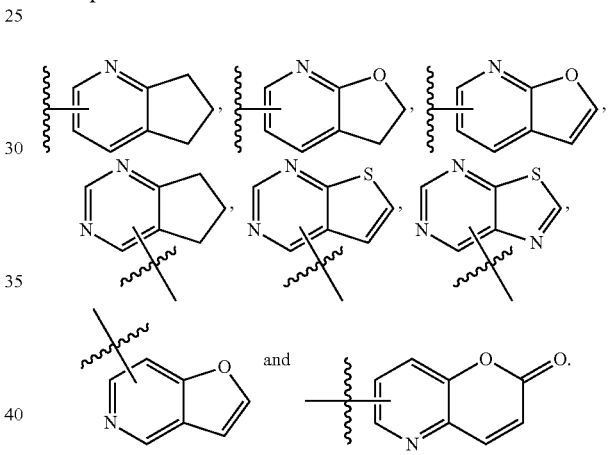

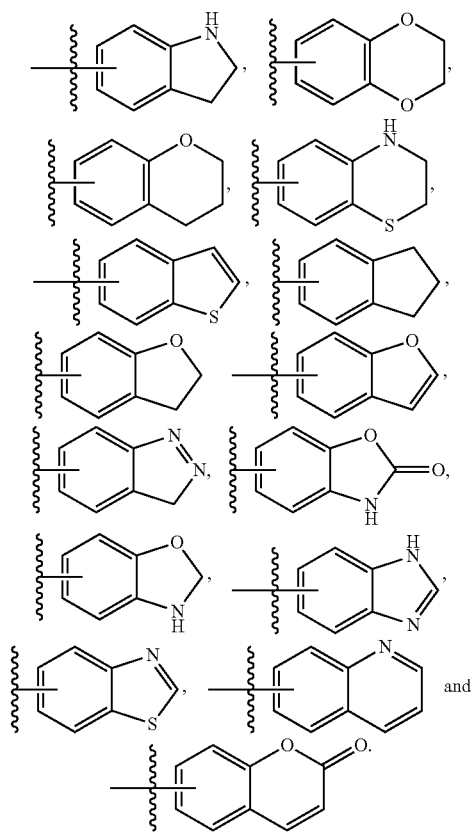

If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where m, n are 0, 1 or 2), arylthio, thiocarbonyl, silyl, or —NR$^b$R$^c$, wherein R$^b$ and R$^c$ are independently selected from H, hydroxyl, amino, carbonyl, alkyl, alkoxy, cycloalkyl, heterocycloalkyl, aryl, heteroaryl, sulfonyl, and trifluoromethanesulfonyl, or alternatively R$^b$ and R$^c$ may form a 5- or 6-membered cycloalkyl or heterocycloalkyl; and R$^a$ and R$^d$ are each independently selected from aryl, heteroaryl, alkyl, alkoxy, cycloalkyl, heterocycloalkyl, carbonyl, an ester group, a bridged ring, a spirocyclic group, and a fused ring.

If substituted, the substituents may be 1 to 5 groups selected from F, Cl, Br, I, alkyl, cycloalkyl, alkoxy, haloalkyl, thiol, hydroxyl, nitro, mercapto, amino, cyano, isocyano, aryl, heteroaryl, heterocycloalkyl, a bridged ring, a spirocyclic group, a fused ring, hydroxyalkyl, =O, carbonyl, an aldehyde group, a carboxyl group, a carboxylate ester, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (where "Arylthio" means —S-aryl or —S-heteroaryl, as defined herein. Examples of arylthio include, but are not limited to, phenylthio, pyridinylthio, furylthio, thiophenylthio, pyrimidinyl, and the like.

"Silyl" means a group obtained by replacing one or more hydrogen atoms in a silane with alkyl(s). Examples thereof include, but are not limited to, trimethylsilyl, triethylsilyl, t-butyl(dimethyl)silyl, t-butyl(diphenyl)silyl, and the like.

The term "single bond" means a single chemical bond. For example, "one single bond between A and B" means that there is one single chemical bond between A and B, i.e., A-B.

"Optional" or "optionally" means that the event or scenario described by them may, but does not have to, happen, and encompasses both cases where the event or scenario happens and does not happens. For example, "an alkyl optionally substituted with F" means that the alkyl may, but does not have to, be substituted with F, encompassing both the case where the alkyl is substituted with F and the case where the alkyl is not substituted with F.

A "pharmaceutically acceptable salt" or "pharmaceutically acceptable salt thereof" refers to a salt obtained by reaction between a free acid of interest and a nontoxic inorganic or organic base, or by reaction between a free base of interest and a nontoxic inorganic or organic acid, wherein the bioavailability and characteristics of the free acid or free base is retained.

"Carrier" means a vehicle or diluent that does not cause significant stimulation to an organism and does not eliminate the biological activity and characteristics of a given compound.

"Excipient" means an inert substance added into a pharmaceutical composition to further facilitate administration of a compound. Examples thereof include, but are not limited to, calcium carbonate, calcium phosphate, various sugars, different types of starch, cellulose derivatives (including microcrystalline cellulose), gelatin, vegetable oils, polyethylene glycols, diluent, a granulating agent, lubricant binder and disintegrant.

A "prodrug" means a compound that can be converted under physiological conditions or under the action of solvent into the biologically active compound of the present invention. A prodrug of the present invention is prepared by modification of the phenol group of the compound of the present invention. Such a modification can be removed in vivo or by conventional operations, so as to produce the parent compound. When a prodrug of the present invention is administered to a mammalian subject, it is cleaved to give free hydroxyl. Examples of a prodrug include, but are not limited to, phenolic hydroxyl and phosphoric acid to form a sodium salt derivatives of the compound of the present invention.

Some of the compounds described herein may exist as tautomers, and have different hydrogen linking points with the relocation of one or more double bonds, for example ketone-enol tautomers. Individual tautomers and a mixture thereof are included in the scope of the present invention. Tautomers within the scope of the present invention include but are not limited to:

The compounds described herein may have one or more asymmetric centers, and thus may exist as a racemate, a racemic mixture, a single enantiomer, a mixture of diastereomers, and a single diastereomer.

Some of the compounds described herein contain double bonds, and unless otherwise indicated, contain E and Z geometrical isomers.

A "cocrystal" refers to a crystal formed by combination of an active pharmaceutical ingredient (API) and a cocrystal former (CCF) via hydrogen bonds or other non-covalent bonds, wherein both the API and CCF in their pure form are solid at room temperature and these components are present in a fixed stoichiometric ratio therebetween. A cocrystal is a multi-component crystal, including both a binary cocrystal formed from two neutral solids and a multiple cocrystal formed from a neutral solid and a salt or solvate.

The "X syndrome" refers to a disorder, disease, or condition of the metabolic syndrome. A detailed description thereof can be seen in Johannsson *J. Clin. Endocrinol. Metab.*, 1997, 82, 727-734.

An "effective amount" means an amount that causes a physiological or medical response in a tissue, system or subject and is a desirable amount, including the amount of a compound that is, after being administered to a subject to be treated, sufficient to prevent occurrence of one or more symptoms of the disease or disorder to be treated or to reduce the symptom(s) to a certain degree.

A "solvate" refers to the compound of the present invention or a salt thereof that further contains a stoichiometric or non-stoichiometric amount of solvent bound via a non-covalent intermolecular force. When the solvent is water, the solvate is a hydrate.

"IC50" means half maximal inhibitory concentration, the concentration that achieves half of the maximum inhibitory effect.

The Synthesis Method of the Compound of the Present Invention

For the purpose of the present invention, the compound of the present invention may be prepared by the following scheme:

Scheme I:

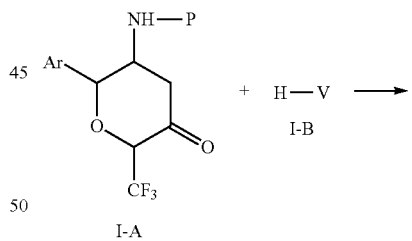

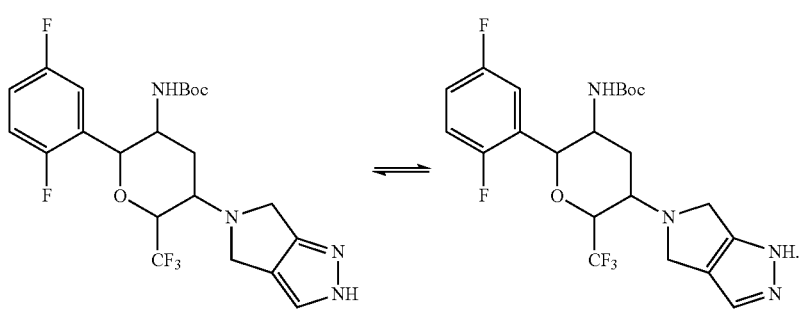 [SMILES: CC(C)(C)OC(=O)NC1CC(N2Cc3c[nH]nc3C2)C(C(F)(F)F)OC1c1cc(F)ccc1F ; CC(C)(C)OC(=O)NC1CC(N2Cc3cn[nH]c3C2)C(C(F)(F)F)OC1c1cc(F)ccc1F]

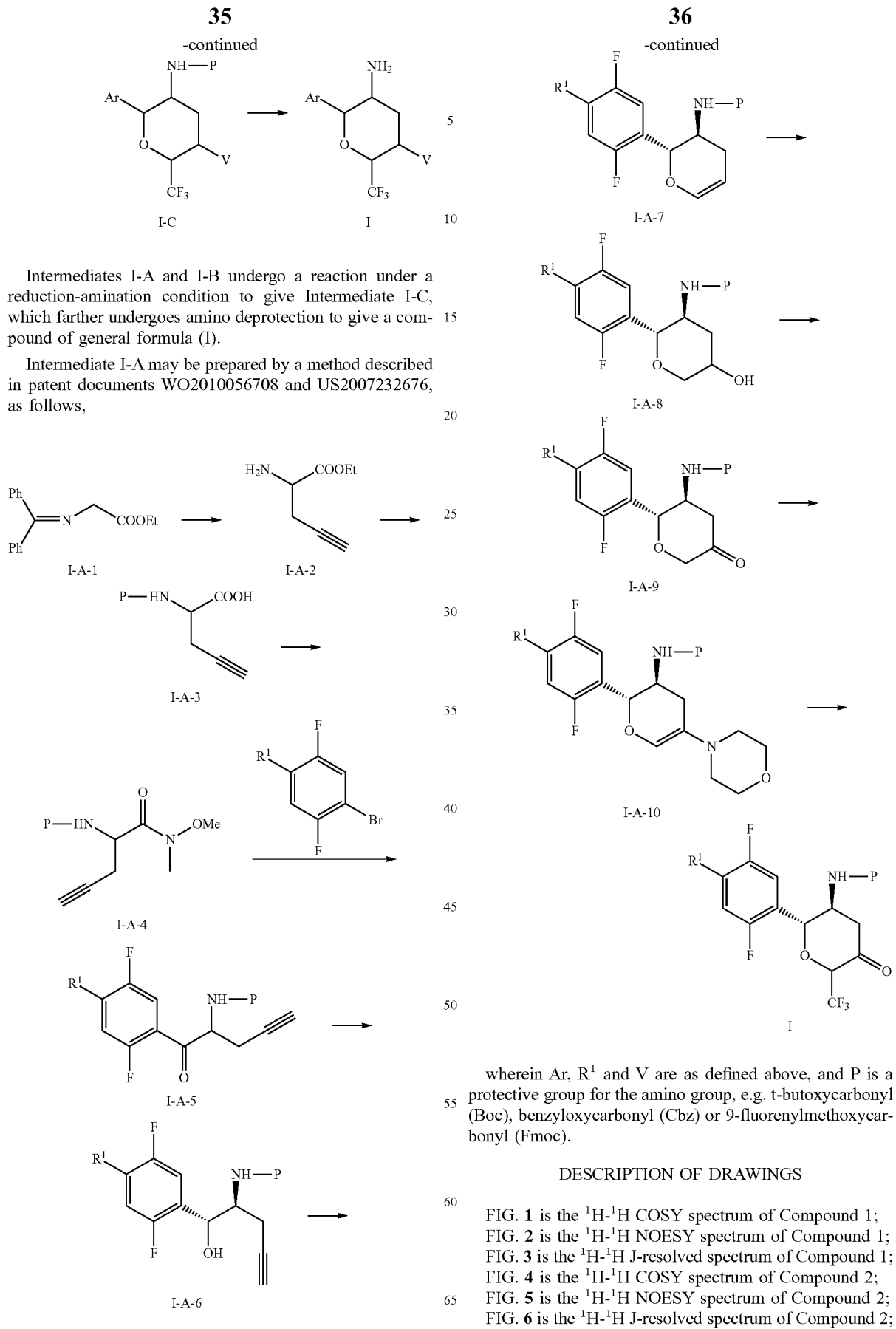

Intermediates I-A and I-B undergo a reaction under a reduction-amination condition to give Intermediate I-C, which farther undergoes amino deprotection to give a compound of general formula (I).

Intermediate I-A may be prepared by a method described in patent documents WO2010056708 and US2007232676, as follows, wherein Ar, $R^1$ and V are as defined above, and P is a protective group for the amino group, e.g. t-butoxycarbonyl (Boc), benzyloxycarbonyl (Cbz) or 9-fluorenylmethoxycarbonyl (Fmoc).

DETAILED DESCRIPTION OF INVENTION

Figure 1:
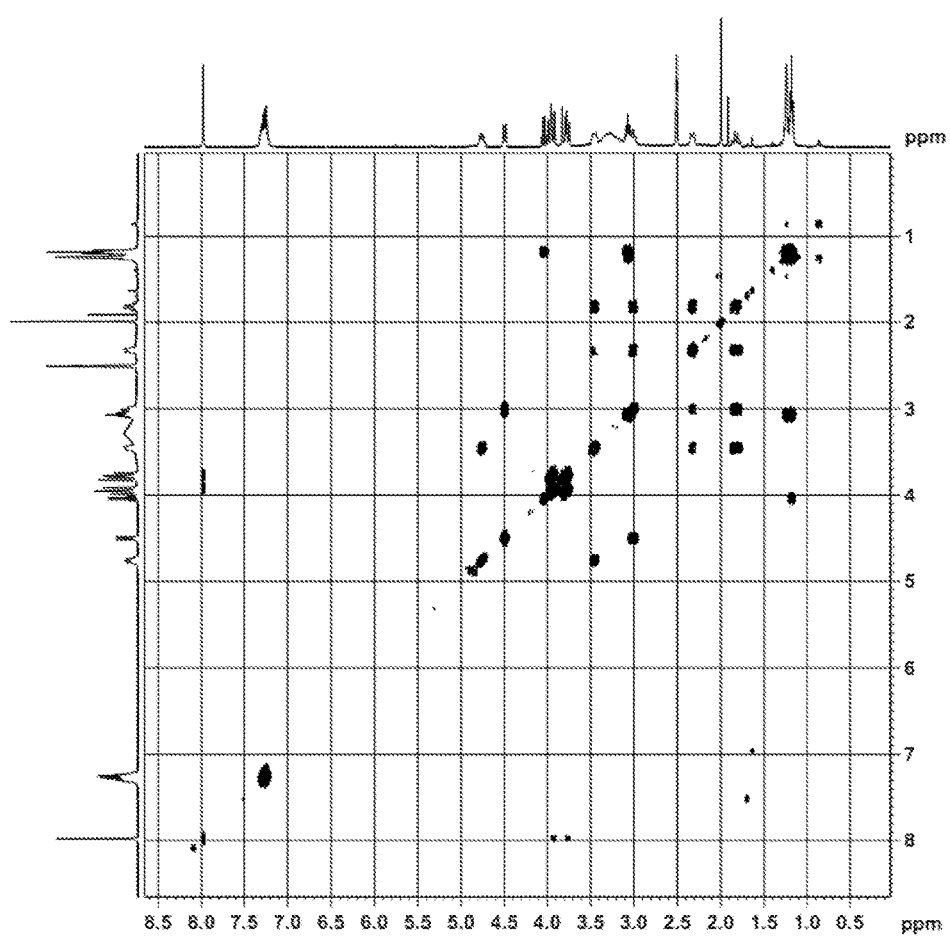
FIG. 1 is the $^1$H-$^1$H COSY spectrum of Compound 1.

Hereinafter the technical solutions of the present invention will be described in details in conjunction with the drawings and examples. However, the scope of the present invention is not limited thereto.

The structures of compounds were determined by nuclear magnetic resonance (NMR) and/or mass spectroscopy (MS).

NMR shifts (δ) are presented in $10^{-6}$ ppm.

NMR measurements were performed with a Bruker ADVANCE III 400 NMR device, wherein the measurement solvents were hexadeuterodimethyl sulfoxide (DMSO-d$_6$), deuterochloroform (CDCl$_3$), and deuteromethanol (CD$_3$OD), and the internal reference was tetramethylsilane (TMS). $^1$NMR information is expressed in the following format: Chemical shift (Multiplet (s, singlet; d, doublet; t, triplet; q, quartet; m, multiplet), Number of protons).

MS measurements were performed with Agilent 6120B (ESI).

HPLC measurements were performed with Agilent 1260 DAD High-pressure Liquid Chromatograph (ZorbaxSB-C18 100×4.6 mm).

Thin-layer chromatography silica gel plate: HSGF254 silica gel plate (Huanghai, Yantai) or GF254 silica gel plate (Qingdao). The specification of the silica gel plate used for thin-layer chromatography (TLC) was 0.15 mm to 0.20 mm, and that for product isolation and purification by TLC was 0.4 mm to 0.5 mm.

The chromatography column generally used the silica gel (Huanghai, Yantai) of 200 to 300 mesh as a carrier.

Unless otherwise specified, triethylamine, methyl t-butyl ether, hydrazine hydrate, tetrabutylammonium bromide, dichlorosulfoxide, imidazole, sodium hydride, triphenylphosphine, and trifluoroacetic acid were purchased from Chengdu Kelong Chemical Industry Reagents Manufactory; di(t-butyl) dicarbonate, N,N'-dicarbonyl diimidazole, N,N-dimethylformamide dimethyl acetal, N,O-dimethyl hydroxylamine hydrochloride, and cis-4-hydroxyl-D-proline hydrochloride were purchased from Astatech Medicine Technology Co. Ltd. (Chengdu); cesium carbonate, lithium borohydride, t-butyl(dimethyl)chlorosilane, N-hydroxysuccimide, sodium di(trimethylsilyl)amine, ethyl(diphenylmethylenamino) acetate, and trans-L-hydroxyproline were purchased from Energy Chemical; Dess-Martin periodinane was purchased from Shanghai Titan Scientific Co. Ltd.; methyl trifluoromethanesulfonate, 2,5-difluorobromobenzene, and S-(trifluoromethyl)dibenzothiophenium trifluoromethanesulfonate were purchased from Shanghai Demochem Co,. Ltd.; 2-iodopropane was purchased from Shanghai Bide Pharmatech Co. Ltd.; isopropylmagnesium chloride/lithium chloride solution in tetrahydrofuran was purchased from J&K Scientific Co. Ltd.; propynolbenzenesulfonate, tetrabutylammonium fluoride, tri(acetoxy)sodium borohydride, and tetrabutylammonium hexafluorophosphate were purchased from Shanghai Adamas-beta Co. Ltd.; cyclopentadienylbis(triphenylphosphine)ruthenium(II) chloride was purchased from ACROS organics; borane-dimethyl sulfide was purchased from Accela ChemBio Co. Ltd. (Shanghai); tetrahydrofuran-3-sulfonyl chloride was purchased from Nanjing Chemlin Chemical Industry Co. Ltd.; sodium perborate was purchased from Tianjin Guangfu Fine Chemical Research Institute; [(R,R)-N-(2-amino-1,2-diphenylethyl)pentafluorophenylsulfonylamido](p-cymene) ruthenium (II) chloride was purchased from Strem chemical; iodomethane and methylsulfonyl chloride were purchased from Sinopharm Group.

A N$_2$ atmosphere means that the reaction vessel is connected to a N$_2$ balloon of about 1 L in volume.

A H$_2$ atmosphere means that the reaction vessel is connected to a H$_2$ balloon of about 2 L in volume.

Hydrogenation reaction generally involves a vacuuming and H$_2$-charging operation repeating 3 times.

In the Examples, unless particularly specified, solutions refer to aqueous solutions.

In the Examples, unless particularly specified, reaction temperatures are room temperature, and the most suitable room temperature as a reaction temperature is 20° C. to 30° C.

Intermediate 1:

tert-butyl ((2R,3S)-2-(2,5-difluorophenyl)-5-oxo-6-(trifluoromethyl)tetrahydro-2H-pyran-3-yl)carbamate (Intermediate 1)

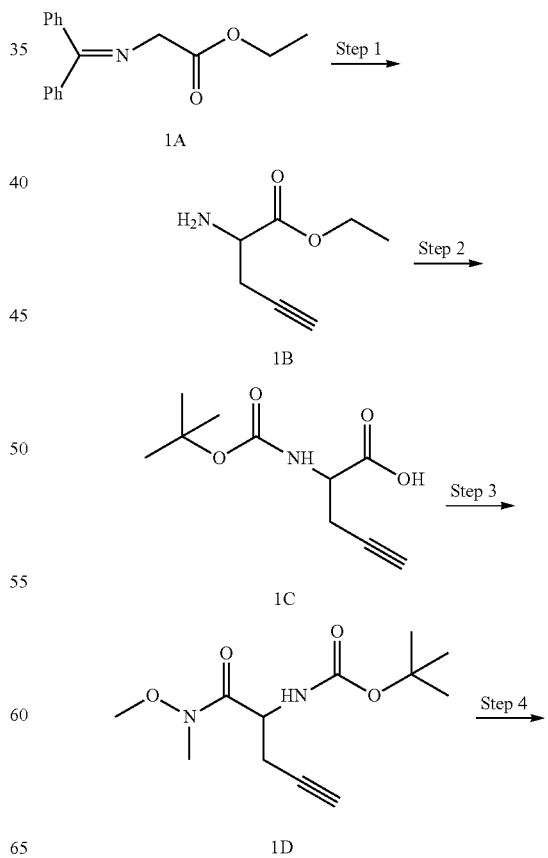

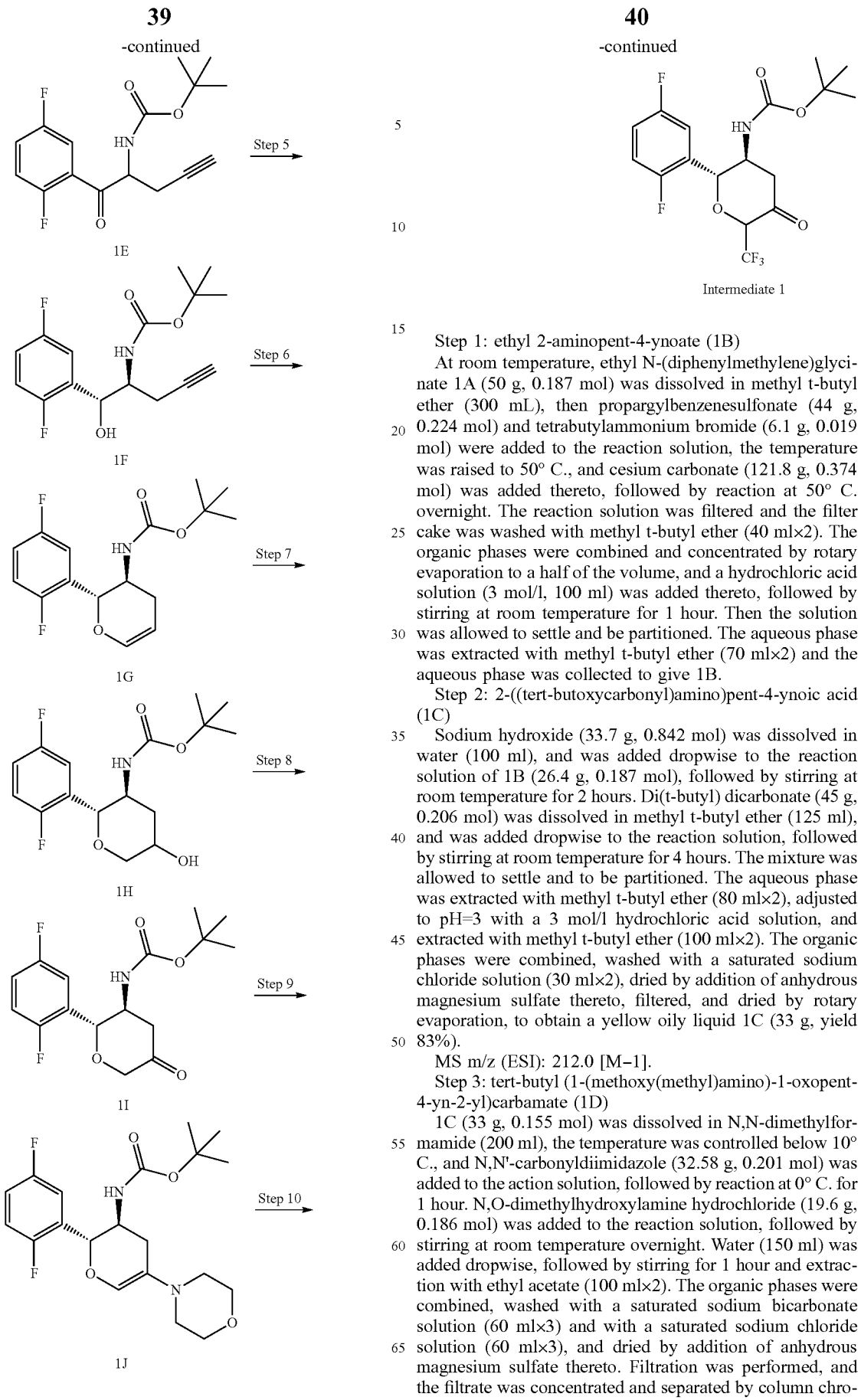

Step 1: ethyl 2-aminopent-4-ynoate (1B)

At room temperature, ethyl N-(diphenylmethylene)glycinate 1A (50 g, 0.187 mol) was dissolved in methyl t-butyl ether (300 mL), then propargylbenzenesulfonate (44 g, 0.224 mol) and tetrabutylammonium bromide (6.1 g, 0.019 mol) were added to the reaction solution, the temperature was raised to 50° C., and cesium carbonate (121.8 g, 0.374 mol) was added thereto, followed by reaction at 50° C. overnight. The reaction solution was filtered and the filter cake was washed with methyl t-butyl ether (40 ml×2). The organic phases were combined and concentrated by rotary evaporation to a half of the volume, and a hydrochloric acid solution (3 mol/l, 100 ml) was added thereto, followed by stirring at room temperature for 1 hour. Then the solution was allowed to settle and be partitioned. The aqueous phase was extracted with methyl t-butyl ether (70 ml×2) and the aqueous phase was collected to give 1B.

Step 2: 2-((tert-butoxycarbonyl)amino)pent-4-ynoic acid (1C)

Sodium hydroxide (33.7 g, 0.842 mol) was dissolved in water (100 ml), and was added dropwise to the reaction solution of 1B (26.4 g, 0.187 mol), followed by stirring at room temperature for 2 hours. Di(t-butyl) dicarbonate (45 g, 0.206 mol) was dissolved in methyl t-butyl ether (125 ml), and was added dropwise to the reaction solution, followed by stirring at room temperature for 4 hours. The mixture was allowed to settle and to be partitioned. The aqueous phase was extracted with methyl t-butyl ether (80 ml×2), adjusted to pH=3 with a 3 mol/l hydrochloric acid solution, and extracted with methyl t-butyl ether (100 ml×2). The organic phases were combined, washed with a saturated sodium chloride solution (30 ml×2), dried by addition of anhydrous magnesium sulfate thereto, filtered, and dried by rotary evaporation, to obtain a yellow oily liquid 1C (33 g, yield 83%).

MS m/z (ESI): 212.0 [M−1].

Step 3: tert-butyl (1-(methoxy(methyl)amino)-1-oxopent-4-yn-2-yl)carbamate (1D)

1C (33 g, 0.155 mol) was dissolved in N,N-dimethylformamide (200 ml), the temperature was controlled below 10° C., and N,N'-carbonyldiimidazole (32.58 g, 0.201 mol) was added to the action solution, followed by reaction at 0° C. for 1 hour. N,O-dimethylhydroxylamine hydrochloride (19.6 g, 0.186 mol) was added to the reaction solution, followed by stirring at room temperature overnight. Water (150 ml) was added dropwise, followed by stirring for 1 hour and extraction with ethyl acetate (100 ml×2). The organic phases were combined, washed with a saturated sodium bicarbonate solution (60 ml×3) and with a saturated sodium chloride solution (60 ml×3), and dried by addition of anhydrous magnesium sulfate thereto. Filtration was performed, and the filtrate was concentrated and separated by column chromatography (petroleum ether/ethyl acetate (v/v)=10:1) to obtain a white solid 1D (35 g, yield 88.2%).

MS m/z (ESI): 156.9 [M−99].

Step 4: tert-butyl (1-(2,5-difluorophenyl)-1-oxopent-4-yn-2-yl)carbamate (1E)

Under $N_2$ protection, 2,5-difluorobromobenzene (15.05 g, 78 mmol) was dissolved in dry toluene (50 ml), cooled to −10° C. or lower in an ice salt bath, and a solution of isopropyl magnesium chloride/lithium chloride in tetrahydrofuran (66 ml, 1.3 mol/l) was added dropwise, followed by stirring at about −10° C. for 1 hour. 1D (10 g, 39 mmol) was dissolved in dry tetrahydrofuran (100 ml), and added dropwise to the reaction solution while the temperature was maintained at −10° C. When the addition was complete, the reaction was allowed to proceed at room temperature for 4 hours. The temperature was lowered to about −10° C., and a saturated ammonium chloride solution (40 ml) was added dropwise, followed by stirring for 10 min. The pH was adjusted to 5 to 6 with a 3 mol/l hydrochloric acid solution, to allow settling and partitioning. The aqueous phase was extracted with methyl t-butyl ether (50 ml×2). The organic phases were combined, washed with a saturated sodium chloride solution (30 ml×2), dried by addition of anhydrous sodium sulfate thereto, filtered, concentrated, and separated by column chromatography (petroleum ether/ethyl acetate (v/v)=50:1 to 8:1), to obtain a light yellow solid 1E (10.1 g, yield 83.5%).

MS m/z (ESI): 210.1 [M−99].

Step 5: tert-butyl((1R,2S)-1-(2,5-difluorophenyl)-1-hydroxypent-4-yn-2-yl) carbamate (1F)

1E (16.07 g, 52 mmol) was dissolved in tetrahydrofuran (100 ml), triethylenediamine (17.39 g, 155 mmol) and [(R,R)-N-(2-amino-1,2-diphenethyl)pentafluorobenzenesulfonamide](p-cymene)ruthenium(II) chloride (i.e. RuCl(p-cymene)(R,R)-FSDPEN) (0.37 g, 0.52 mmol) were added thereto, and formic acid (14.27 g, 310 mmol) was added dropwise, followed by reaction at 40° C. overnight. The tetrahydrofuran and formic acid in the reaction solution were removed by rotary evaporation, and water (60 ml) and hydrochloric acid (3 mol/l, 10 ml) were added, followed by extraction with methyl t-butyl ether (90 ml×3). The organic phases were combined, washed with a saturated sodium bicarbonate solution (35 ml×2), dried by addition of anhydrous magnesium sulfate thereto, filtered, concentrated, and separated by column chromatography (petroleum ether/ethyl acetate (v/v)=60:1 to 10:1), to obtain a light yellow jelly substance 1F (15.37 g, yield 95%).

MS m/z (ESI): 334.2 [M+23].

Step 6:

tert-butyl((2R,3S)-2-(2,5-difluorophenyl)-3,4-dihydro-2H-pyran-3-yl)carbamate (1G)

1F (15.37 g, 49.4 mmol) was dissolved in N,N-dimethylformamide (75 ml) while being heated, and tetrabutylammonium hexafluorophosphate (2.49 g, 6.42 mmol), N-hydroxy succinimide (2.84 g, 24.75 mmol), triphenylphosphine (0.86 g, 3.26 mmol), and sodium bicarbonate (2.16 g, 25.69 mmol) were added thereto, followed by $N_2$ purging for 3 times and vacuum pumping for 15 min. Then cyclopentadienyl bis(triphenylphosphine)ruthenium (II) chloride (i.e. CpRuCl(PPh$_3$)$_2$) (1.79 g, 2.47 mmol) was added, followed by $N_2$ purging for 3 times and vacuum pumping for 15 min. Under $N_2$ protection, the temperature was raised to 85° C., followed by reaction overnight. Water (300 ml) and methyl t-butyl ether (200 ml) were added to the reaction solution, which was then filtered through silica gel, and the filtrate was allowed to settle and be partitioned. The aqueous phase was extracted with methyl t-butyl ether (90 ml×2). The organic phases were combined, washed with a saturated sodium bicarbonate solution (60 ml×2), dried by addition of anhydrous sodium sulfate thereto, filtered, concentrated, and separated by column chromatography (petroleum ether/ethyl acetate (v/v)=80:1 to 30:1), to obtain a light yellow powdery solid 1C (8.9 g, yield 57.9%).

MS m/z (ESI): 256.2 [M−55].

Step 7:

tert-butyl((2R,3S)-2-(2,5-difluorophenyl)-5-hydroxytetrahydro-2H-pyran-3-yl)carbamate (1H)

1G (8.9 g, 28.6 mmol) was dissolved in dry methyl t-butyl ether (90 ml), dry toluene (9 ml) was added thereto, the temperature was lowered to −10° C., and a solution of borane dimethyl sulfide in tetrahydrofuran (2 mol/l, 35.9 ml) was added dropwise, followed by reaction at 0° C. for 3.5 hours. Water (4 ml) was added slowly, a sodium hydroxide solution (1 mol/l, 89 ml) was added dropwise, followed by stirring for 15 min, and sodium perborate (13.2 g, 85.8 mmol) was added in batches, followed by stirring at room temperature overnight. The reaction solution was allowed to settle and be partitioned, and the aqueous phase was extracted with methyl t-butyl ether (50 ml×2). The organic phases were combined, washed with a saturated sodium chloride solution (20 ml×2), dried by addition of anhydrous sodium sulfate thereto, filtered, concentrated, followed by addition of toluene (50 ml), and dissolved by heating to 90° C. n-hexane (200 ml) was added dropwise to the reaction solution to precipitate a white solid, followed by filtration. The filter cake was washed with n-hexane (30 ml×2), and the solvent was removed by concentrating, to obtain a white solid powder 1H (7.9 g, yield 84%).

MS m/z (ESI): 274.1 [M−55].

Step 8:

tert-butyl((2R,3S)-2-(2,5-difluorophenyl)-5-hydroxytetrahydro-2H-pyran-3-yl)carbamate (1I)

1H (11.53 g, 35.03 mmol) was dissolved in dichloromethane (130 ml), and cooled to 0° C. Dess-Martin periodinane (29.72 g, 70.06 mmol) was added in batches to the reaction solution, which was allowed to warm spontaneously to room temperature and undergo reaction for 4 hours. The temperature was lowered to 0° C., and a saturated sodium bicarbonate solution (60 ml) was added dropwise to the reaction solution, followed by stirring for 20 min and filtration. The filtrate was allowed to settle and be partitioned, and the aqueous phase was extracted with methyl t-butyl ether (60 ml×3). The organic phases were combined, washed with a saturated sodium bicarbonate solution (30 ml×2), dried by addition of anhydrous sodium sulfate thereto, filtered, concentrated, and separated by column chromatography (petroleum ether/ethyl acetate (v/v)=10:1 to 4:1), to obtain a white crystalline powder 1I (10.85 g, yield 94.7%).

MS m/z (ESI): 274.1 [M−55];

$^1$H NMR (400 MHz, DMSO-d$_6$): δ 7.29-7.13 (m, 4H), 4.77-4.75 (d, 1H), 4.22-4.02 (m, 3H), 2.75-2.70 (m, 2H), 1.23 (s, 9H).

Step 9:

tert-butyl N-[(2R,3S)-2-(2,5-difluorophenyl)-5-morpholino-3,4-dihydro-2H-pyran-3-yl]carbamate (1J)

1I (2.5 g, 7.64 mmol) was added to 40 ml toluene, morpholine (1.30 g, 15.30 mmol) was added thereto, the reaction solution was heated to reflux while water was separated by a water segregator, and the reaction was allowed to proceed for 6 hours. The reaction solution was cooled to room temperature to precipitate a solid, which was filtered by suction filtration and washed with toluene to obtain a white solid 1J (2.1 g, yield 70%).

¹H NMR (400 MHz, DMSO-d₆): δ 7.27-7.12 (m, 3H), 6.89 (d, 1H), 6.10 (s, 1H), 4.55 (d, 1H), 3.99-3.83 (m, 1H), 3.61 (t, 4H), 2.64 (qd, 4H), 2.41-2.20 (m, 2H), 1.27-1.10 (m, 9H).

Step 10: tert-butyl ((2R,3S)-2-(2,5-difluorophenyl)-5-oxo-6-(trifluoromethyl)tetrahydro-2H-pyran-3-yl)carbamate (Intermediate 1)

1J (2.3 g, 5.80 mmol) was added to 30 ml N,N-dimethylformamide, and then 4-dimethyl amino pyridine (0.070 g, 0.58 mmol) was added. Under N₂ protection and a condition free of water and oxygen, S-(trifluoromethyl)dibenzothiophenium trifluoromethanesulfonate (2.33 g, 5.80 mmol) was added to the solution, followed by reaction at 0° C. for 2 hours. Water (30 ml) was added to the reaction solution, Which was extracted with ethyl acetate (30 ml×3). The organic layer was washed with saturated sodium chloride, dried over anhydrous sodium sulfate, and concentrated under reduced pressure to dryness. The residue was purified by silica gel column chromatography (petroleum ether/ethyl acetate (v/v)=10:1) to give a yellow solid. The solid was added to 7 ml tetrahydrofuran, and hydrochloric acid (3 ml, 1 mol/l) was added thereto, followed by reaction at room temperature for 3 hours under stirring. The reaction solution was adjusted to pH=7 with a 2 mol/l solution of sodium hydroxide, and extracted with ethyl acetate (30 ml×3). The organic layer was washed with saturated sodium chloride, dried over anhydrous sodium sulfate, concentrated under reduced pressure, and dried by rotary evaporation. The residue was purified by column chromatography (petroleum ether:ethyl acetate (v/v)=8:1) to give Intermediate 1 as a light yellow solid (0.41 g, yield 18%).

MS m/z (ESI):394.0 [M−1];

¹H NMR (400 MHz, DMSO-d₆): δ 7.27 (dd, 4H), 5.20 (q, 1H), 5.07 (d, 1H), 4.13 (dd, 1H), 2.96 (dd, 1H), 2.83 (dd, 1H), 1.26-1.15 (m, 9H).

Intermediate 2: tert-butyl 4,6-dihydro-2-pyrrolo[3,4-c]pyrazole-5-carboxylate (Intermediate 2)

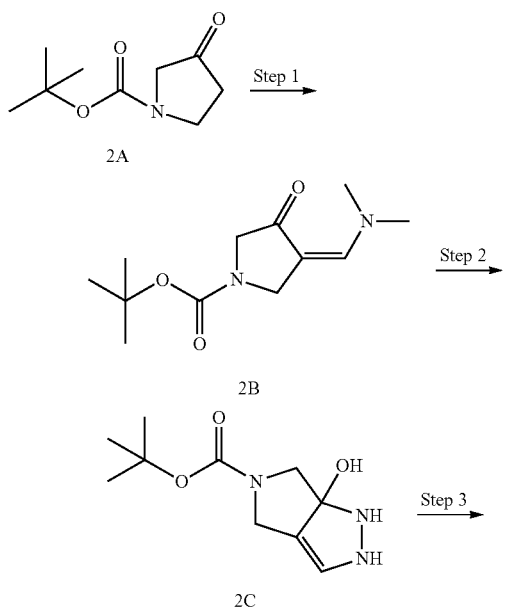

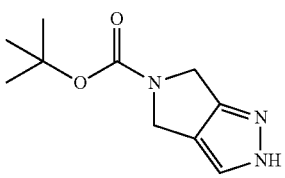

Intermediate 2

Step 1: tert-butyl (3Z)-3-(dimethylaminomethylene)-4-oxo-pyrrolidine-1-carboxylate 1-t-butoxycarbonyl-3-pyrrolidone 2A (100 g, 0.54 mol) was dissolved in N,N-dimethylacetamide (600 ml), N,N-dimethylformamide dimethyl acetal (83.6 g, 0.70 mmol) was added thereto, and the temperature was raised to 105° C., followed by reaction for 40 min under stirring. The reaction was quenched with 500 ml water, and the reaction solution was extracted with ethyl acetate (500 ml×2) and washed with water (500 ml×2). The organic phase was dried over anhydrous sodium sulfate, concentrated, and purified by silica gel column chromatography (petroleum ether/ethyl acetate (v/v)=4:1 to 1:1), to obtain a light yellow liquid 2B (50 g, yield 47%).

Step 2: tert-butyl 6a-hydroxy-1,3a,4,6-tetrahydropyrrolo[3,4-c]pyrazole-5-carboxylate (2C)

2B (50 g, 0.21 mol) was dissolved in methanol (200 ml), and hydrazine hydrate (7.8 g, 0.16 mmol) was added thereto, followed by reaction at room temperature for 4 hours. The organic solvent was dried by rotary evaporation, followed by the next step directly.

Step 3: tert-butyl 4,6-dihydro-2H-pyrrolo[3,4-c]pyrazole-5-carboxylate (Intermediate 2)

2C (47.5 g, 0.21 mol) obtained in the above step was dissolved in a mixed solvent of dichloromethane (300 ml) and methanol (180 ml), and p-toluenesulfonic acid (5.64 g, 0.029 mmol) was added thereto at 0° C., followed by reaction overnight. The solvent was dried by rotary evaporation from the reaction solution, followed by purification by silica gel column chromatography (dichloromethane) to obtain Intermediate 2 (20 g, yield 44%) as a light yellow solid.

¹H NMR (400 MHz, MeOD): δ 7.44 (d, 1H), 4.53-4.33 (m, 4H), 1.54 (s, 9H).

Intermediate 3: tert-butyl ((2R,3S)-2-(2,3,5-trifluorophenyl)-5-oxo-6-(trifluoromethyl)tetrahydro-2H-pyran-3-yl)carbamate (Intermediate 3)

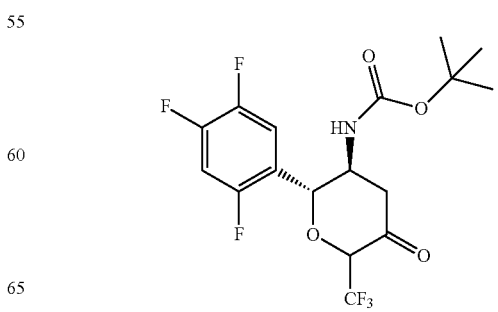

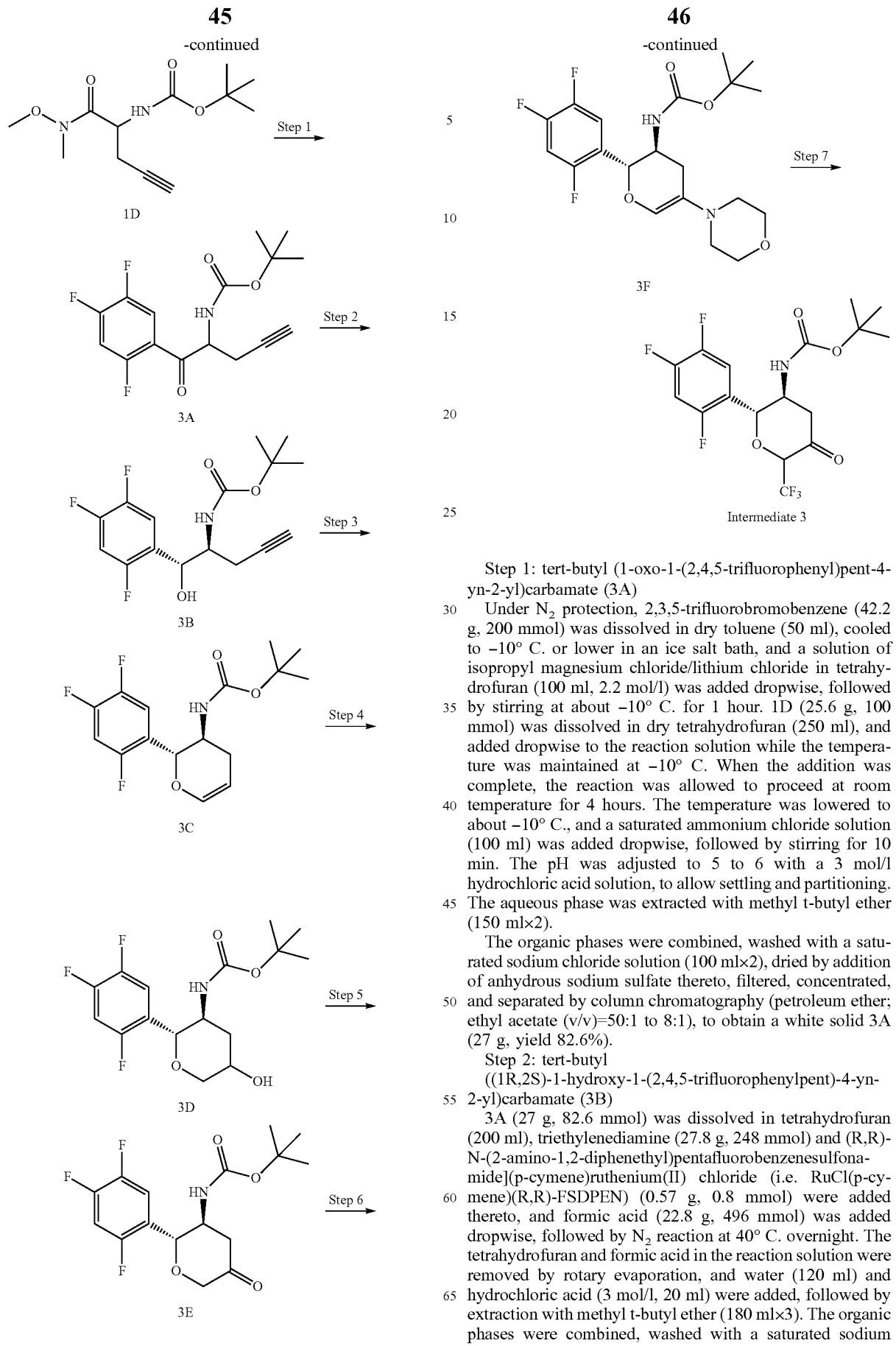

Step 1: tert-butyl (1-oxo-1-(2,4,5-trifluorophenyl)pent-4-yn-2-yl)carbamate (3A)

Under $N_2$ protection, 2,3,5-trifluorobromobenzene (42.2 g, 200 mmol) was dissolved in dry toluene (50 ml), cooled to −10° C. or lower in an ice salt bath, and a solution of isopropyl magnesium chloride/lithium chloride in tetrahydrofuran (100 ml, 2.2 mol/l) was added dropwise, followed by stirring at about −10° C. for 1 hour. 1D (25.6 g, 100 mmol) was dissolved in dry tetrahydrofuran (250 ml), and added dropwise to the reaction solution while the temperature was maintained at −10° C. When the addition was complete, the reaction was allowed to proceed at room temperature for 4 hours. The temperature was lowered to about −10° C., and a saturated ammonium chloride solution (100 ml) was added dropwise, followed by stirring for 10 min. The pH was adjusted to 5 to 6 with a 3 mol/l hydrochloric acid solution, to allow settling and partitioning. The aqueous phase was extracted with methyl t-butyl ether (150 ml×2).

The organic phases were combined, washed with a saturated sodium chloride solution (100 ml×2), dried by addition of anhydrous sodium sulfate thereto, filtered, concentrated, and separated by column chromatography (petroleum ether; ethyl acetate (v/v)=50:1 to 8:1), to obtain a white solid 3A (27 g, yield 82.6%).

Step 2: tert-butyl ((1R,2S)-1-hydroxy-1-(2,4,5-trifluorophenylpent)-4-yn-2-yl)carbamate (3B)

3A (27 g, 82.6 mmol) was dissolved in tetrahydrofuran (200 ml), triethylenediamine (27.8 g, 248 mmol) and (R,R)-N-(2-amino-1,2-diphenethyl)pentafluorobenzenesulfonamide](p-cymene)ruthenium(II) chloride (i.e. RuCl(p-cymene)(R,R)-FSDPEN) (0.57 g, 0.8 mmol) were added thereto, and formic acid (22.8 g, 496 mmol) was added dropwise, followed by $N_2$ reaction at 40° C. overnight. The tetrahydrofuran and formic acid in the reaction solution were removed by rotary evaporation, and water (120 ml) and hydrochloric acid (3 mol/l, 20 ml) were added, followed by extraction with methyl t-butyl ether (180 ml×3). The organic phases were combined, washed with a saturated sodium chloride solution (70 ml×2), dried by addition of anhydrous magnesium sulfate thereto, filtered, concentrated, and separated by column chromatography (petroleum ether/ethyl acetate (v/v)=60:1 to 10:1), to obtain a white solid 3B (23.6 g, yield 87.4%).

Step 3: tert-butyl ((2R,3S)-2-(2,4,5-trifluorophenyl)-3,4-dihydro-2H-pyran-3-yl)carbamate (3C)

3B (23.6 g, 71.7 mmol) was dissolved in N,N-dimethylformamide (250 ml) while being heated, and tetrabutylammonium hexafluorophosphate (3.6 g, 9.3 mmol), N-hydroxy succinimide (4.1 g, 35.8 mmol), triphenylphosphine (1.24 g, 4.73 mmol), and sodium bicarbonate (3.13 g, 37.3 mmol) were added thereto, followed by $N_2$ purging for 3 times and vacuum pumping for 15 min. Then cyclopentadienyl bis (triphenylphosphine)ruthenium(II) chloride (i.e. CpRuCl $(PPh_3)_2$) (2.6 g, 3.58 mmol) was added, followed by $N_2$ purging for 3 times and vacuum pumping for 15 min, Under $N_2$ protection, the temperature was raised to 85° C., followed by reaction overnight. Water (500 ml) and methyl t-butyl ether (300 ml) were added to the reaction solution, which was then filtered through silica gel, and the filtrate was allowed to settle and be partitioned. The aqueous phase was extracted with methyl t-butyl ether (150 ml×2). The organic phases were combined, washed with a saturated sodium bicarbonate solution (100 ml×2), dried by addition of anhydrous sodium sulfate thereto, filtered, concentrated, and separated by column chromatography (petroleum ether/ethyl acetate (v/v)=80:1 to 30:1), to obtain a white powdery solid 3C (9.0 g, yield 38.1%).

Step 4: tert-butyl (2R,3S)-5-hydroxy-2-(2,4,5-trifluorophenyl)tetrahydro-2H-pyran-3-yl)carbamate (3D)

3C (9.0 g, 27.4 mmol) was dissolved in dry methyl t-butyl ether (60 ml), dry toluene (9 ml) was added thereto, the temperature was lowered to −10° C., and a solution of borane dimethyl sulfide in tetrahydrofuran (2 mol/l, 34.2 ml) was added dropwise, followed by reaction at 0° C. for 3.5 hours. Water (4 ml) was added slowly, a sodium hydroxide solution (1 mol/l, 90 ml) was added dropwise, followed by stirring for 15 min, and sodium perborate (12.6 g, 82.2 mmol) was added in batches, followed by stirring at room temperature overnight. The reaction solution was allowed to settle and be partitioned, and the aqueous phase was extracted with methyl t-butyl ether (50 ml×2). The organic phases were combined, washed with a saturated sodium chloride solution (20 ml×2), dried by addition of anhydrous sodium sulfate thereto, filtered, concentrated, followed by addition of toluene (50 ml), and dissolved by heating to 90° C. n-hexane (200 ml) was added dropwise to the reaction solution to precipitate a white solid, followed by filtration. The filter cake was washed with n-hexane (30 ml×2), and concentrated, to obtain a white solid powder 3D (8.6 g, yield 90.5%).

Step 5: tert-butyl ((2R,3S)-5-oxo-2-(2,4,5-trifluorophenyl)tetrahydro-2H-pyran-3-yl)carbamate (3E)

3D (8.6 g, 24.8 mmol) was dissolved in dichloromethane (100 ml), and cooled to 0° C., Dimethyl phthalate (21.1 g, 49.6 mmol) was added in batches to the reaction solution, which was allowed to warm spontaneously to room temperature and undergo reaction for 4 hours. The temperature was lowered to 0° C., and a saturated sodium bicarbonate solution (50 ml) was added dropwise to the reaction solution, followed by stirring for 20 min and filtration. The filtrate was allowed to settle and be partitioned, and the aqueous phase was extracted With methyl t-butyl ether (50 ml×3). The organic phases were combined, washed with a saturated sodium bicarbonate solution (30 ml×2), dried by addition of anhydrous sodium sulfate thereto, filtered, concentrated, and separated by column chromatography (petroleum ether/ethyl acetate (v/v)=10:1 to 4:1), to obtain a white crystalline powder 3E (6.8 g, yield 80%).

MS m/z (ESI):290.1 [M−55].

Step 6: tert-butyl ((2R,3S)-5-morpholino-2-(2,4,5-trifluorophenyl)-3,4-dihydro-2H-pyran-3-yl)carbamate (3F)

3E (6.8 g, 19.7 mmol) was added to 70 ml toluene, morpholine (6.8 g, 78.8 mmol) was added thereto, the reaction solution was heated to 138° C. to reflux while water was separated by a water segregator, and the reaction was allowed to proceed for 6 hours. The reaction solution was cooled to room temperature to precipitate a solid, which was filtered by suction filtration and washed with toluene to obtain a white solid 3F (6.7 g, yield 82%).

MS m/z (ESI):415.1 [M+1].

Step 7: tert-butyl ((2R,3S)-5-oxo-6-(trifluorophenyl)-2-(2,4,5-trifluorophenyl)tetrahydro-2H-pyran-3-yl)carbamate (Intermediate 3)

3F (6.7 g, 16.2 mmol) was added to N,N-dimethylformamide (70 ml), and then 4-dimethyl pyridine (0.19 g, 1.62 mmol) was added. Under $N_2$ protection and a condition free of water and oxygen, S-(trifluoromethyl)dibenzothiophenium trifluoromethanesulfonate (6.5 g, 16.2 mmol) was added to the solution, followed by reaction at 0° C. for 2 hours. Water (200 ml) was added to the reaction solution, which was extracted with ethyl acetate (100 ml×3). The organic layer was washed with saturated sodium chloride, dried over anhydrous sodium sulfate, and concentrated under reduced pressure to dryness. The residue was purified by silica gel column chromatography (petroleum ether/ethyl acetate (v/v)=10:1) to give a yellow solid which was added to 70 ml tetrahydrofuran, and hydrochloric acid (3 ml, 1 mol/l) was added thereto, followed by reaction at room temperature for 3 hours under stirring. The reaction solution was adjusted to pH=7 with a 2 mol/l solution of sodium hydroxide, and extracted with ethyl acetate (30 ml×3). The organic layer was washed with saturated sodium chloride, dried over anhydrous sodium sulfate, concentrated under reduced pressure, and dried by rotary evaporation. The residue was purified by column chromatography (petroleum ether:ethyl acetate (v/v)=8:1) to give Intermediate 3 as a light yellow solid (3.0 g, yield 44%).

$^1$H NMR (400 MHz, DMSO-$d_6$): δ 7.61-7.49 (m, 2H), 7.31 (d, 1H), 5.21-5.17 (m, 1H), 5.05 (d, 1H), 4.17-4.09 (m, 1H), 2.99 (dd, 1H), 2.85 (dd, 1H), 1.22 (s, 9H).

EXAMPLE 1

((2R,3S,5R,6S)-5-(2-(cyclopropylsulfonyl)pyrrolo[3,4-c]pyrazol-5(2H,4H,6H)-yl)-2-(2,5-difluorophenyl)-6-(trifluoromethyl)tetrahydro-2H-pyran-3-amine (Compound 1)

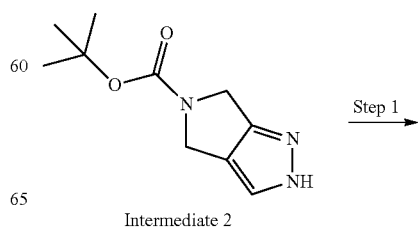

Intermediate 2

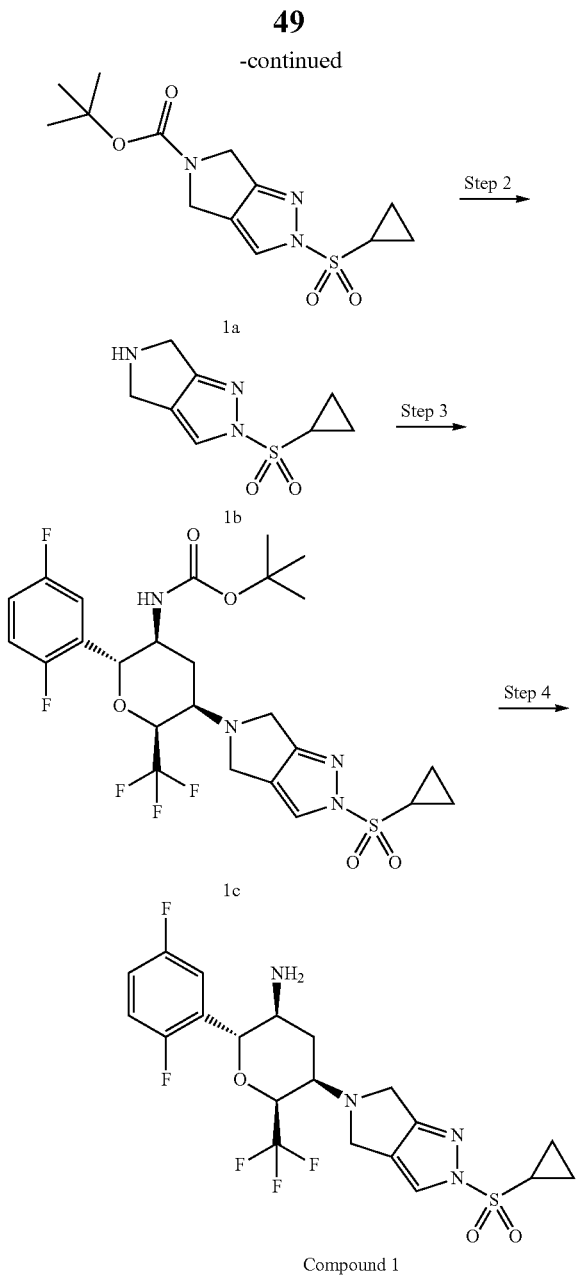

citric acid (1 ml, 15%) was added, and water (10 ml) was added. The solution was extracted with ethyl acetate (20 ml×3). The organic phases were combined, dried over anhydrous sodium sulfate, and concentrated. The residue was purified by silica gel column chromatography (petroleum ether/ethyl acetate (v/v)=2:1) to obtain a white solid 1a (660 mg, yield 73%).

Step 2: 2-(cyclopropylsulfonyl)-2,4,5,6-tetrahydropyrrolo[3,4-c]pyrazole (1b)

1a (645 mg, 2.06 mmol) was dissolved in dichloromethane (8 ml), and trifluoroacetic acid (8 ml) was added thereto, followed by reaction at room temperature for 2 hours. The reaction solution was dried by rotary evaporation, and the reaction was quenched by addition of aqueous ammonia (1 ml), followed by purification by silica gel column chromatography (dichloromethane/methanol (v/v)=10:1) to obtain a light yellow solid 1b (400 mg, yield 91%).

$^1$H NMR (400 MHz, MeOD): δ 7.85 (s, 1H), 4.01-3.94 (m, 4H), 3.36 (s, 3H).

Step 3: tert-butyl ((2R,3S,5R,6S)-5-(2-(cyclopropylsulfonyl)pyrrolo[3,4-c]pyrazol-5(2H,4H,6H)-yl)-2-(2,5-difluorophenyl)-6-(trifluoromethyl)tetrahydro-2H-pyran-3-carbamate (1c)

Intermediate 1 (305 mg, 0.77 mmol) and 2-(cyclopropylsulfonyl-2,4,5,6-tetrahydropyrrolo[3,4-c]pyrazole (1b) (197 mg, 0.93 mmol) were added to 5 ml toluene, and the reaction was allowed to proceed in an open reaction vessel in a 140° C. oil bath until the solvent was evaporated to dryness. In a $N_2$ atmosphere, the residue was cooled to room temperature and re-dissolved in 1,2-dichloroethane (10 ml), and tri(acetoxy)sodium borohydride (650 ml, 3.08 mmol) and acetic acid (92.5 mg, 1.54 mmol) were added sequentially, followed by reaction at room temperature for 3 hours. The reaction was quenched by addition of a saturated sodium bicarbonate solution (1.5 ml) to the reaction solution, which was allowed to be partitioned. The aqueous phase was extracted with ethyl acetate (15 mL×3). The organic phases were combined, dried over anhydrous sodium sulfate, and concentrated. The concentrate was purified by silica gel column chromatography (petroleum ether/ethyl acetate (v/v)=4:1) to obtain a white foamy solid 1e (190 mg, yield 42%).

Step 4: ((2R,3S,5R,6S)-5-(2-(cyclopropylsulfonyl)pyrrolo[3,4-c]pyrazol-5(2H,4H,6H)-yl)-2-(2,5-difluorophenyl)-6-(trifluoromethyl)tetrahydro-2H-pyran-3-amine (Compound 1)

1c (190 mg, 0.32 mmol) was dissolved in dichloromethane (4.5 ml) and trifluoroacetic acid (1.5 ml), followed by stirring at room temperature for 1 hour. The reaction was quenched by addition of a saturated sodium bicarbonate solution (10 ml) to the reaction solution, which was allowed to be partitioned. The aqueous phase was extracted with ethyl acetate (15 ml×2). The organic phases were combined, dried over anhydrous sodium sulfate, and concentrated. The concentrate was purified by silica gel column chromatography (dichloromethane/methanol (v/v)=50:1) to obtain Compound 1 as a white powdery solid (126 mg, yield 80%).

MS m/z (ESI):493.1[M+1];

$^1$H NMR (400 MHz, DMSO-$d_6$) δ 7.98 (m, 1H), 7.27 (m, 3H), 4.81-4.68 (qd, 1H), 4.50 (d, 1H), 3.94 (dd, 2H), 3.78 (dd, 2H), 3.46 (m, 1H), 3.11-3.04 (m, 1H), 3.03-2.94 (ddd, 1H), 2.37-2.26 (m, 1H), 1.83 (m, 1H), 1.28-1.21 (m, 4H).

Figure 2:
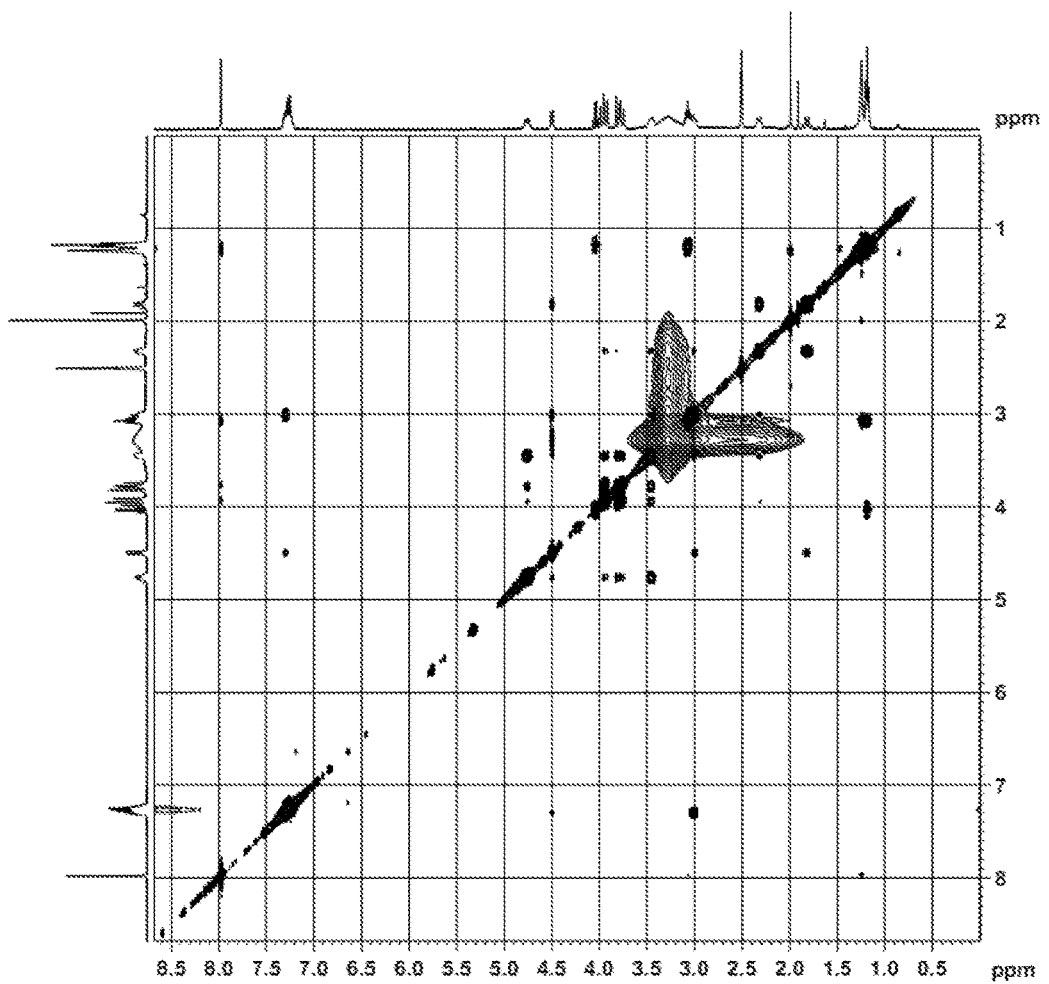
FIG. 2 is the $^1$H-$^1$H NOESY spectrum of Compound 1.
Figure 3:
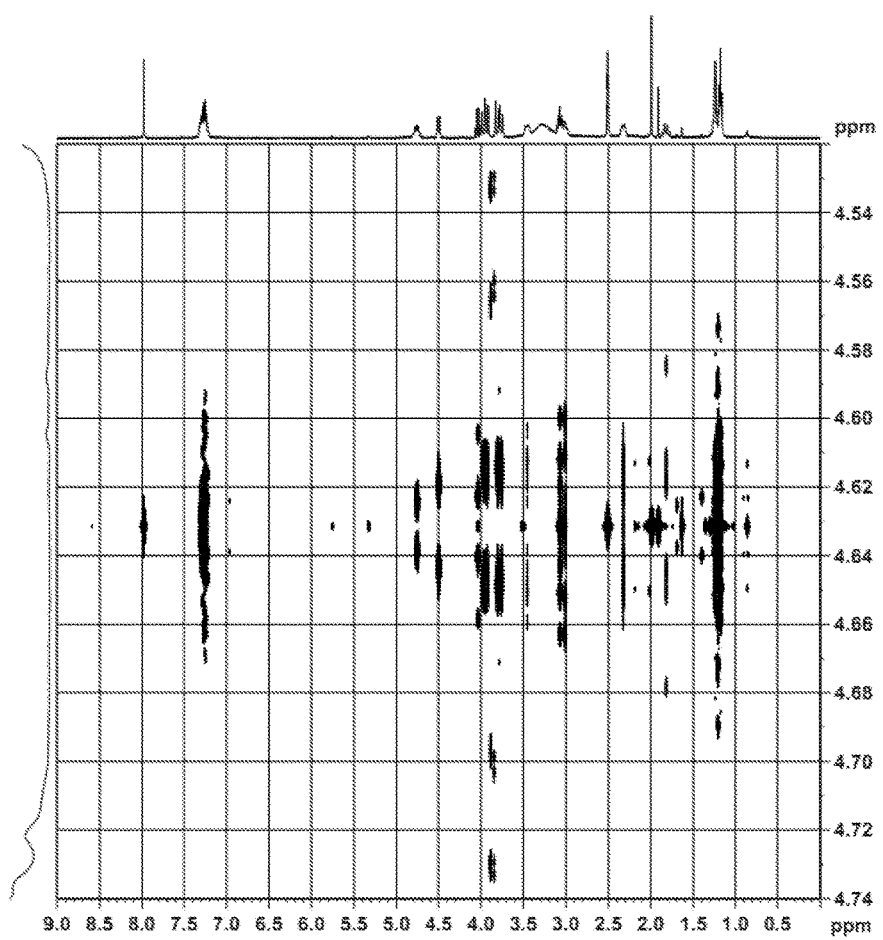
FIG. 3 is the $^1$H-$^1$H J-resolved spectrum of Compound 1.

The $^1$H-$^1$H COSY, $^1$H-$^1$H NOESY and $^1$H-$^1$H J-resolved spectra of Compound 1 are shown in FIGS. 1-3, and the data are shown in Table 1, demonstrating that Compound 1 has the following configuration:

Step 1: tert-butyl 2-(cyclopropylsulfonyl-4,6-dihydropyrrolo[3,4-c]pyrazole-5(2H)-carboxylate (1a)

Under $N_2$ protection and a condition free of water and oxygen, Intermediate 2 (604 mg, 2.87 mmol) was dissolved in tetrahydrofuran (20 ml), which was cooled to 0° C. and sodium hydride (180 mg, 60 wt %, 4.5 mmol) was added, followed by stirring for 30 min. Cyclopropylsulfonyl chloride (1.27 g, 9.0 mmol) was added dropwise, and the temperature was allowed to rise spontaneously to room temperature, followed by reaction for 1 hour. The reaction was quenched by addition of water (20 ml) to the reaction solution, which was then extracted with ethyl acetate (20 ml×2). The organic phases were combined, dried over anhydrous sodium sulfate, concentrated, re-dissolved in 5 ml tetrahydrofuran, and cooled to −10° C. to 0° C. Potassium t-butoxide (36 mg, 0.32 mmol) was added, and the reaction was allowed to proceed for 28 hours at this temperature. After the reaction was completed, an aqueous solution of

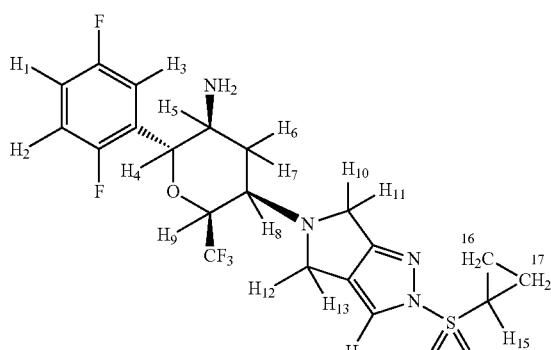

TABLE 1

Data of the ¹H NMR, ¹H-¹H COSY, and
¹H-¹H NOESY of Compound 1 (DMSO-d6, 400 MHz)

| | Shift | Multiplet | COSY | NOESY |
|---|---|---|---|---|
| H1, H2, H3 | 7.27 | m | — | H4, H5 |
| H4 | 4.50 | d(9.38 Hz*) | H5 | H3, H7, NH₂** |
| H5 | 3.02 | ddd(12.79, 9.38, 4.49 Hz*) | H4, H6, H7 | H3, H8 |
| H6 | 2.33 | m | H5, H7, H8 | — |
| H7 | 1.83 | m | H5, H6, H8 | H4 |
| H8 | 3.46 | m | H6, H7, H9 | H5, H10, H11 H12, H13 |
| H9 | 4.77 | qd(5.83 Hz*) | H8 | H10, H11 H12, H13 |
| H10, H11 H12, H13 | 3.87 | m | H10, H11 H12, H13, H14 | H8, H9 |
| H14 | 7.98 | m | H10, H11 H12, H13 | H15 16-CH₂, 17-CH₂ |
| H15 | 3.07 | m | 16-CH₂, 17-CH₂ | H14 |
| 16-CH₂, 17-CH₂ | 1.22 | m | H15 | H14 |

*Read from ¹H-¹H J-resolved spectra.
**NH₂ proton exchanged with the water peak.

EXAMPLE 2

(2R,3S,5R,6S)-2-(2,5-difluorophenyl)-5-(2-(ethylsulfonyl)pyrrolo[3,4-c]pyrazol-5(2H, 4H,6H)-yl)-6-(trifluoromethyl)tetrahydro-2H-pyran-3-amine (Compound 2)

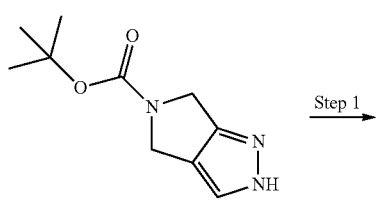

Intermediate 2

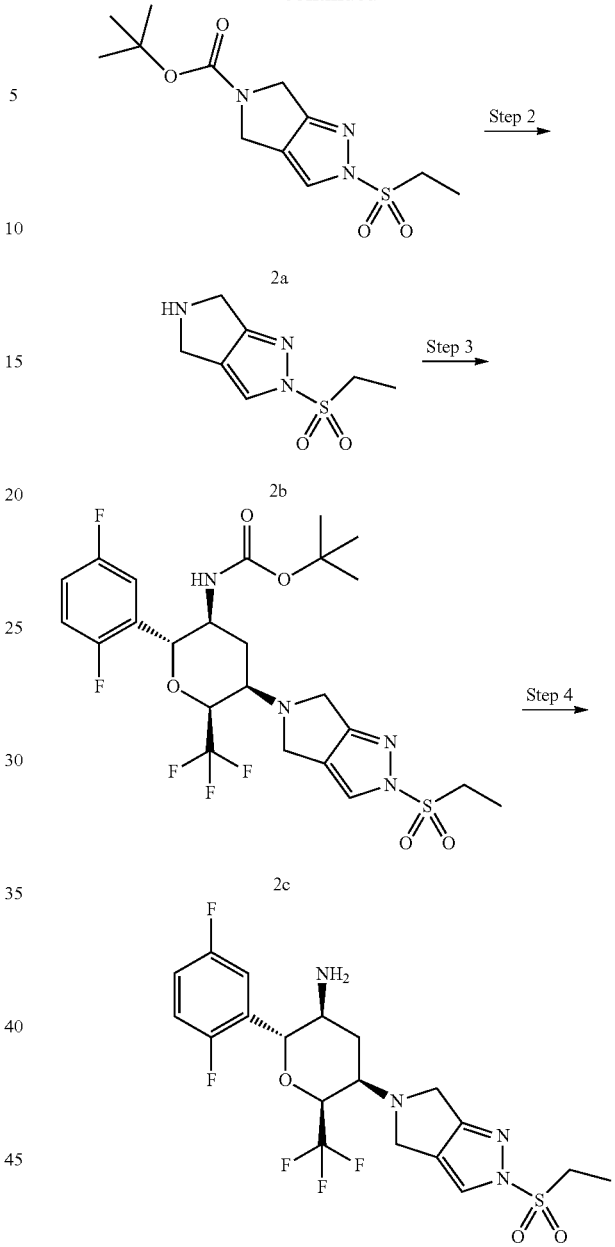

Step 1: tert-butyl 2-(ethylsulfonyl)-4,6-dihydropyrrolo[3,4-c]pyrazole-5(2H)-carboxylate (2a)

Under N₂ protection and a condition free of water and oxygen, Intermediate 2 (627 mg, 3.0 mmol) was dissolved in tetrahydrofuran (20 ml), which was cooled to 0° C., and sodium hydride (180 mg, 60 wt %, 4.5 mmol) was added, followed by stirring for 30 min. Ethylsulfonyl chloride (1.16 g, 9.0 mmol) was added dropwise, and the temperature was allowed to rise spontaneously to room temperature, followed by reaction for 1 hour. The reaction was quenched by addition of water (20 ml) to the reaction solution, which was then extracted with ethyl acetate (20 ml×2). The organic layers were combined, dried over anhydrous sodium sulfate, concentrated, re-dissolved in tetrahydrofuran (5 ml), and cooled to −10° C. to 0° C. Potassium t-butoxide (35 mg, 0.31 mmol) was added, and the reaction was allowed to proceed for 24 hours at this temperature. After the reaction was completed, a saturated aqueous solution of ammonium chloride (10 ml) and water (10 ml) were added. The solution was extracted with ethyl acetate (20 ml×3). The organic layers were combined, dried over anhydrous sodium sulfate, and concentrated. The residue was purified by silica gel column chromatography (petroleum ether/ethyl acetate (v/v) 5:1) to obtain a white solid 2a (730 mg, yield 81%).

Step 2: 2-(ethylsulfonyl)-2,4,5,6-tetrahydropyrrolo[3,4-c]pyrazole (2b)

2a (710 mg, 2.36 mmol) was dissolved in dichloromethane (8 ml), and trifluoroacetic acid (8 ml) was added thereto, followed by reaction at room temperature for 2 hours. The reaction solution was dried by rotary evaporation, and the reaction was quenched by addition of aqueous ammonia (1 ml), followed by purification by silica gel column chromatography (dichloromethane/methanol (v/v)=10:1) to obtain a light yellow solid 2b (460 mg, yield 97%).

Step 3: tert-butyl ((2R,3S,5R,6S)-2-(2,5-difluorophenyl)-5-(2-(ethylsulfonyl)pyrrolo[3,4-c]pyrazol-5(2H,4H,6H)-yl)-6-(trifluoromethyl)tetrahydro-2H-pyran-3yl)carbamate (2c)

Intermediate 1 (350 mg, 0.89 mmol) and 2-(ethylsulfonyl)-2,4,5,6-tetrahydropyrrolo[3,4-c]pyrazole (2b) (244 mg, 1.21 mmol) were added to toluene (5 ml), and the reaction was allowed to proceed in an open round-bottom flask in a 140° C. oil bath until the solvent was evaporated to dryness. In a $N_2$ atmosphere, the residue was cooled to room temperature, and re-dissolved in 1,2-dichloroethane (10 ml). In a $N_2$ atmosphere, tri(acetoxy)sodium borohydride (854 mg, 4.04 mmol) and acetic acid (0.115 ml, 2.02 mmol) were added sequentially, followed by reaction at room temperature for 3 hours. The reaction was quenched by addition of a saturated sodium bicarbonate solution (15 ml) to the reaction solution, which was allowed to be partitioned. The aqueous phase was extracted with ethyl acetate (15 ml×3). The organic phases were combined, dried over anhydrous sodium sulfate, and concentrated. The concentrate was purified by silica gel column chromatography (petroleum ether/ethyl acetate (v/v)=5:1) to obtain a white foamy solid 2c (220 mg, yield 38%).

Step 4:
((2R,3S,5R,6S)-2-(2,5-difluorophenyl)-5-(2-(ethylsulfonyl)pyrrolo[3,4-c]pyrazol-5(2H,4H,6H)-yl)-6-(trifluoromethyl)tetrahydro-2H-pyran-3-amine (Compound 2)

2c (220 mg, 0.38 mmol) was dissolved in dichloromethane (4.5 ml) and trifluoroacetic acid (1.5 ml), followed by stirring at room temperature for 1 hour. The reaction was quenched by addition of a saturated sodium bicarbonate solution (10 ml) to the reaction solution, which was allowed to be partitioned. The aqueous phase was extracted with ethyl acetate (15 ml×2), The organic phases were combined, dried over anhydrous sodium sulfate, and concentrated. The concentrate was purified by silica gel column chromatography (dichloromethane/methanol (v/v)=50:1) to obtain Compound 2 as a white powdery solid (60 mg, yield 33%).

MS m/z (ESI):481.1 [M+1];

$^1$H NMR (400 MHz, DMSO-$d_6$) δ 7.98 (m, 1H), 7.33-7.22 (m, 3H), 4.88-4.71 (qd, 1H), 4.51 (d, 1H), 3.95 (dd, 2H), 3.78 (dd, 2H), 3.64 (q, 2H), 3.49-3.43 (m, 3.05-2.97 (ddd, 1H), 2.35-2.29 (m, 1H), 1.82 (m, 1H), 1.12 (t, 3H).

Figure 4:
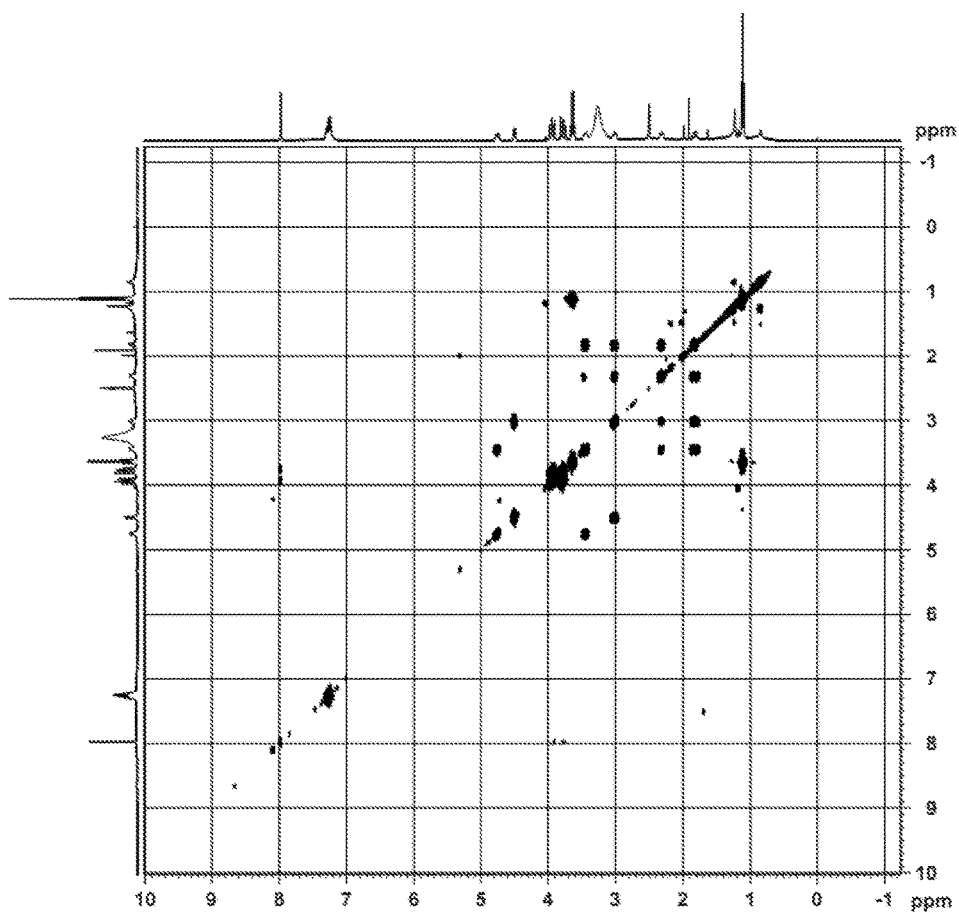
FIG. 4 is the $^1$H-$^1$H COSY spectrum of Compound 2.
Figure 5:
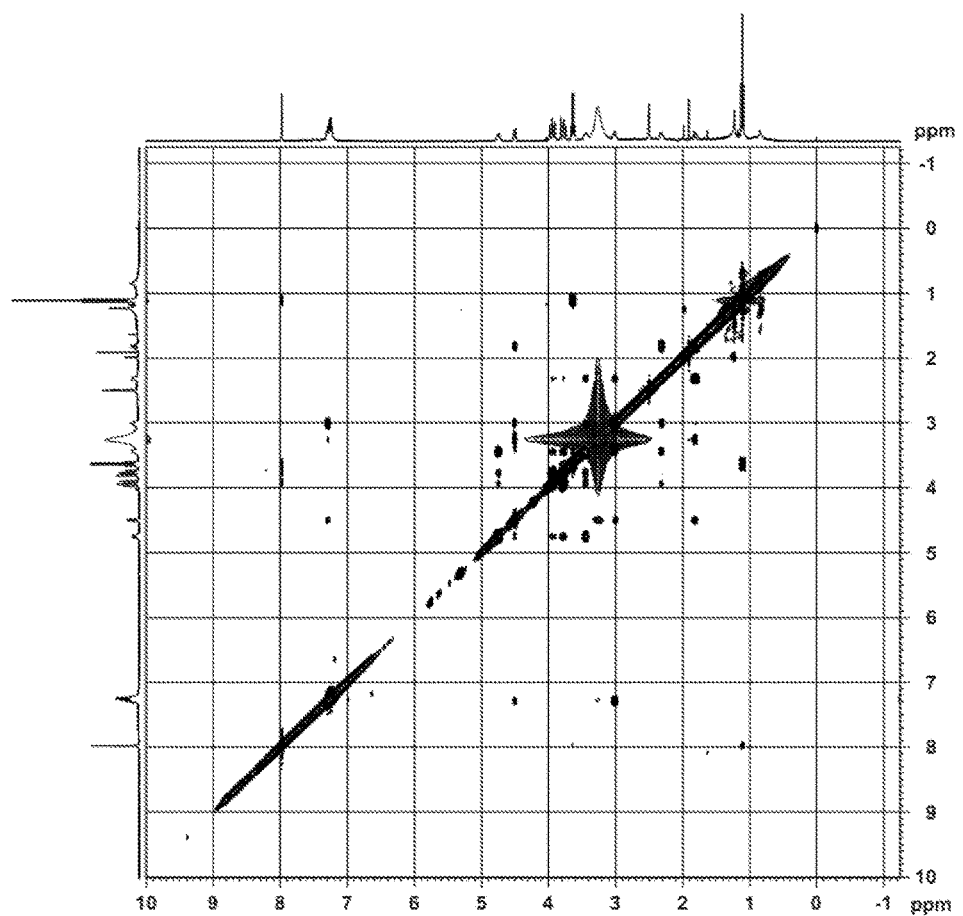
FIG. 5 is the $^1$H-$^1$H NOESY spectrum of Compound 2.
Figure 6:
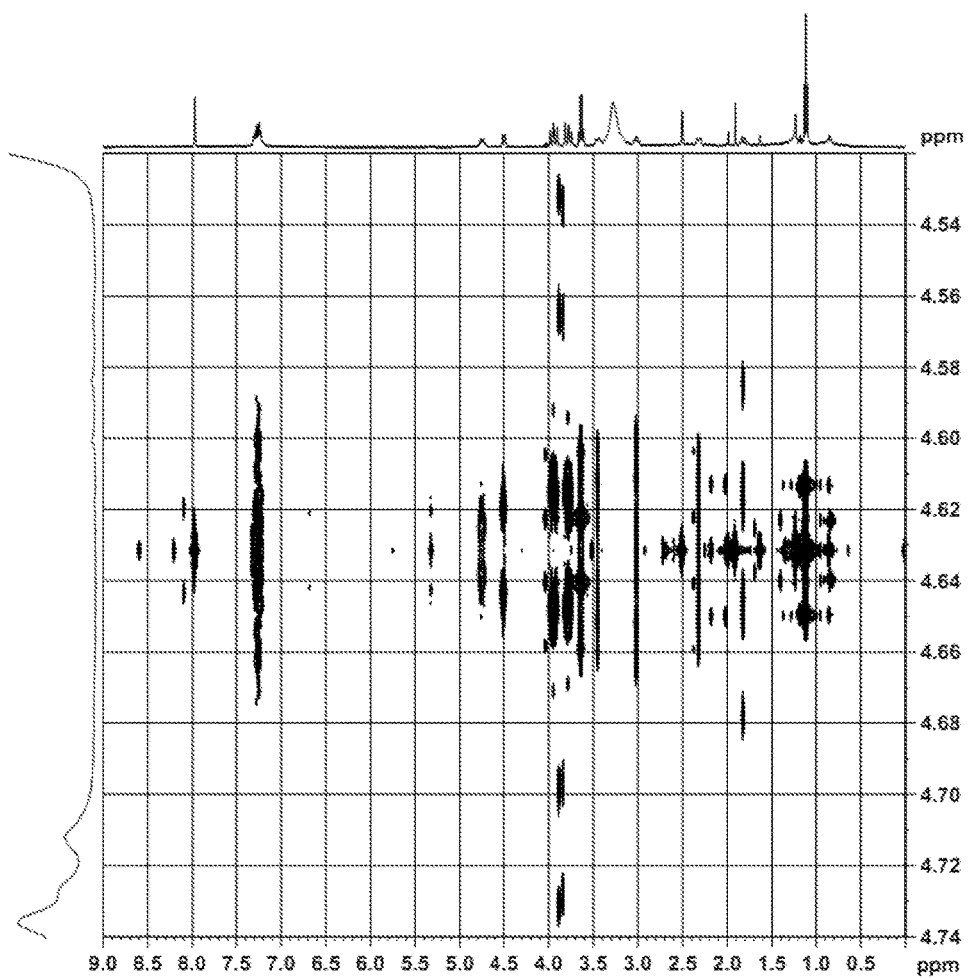
FIG. 6 is the $^1$H-$^1$H J-resolved spectrum of Compound 2.

The $^1$H-$^1$H COSY, $^1$H-$^1$H NOESY and $^1$H-$^1$H J-resolved spectra of Compound 2 are shown in FIGS. 4-6, and the data are shown in Table 2, demonstrating that Compound 2 has the following configuration:

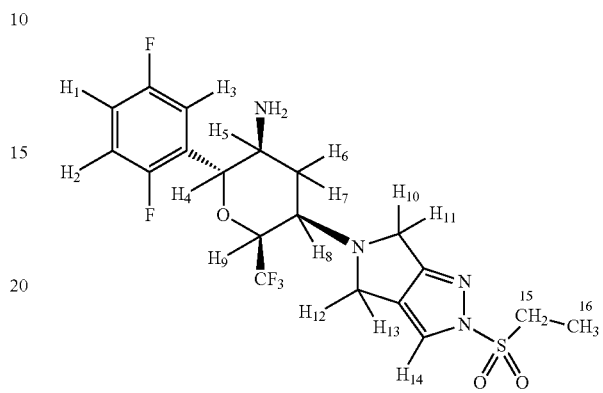

TABLE 2

Data of the $^1$H NMR, $^1$H-$^1$H COSY, and
$^1$H-$^1$H NOESY of Compound 2 (DMSO-$d_6$, 400 MHz)

| | Shift | Multiplet | COSY | NOESY |
|---|---|---|---|---|
| H1, H2, H3 | 7.26 | m | — | H4, H5 |
| H4 | 4.51 | d(9.79 Hz*) | H5 | H7, NH$_2$** |
| H5 | 3.02 | ddd(12.93, 9.79, 4.33 Hz*) | H4, H6, H7 | H3, H8 |
| H6 | 2.32 | m | H5, H7, H8 | H10, H11 H12, H13 |
| H7 | 1.82 | m | H5, H6, H8 | H4, NH$_2$** |
| H8 | 3.45 | m | H6, H7, H9 | H5, H10, H11 H12, H13 |
| H9 | 4.85 | qd(5.50 Hz*) | H8 | H10, H11 H12, H13 |
| H10, H11 H12, H13 | 3.86 | m | H10, H11 H12, H13, H14 | H6, H8, H9, NH2** |
| H14 | 7.98 | m | H10, H11 H12, H13 | 15-CH$_2$, 16-CH$_3$ |
| 15-CH$_2$ | 3.64 | q(7.25 Hz*) | 16-CH$_3$ | H14 |
| 16-CH$_3$ | 1.12 | t(7.25 Hz*) | 15-CH$_2$ | H14 |

*Read from $^1$H-$^1$H J-resolved spectra.

**NH$_2$ proton exchanged with the water peak.

EXAMPLE 3

(2R,3S,5R,6S)-2-(2,5-difluorophenyl)-5-(2-(methylsulfonyl)pyrrolo[3,4-c]pyrazol-5(2H,4H,6H)-yl)-6-(trifluoromethyl)tetrahydro-2H-pyran-3-amine (Compound 3)

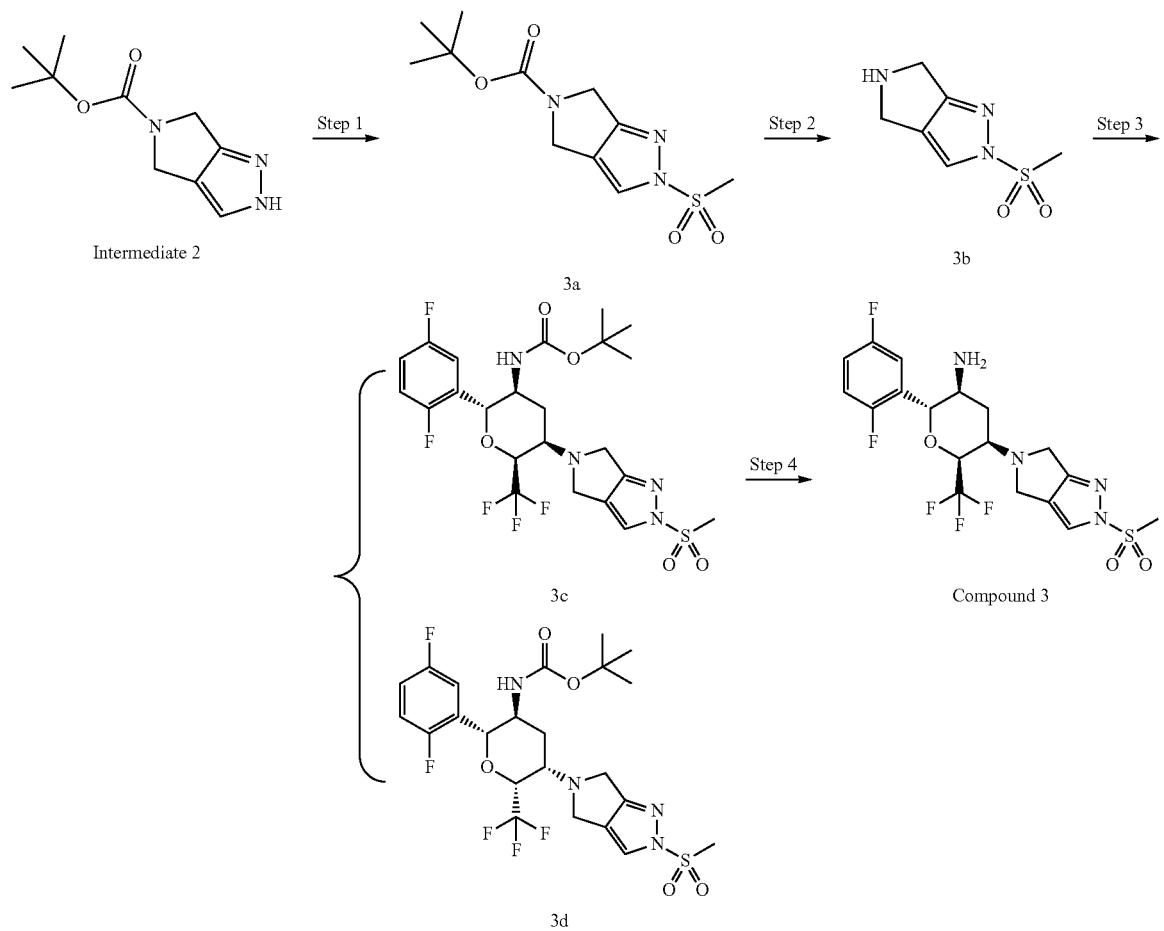

Step 1: tert-butyl 2-methylsulfonyl-4,6-dihydropyrrolo[3,4-c]pyrazole-5-carboxylate (3a)

Intermediate 2 (3.5 g, 16.7 mmol) was dissolved in tetrahydrofuran (35 ml), and sodium hydride (1.0 g, 60%, 25.4 mmol) was added at 0° C., followed by reaction for 30 min. Methylsulfonyl chloride (2.9 g, 25.4 mmol) was added, followed by reaction for 1 hour. The reaction was quenched by addition of water (10 ml) to the reaction solution, which was extracted with ethyl acetate (50 ml×2). The organic layers were combined, dried over anhydrous sodium sulfate, concentrated, and purified by silica gel column chromatography (petroleum ether/ethyl acetate (v/v)=1:1), to obtain a white solid 3a (2.1 g, yield 44%).

Step 2: 2-methylsulfonyl-5,6-dihydro-4H-pyrrolo[3,4-c]pyrazole (3b)

3a (2.1 g, 7.3 mmol) was dissolved in dichloromethane (25 ml), and trifluoroacetic acid (5 ml) was added thereto at 0° C., followed by reaction at 0° C. for 2 hours. The reaction solution was dried by rotary evaporation, and the reaction was quenched by addition of aqueous ammonia (2 ml), followed by purification by silica gel column chromatography (dichloromethane/methanol (v/v)=50:1) to obtain a white solid 3b (1.1 g, yield 80.5%).

$^1$H NMR (400 MHz, MeOD): δ 7.85 (s, 1H), 4.01-3.94 (m, 4H), 3.36 (s, 3H).

Step 3: tert-butyl (2R,3S,5R,6S)-2-(2,5-difluorophenyl)-5-(2-(methylsulfonyl)pyrrolo[3,4-c]pyrazol-5(2H,4H,6H)-yl)-6-(trifluoromethyl)tetrahydro-2H-pyran-3-yl)carbamate (3c)

Intermediate 1 (490 mg, 1.24 mmol) and 3b (254 mg, 1.36 mmol) were added to 10 ml toluene, and the reaction was allowed to proceed in an open round-bottom flask in a 140° C. oil bath until the solvent was evaporated to dryness. In a $N_2$ atmosphere, the residue was cooled to room temperature and re-dissolved in 1,2-dichloroethane (15 ml), and tri(acetoxy)sodium borohydride (1.05 mg, 4.96 mmol) and acetic acid (149 mg, 2.48 mmol) were added sequentially, followed by reaction at room temperature for 3 hours. The reaction was quenched by addition of a saturated sodium bicarbonate solution (20 ml) to the reaction solution, which was allowed to be partitioned. The aqueous phase was extracted with ethyl acetate (20 ml×2). The organic phases were combined, dried over anhydrous sodium sulfate, and concentrated. The concentrate was purified by silica gel column chromatography (petroleum ether/ethyl acetate (v/v)=3:1) to obtain a white oily liquid 3c (455 mg, yield 60%) and a white solid 3d (45 mg, yield 5.9%).

Step 4:

(2R,3S,5R,6S)-2-(2,5-difluorophenyl)-5-(2-(methylsulfonyl)pyrrolo[3,4-c]pyrazol-5(2H,4H,6H)-yl)-6-(trifluoromethyl)tetrahydro-2H-pyran-3-amine (Compound 3)

3c (410 mg, 0.72 mmol) was dissolved in 6 ml dichloromethane and 2 ml trifluoroacetic acid, followed by stirring at room temperature for 1 hour. The reaction was quenched by addition of a saturated sodium bicarbonate solution (30 ml) to the reaction solution, which was allowed to be partitioned. The aqueous phase was then extracted with ethyl acetate (30 mL×2). The organic phases were combined, dried over anhydrous sodium sulfate, and concentrated. The concentrate was purified by silica gel column chromatography (dichloromethane/methanol (v/v)=30:1) to obtain Compound 3 as a white powdery solid (250 mg, yield 75%).

MS m/z (ESI): 467.1[M+1];

$^1$H NMR (400 MHz, DMSO-$_6$): δ 7.96 (m, 1H), 7.35-7.04 (m, 3H), 4.86-4.63 (qd, 1H), 4.50 (d, 1H), 3.95 (dd, 2H), 3.78 (dd, 2H), 3.49 (s, 3H), 3.45 (m, 1H), 3.00 (ddd, 1H), 2.33 (m, 1H), 1.82 (m, 1H), 1.48 (br, 2H).

Figure 7:
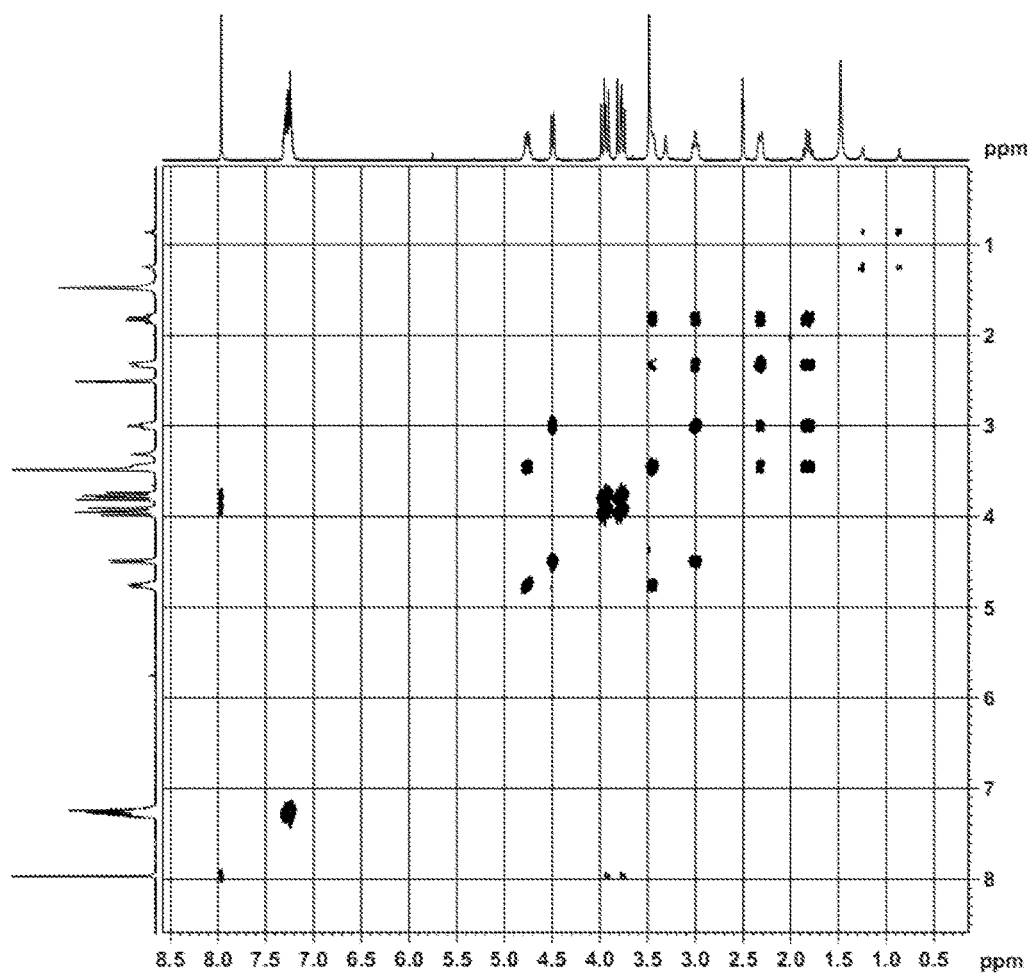
FIG. 7 is the $^1$H-$^1$H COSY spectrum of Compound 3.
Figure 8:
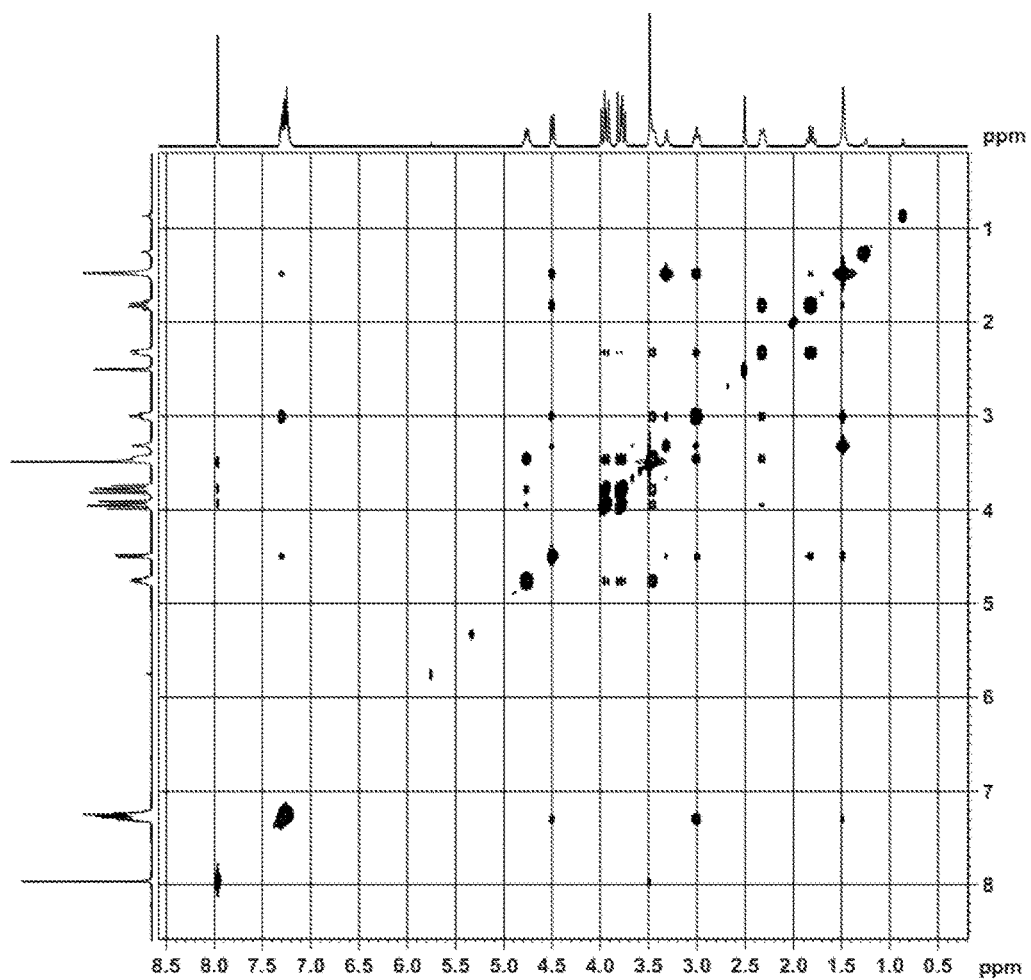
FIG. 8 is the $^1$H-$^1$H NOESY spectrum of Compound 3.
Figure 9:
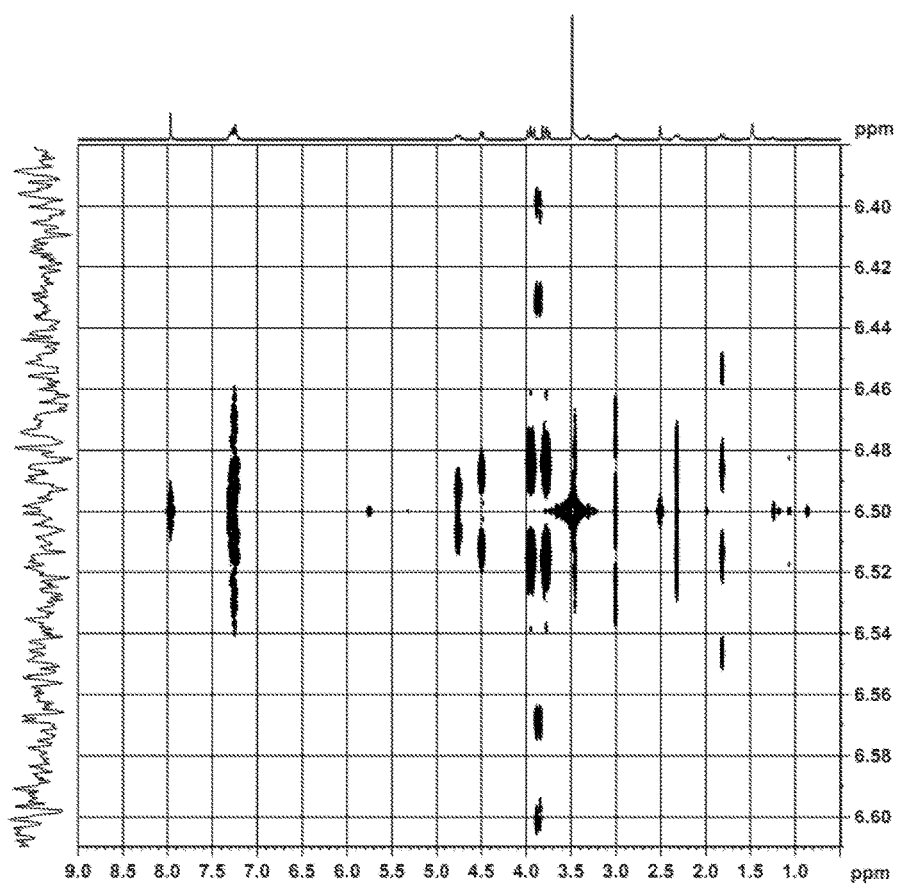
FIG. 9 is the $^1$H-$^1$H J-resolved spectrum of Compound 3.

The $^1$H-1H COSY, $^1$H-$^1$H NOESY and $^1$H-$^1$H J-resolved spectra of Compound 3 are shown in FIGS. 7-9, and the data are shown in Table 3, demonstrating that Compound 3 has the following configuration:

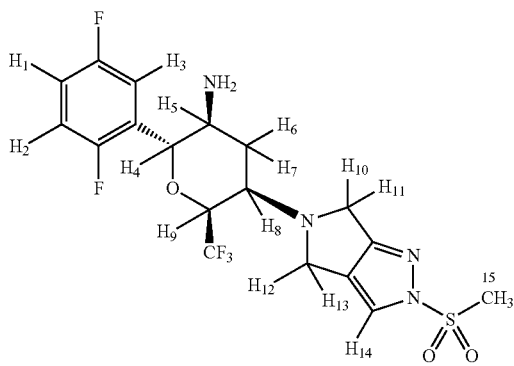

TABLE 3

Data of the $^1$H NMR, $^1$H-$^1$H COSY, and $^1$H-$^1$H NOESY of Compound 3 (DMSO-d$_6$, 400 MHz)

| | Shift | Multiplet | COSY | NOESY |
|---|---|---|---|---|
| —NH$_2$ | 1.48 | br | — | H3, H4, H5, H6, H7 |
| H1, H2, H3 | 7.27 | m | — | H4, H5, H9, —NH$_2$, |
| H4 | 4.50 | d(9.72 Hz*) | H5 | H3, H7, —NH$_2$, NH$_2$** |
| H5 | 3.00 | ddd(13.08, 9.72, 4.50 Hz*) | H4, H6, H7 | H3, H8, NH$_2$** |
| H6 | 2.33 | m | H5, H7, H8 | H10, H11, H12, H13 |
| H7 | 1.82 | m | H5, H6, H8 | H4, —NH2 |
| H8 | 3.45 | m | H6, H7, H9 | H5, H10, H11, H12, H13, |
| H9 | 4.76 | qd(5.75 Hz*) | H8 | H3, H10, H11 H12, H13 |
| H10, H11 H12, H13 | 3.87 | m | H10, H11 H12, H13, H14 | H6, H8, H9 |
| H14 | 7.96 | m | H10, H11 H12, H13 | H15 |
| 15-CH$_3$ | 3.49 | s | — | H14 |

*Read from $^1$H-$^1$H J-resolved spectra.
**NH$_2$ proton exchanged with the water peak.

EXAMPLE 4

(2R,3S,5R,6S)-5-(2-(methylsulfonyl)pyrrolo[3,4-c]pyrazol-5(2H,4H,6H)-yl)-6-(trifluoromethyl)-2-(2,4,5-trifluorophenyl)tetrahydro-2H-pyran-3-amine (Compound 4)

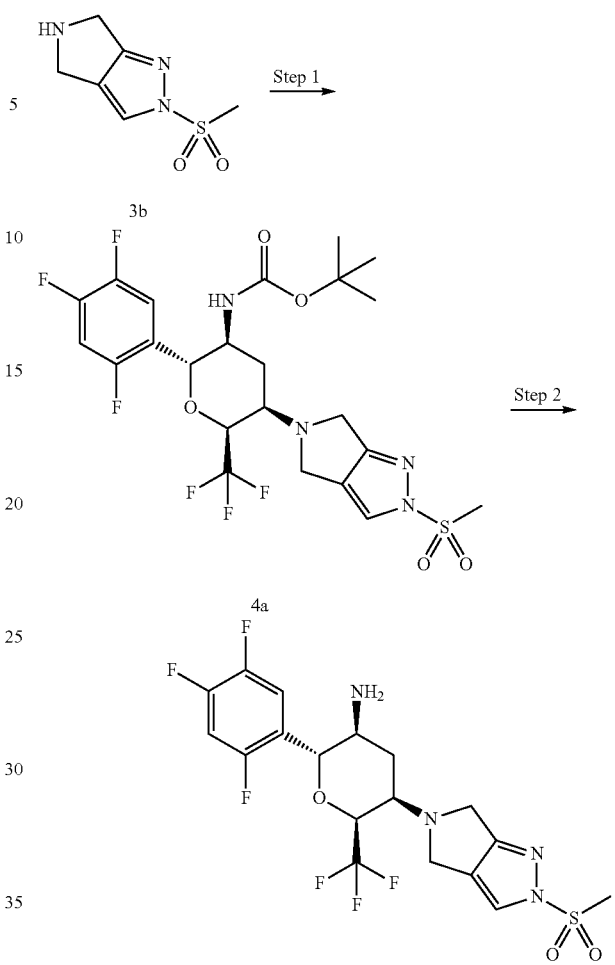

Step 1: tert-butyl ((2R,3S,5R,6S)-5-(2-(methylsulfonyl)pyrrolo[3,4-c]pyrazol-5(2H,4H,6H)-yl)-6-(trifluoromethyl)-2-(2,4,5-trifluorophenyl)tetrahydro-2H-pyran-3-yl)carbamate (4a)

Intermediate 3 (3 g, 7.26 mmol) and 3b (1.76 g, 9.44 mmol) were added to 100 ml toluene, and the reaction was allowed to proceed in an open round-bottom flask in a 140° C. oil bath until the solvent was evaporated to dryness. In a N$_2$ atmosphere, the residue was cooled to room temperature and re-dissolved in 1,2-dichloroethane (30 ml), and tri (acetoxy)sodium borohydride (4.62 g, 21.8 mmol) and acetic acid (0.87 g, 14.5 mmol) were added sequentially, followed by reaction at room temperature for 3 hours. The reaction was quenched by addition of a saturated sodium bicarbonate solution (30 ml) to the reaction solution, which was allowed to be partitioned. The aqueous phase was extracted with ethyl acetate (30 mL×2). The organic phases were combined, dried over anhydrous sodium sulfate, and concentrated. The concentrate was purified by silica gel column chromatography (petroleum ether/ethyl acetate (v/v)=3:1) to obtain a white oily liquid 4a (1.3 g, yield 30.6%).

Step 2: (2R,3S,5R,6S)-5-(2-(methylsulfonyl)pyrrolo[3,4-c]pyrazol-5(2H,4H,6H)-yl)-6-(trifluoromethyl)-2-(2,4,5-trifluorophenyl)tetrahydro-2H-pyran-3-amine (Compound 4)

4a (1.3 g, 2.44 mmol) was dissolved in dichloromethane (7.8 ml) and trifluoroacetic acid (2.6 ml), followed by stirring at room temperature for 1 hour. The reaction was quenched by addition of a saturated sodium bicarbonate solution (30 ml) to the reaction solution, which was allowed to be partitioned. The aqueous phase was extracted with ethyl acetate (30 mL×2). The organic phases were combined, dried over anhydrous sodium sulfate, and concentrated. The concentrate was purified by silica gel column chromatography (dichloromethane/methanol (v/v)=30:1) to obtain Compound 4 as a white powdery solid (700 mg, yield 65%).

MS m/z (ESI): 485.0[M+1];

$^1$H NMR (400 MHz, DMSO-d$_6$): δ 7.97 (s, 1H), 7.58-7.53 (m, 2H), 4.78-4.74 (m, 1H), 4.47 (d, 1H), 3.98-3.91 (m., 2H), 3.81-3.73 (m, 2H), 3.49 (s, 3H), 3.46-3.43 (m, 1H), 2.99 (m, 1H), 2.33 (m, 1H), 1.82 (q, 1H), 1.50 (s, 2H).

EXAMPLE 5

(2R,3S,5R,6S)-2-(2,5-difluorophenyl)-5-(2-(((tetrahydrofuran-3-yl)sulfonyl)pyrrolo[3,4-c]pyrazol-5(2H,4H,6H)-yl)-6-(trifluoromethyl)tetrahydro-2H-pyran-3-amine (Compound 5)

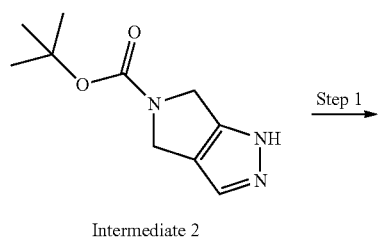

Intermediate 2

Step 1

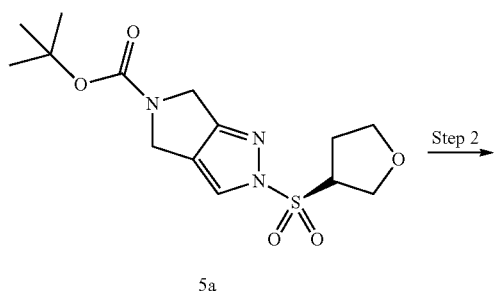

5a

Step 2

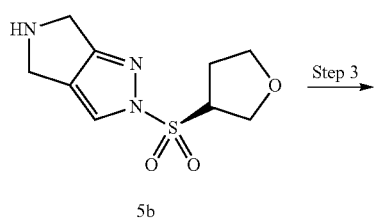

5b

Step 3

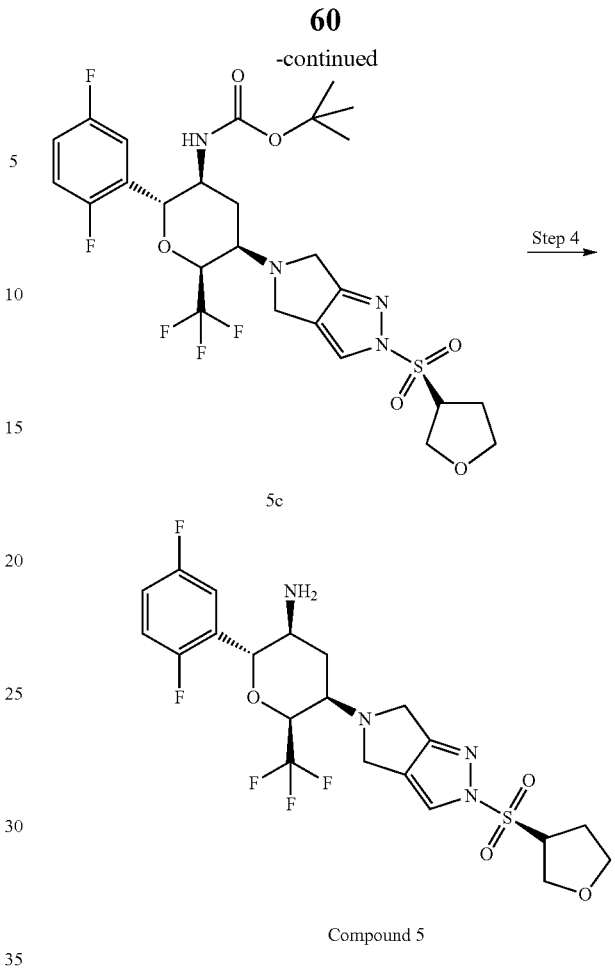

5c

Compound 5

Step 1: (R)-tert-butyl. 2-((tetrahydrofuran-3-yl)sulfonyl)-4,6-dihydropyrrolo[3,4-c]pyrazole-5(2H)-carboxylate (5a)

Under N$_2$ protection and a condition free of water and oxygen, Intermediate 2 (1000 mg, 4.78 mmol) was dissolved in N,N-dimethylformamide (15 ml), which was cooled to −15° C., and sodium bis(trimethylsilyl)amide (4.78 mL, 2 mol/L, 9.56 mmol) was added, followed by stirring for 30 min, and S-tetrahydrofuran-3-ylsulfonyl chloride (1.39 g, 8.13 mmol) was added dropwise to the reaction solution, followed by reaction for 16 hours at this temperature. The temperature was raised to 0° C., and the reaction was quenched by addition of water (20 ml) to the reaction solution, which was then extracted with ethyl acetate (20 ml×2). The organic phases were combined, dried over anhydrous sodium sulfate, concentrated, re-dissolved in. tetrahydrofuran (20 ml), and cooled to −10° C. to 0° C. Potassium t-butoxide (85 mg, 0.76 mmol) was added, and the reaction was allowed to proceed for 24 hours at this temperature. After the reaction was completed, a saturated aqueous solution of ammonium chloride (10 ml) and water (10 ml) were added. The solution was extracted with ethyl acetate (20 ml×3). The organic phases were combined, dried over anhydrous sodium sulfate, and concentrated. The residue was purified by silica gel column chromatography (petroleum ether/ethyl acetate (v/v)=5:1) to obtain a white solid 5a (810 mg, yield 62.3%).

Step 2: (R)-2-((tetrahydrofuran-3-yl)sulfonyl)-2,4,5,6-tetrahydropyrrolo[3,4-c]pyrazole (5b)

5a (400 mg, 1.17 mmol) was dissolved in a solution of hydrochloric acid in ethyl acetate (5 ml, 4 mol/l), followed by reaction at room temperature for 1 hour. After the reaction was complete, the system was allowed to settle and liquid was removed. Ethyl acetate was added, followed by stirring for 1 min. The system was allowed to settle, and liquid was removed. The residual solid was purified by column chromatography (dichloromethane/methanol (v/v)=20:1, plus a small amount of aqueous ammonia) to obtain a light yellow solid 5b (210 mg, yield 74%).

Step 3: tert-butyl ((2R,3S,5R,6S)-2-(2,5-difluorophenyl)-5-(2-(((R)-tetrahydrofuran-3-yl)sulfonyl)pyrrolo[3,4-c]pyrazol-5(2H,4H,6H)-yl)-6-(trifluoromethyl)tetrahydro-2H-pyran-3-yl)carbamate (5c)

Intermediate 1 (271 mg, 0.686 mmol) and 5b (200 mg, 0.823 mmol) were added to toluene (5 ml), and the reaction was allowed to proceed in an open round-bottom flask in a 140° C. oil bath until the solvent was evaporated to dryness. In a $N_2$ atmosphere, the residue was cooled to room temperature and dissolved in 1,2-dichloroethane (10 ml), and tri(acetoxy)sodium borohydride (580 mg, 2.744 mmol) and acetic acid (103 mg, 2.50 mmol) were added sequentially, followed by reaction at room temperature for 3 hours. The reaction was quenched by addition of a saturated sodium bicarbonate solution (15 ml) to the reaction solution, which was allowed to be partitioned. The aqueous phase was extracted with ethyl acetate (15 mL×3). The organic phases were combined, dried over anhydrous sodium sulfate, and concentrated. The concentrate was purified by silica gel column chromatography (petroleum ether/ethyl acetate (v/v)=5:1) to obtain a white foamy solid 5e (255 mg, yield 61%).

Step 4:
(2R,3S,5R,6S)-2-(2,5-difluorophenyl)-5-(2-(((R)-tetrahydrofuran-3-yl)sulfonyl)pyrrolo[3,4-c]pyrazol-5(2H,4H,6H)-yl)-6-(trifluoromethyl)tetrahydro-2H-pyran-3-amine (Compound 5)

5c (255 mg, 0.41 mmol) was dissolved in 6 ml dichloromethane and 2 ml trifluoroacetic acid, followed by stirring at room temperature for 1 hour. The reaction was quenched by addition of a saturated sodium bicarbonate solution (10 ml) to the reaction solution, which was allowed to be partitioned. The. aqueous phase was extracted with ethyl acetate (15 ml×2). The organic phases were combined, dried over anhydrous sodium sulfate, and concentrated. The concentrate was purified by silica gel column chromatography (dichloromethane/methanol (v/v)=50:1) to obtain Compound 5 as a white powdery solid (175 mg, yield 82%).

MS m/z (ESI):523.1[M+1];

$^1$H NMR (400 MHz, DMSO-$d_6$) δ 8.05 (s, 1H), 7.32-7.22 (m, 3H), 4.82-4.72 (m, 1H), 4.49 (m, 2H), 4.09 (ddd, 1H), 4.00-3.80 (m, 4H), 3.80-3.72 (m, 2H), 3.64 (dd, 1H), 3.49-3.42 (m, 1H), 3.00 (ddt, 1H), 2.36-2.28 (m, 1H), 2.23 (dt, 2H), 1.81 (dd, 1H).

EXAMPLE 6

(2R,3S,5R,6S)-5-2-(cyclopentylsulfonyl)pyrrolo[3,4-c]pyrazol-5(2H,4H,6H)-yl)-2-(2,5-difluorophenyl)-6-(trifluoromethyl)tetrahydro-2H-pyran-3-amine (Compound 6)

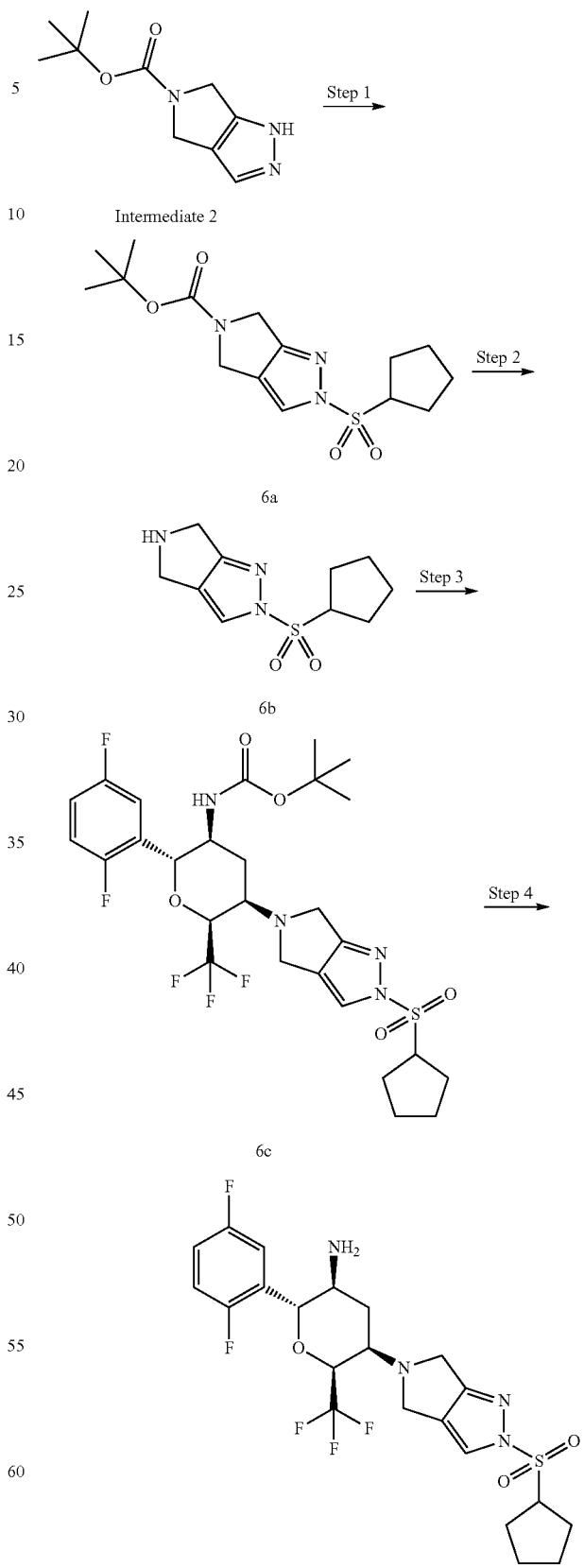

Step 1: tert-butyl 2-(cyclopentylsulfonyl)-4,6-dihydropyrrolo[3,4-c]pyrazole-5(2H)-carboxylate (6a)

Under $N_2$ protection and a condition free of water and oxygen, Intermediate 2 (1000 mg, 4.78 mmol) was dissolved in N,N-dimethylformamide (15 ml), which was cooled to −15° C., and sodium bis(trimethylsilyl)amide (4.78 mL, 2 mol/L, 9.56 mmol) was added, followed by stirring for 30 min, and S-cyclopentylsulfonyl chloride (1.37 g, 8.13 mmol) was added dropwise, followed by reaction for 16 hours at −15° C. The temperature was raised to 0° C., and the reaction was quenched by addition of water (20 ml) to the reaction. solution, which was then extracted with ethyl acetate (20 mL×2). The organic phases were combined, dried over anhydrous sodium sulfate concentrated, re-dissolved in tetrahydrofuran (20 ml), and cooled to a temperature between −10° C. and 0° C., potassium t-butoxide (85 mg, 0.76 mmol) was added, and the reaction was allowed to proceed for 24 hours at this temperature. After the reaction was completed, a saturated aqueous solution of ammonium chloride (10 ml) and water (10 ml) were added. The solution was extracted with ethyl acetate (20 mL×3). The. organic layers were combined, dried over anhydrous sodium sulfate, and concentrated. The residue was purified by silica gel column chromatography (petroleum ether/ethyl acetate (v/v)=5:1) to obtain a white solid 6a (800 mg, yield 62%).

Step 2: 2-(cyclopentylsulfonyl)-2,4,5,6-tetrahydropyrrolo [3,4-c]pyrazole (6b)

6a (430 mg, 1.26 mmol) was dissolved in a solution of hydrochloric acid in ethyl acetate (8 ml, 4 mol/l), followed by reaction at room temperature for 1 hour. After the reaction was complete, the system was allowed to settle and liquid was removed. Ethyl acetate was added, followed by stirring for 1 min. The system was allowed to settle, and liquid was removed. The residue was purified by column chromatography (dichloromethane/methanol (v/v)=20:1, plus a small amount of aqueous ammonia) to obtain a light yellow solid 6b (290 mg, yield 95%).

Step 3: tert-butyl ((2R,3S,5R,6S)-5-(2-(cyclopentylsulfonyl)pyrrolo[3,4-c]pyrazol-5(2H,4H,6H)-yl)-2-(2,5-difluorophenyl)-6-(trifluoromethyl)tetrahydro-2H-pyran-3-yl)carbamate (6c)

Intermediate 1 (327 mg, 0.828 mmol) and 6b (280 mg, 1.16 mmol) were added to toluene (8 ml), and the reaction was allowed to proceed in an open round-bottom flask in a 140° C. oil bath until the solvent was evaporated to dryness. In a $N_2$ atmosphere, the residue was cooled to room temperature and dissolved in 1,2-dichloroethane (10 ml), and tri(acetoxy)sodium borohydride (700 mg, 3.31 mmol) and acetic acid (0.1 ml, 1.82 mmol) were added sequentially, followed by reaction at room temperature for 3 hours. The reaction was quenched by addition of a saturated sodium bicarbonate solution (15 ml) to the reaction solution, which was allowed to be partitioned. The aqueous phase was extracted with ethyl acetate (15 mL×3). The organic phases were combined, dried over anhydrous sodium sulfate, and concentrated. The concentrate was purified by silica gel column chromatography (petroleum ether/ethyl acetate (v/v)=5:1) to obtain a white foamy solid 6e (210 mg, yield 41%).

Step 4: (2R,3S,5R,6S)-5-(2-(cyclopentylsulfonyl)pyrrolo[3,4-c]pyrazol-5(2H,4H,6H)-yl)-2-(2,5-difluorophenyl)-6-(trifluoromethyl)tetrahydro-2H-pyran-3-amine (Compound 6)

6c (210 mg, 0.34 mmol) was dissolved in dichloromethane (6 ml) and trifluoroacetic acid (2 ml), followed by stirring at room temperature for 1 hour. The reaction was quenched by addition of a saturated sodium bicarbonate solution (10 ml) to the reaction solution, which was allowed to be partitioned. The aqueous phase was extracted with ethyl acetate (15 mL×2). The organic phases were combined, dried over anhydrous sodium sulfate, and concentrated. The concentrate was purified by silica gel column chromatography (dichloromethane/methanol (v/v)=50:1) to obtain Compound 6 as a white powdery solid (105 mg, yield 60%).

MS m/z (ESI):521.1[M+1];

$^1$HNMR (400 MHz, DMSO-$d_6$) δ 8.00 (m, 1H), 7.31-7.19 (m, 3H), 4.81-4.70 (qd, 1H), 4.50 (d, 1H), 4.09 (m, 1H), 4.00-3.89 (m, 2H), 3.84-3.73 (m, 2H), 3.50-3.40 (m, 1H), 3.00 (td, 1H), 2.37-2.27 (m, 1H), 1.96-1.85 (m, 4H), 1.85-1.75 (m, 1H), 1.63-1.56 (m, 4H).

Figure 10:
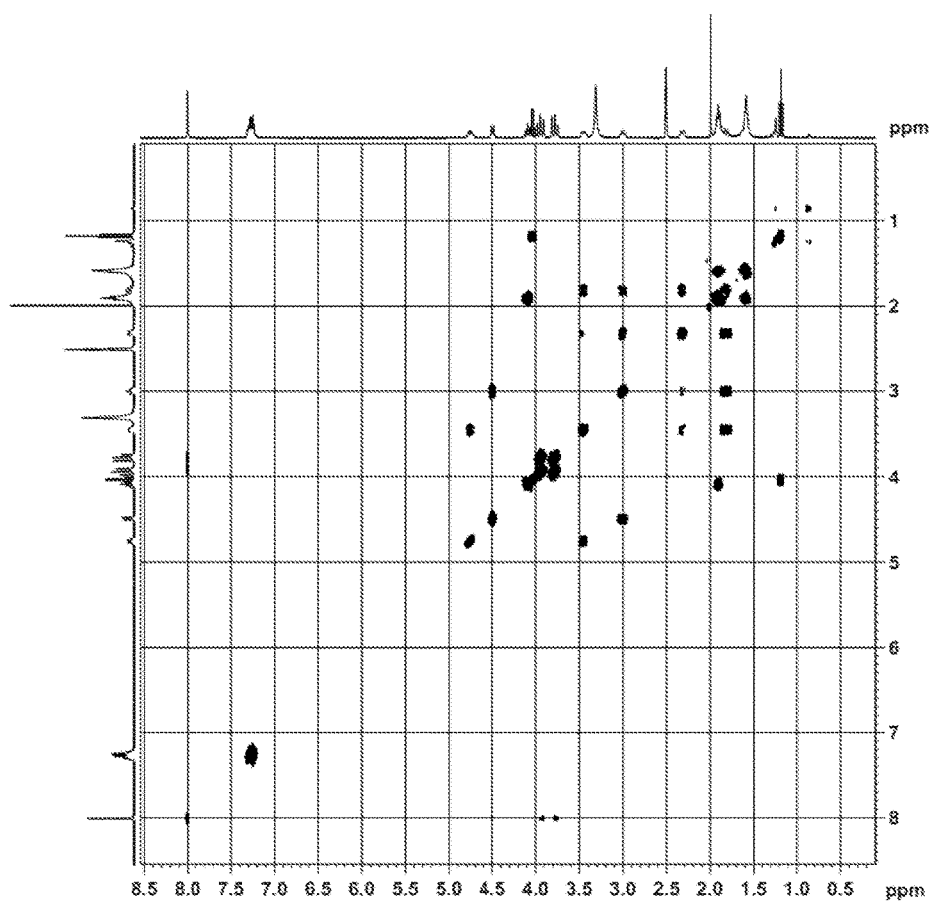
FIG. 10 is the $^1$H-$^1$H COSY spectrum of Compound 6.
Figure 11:
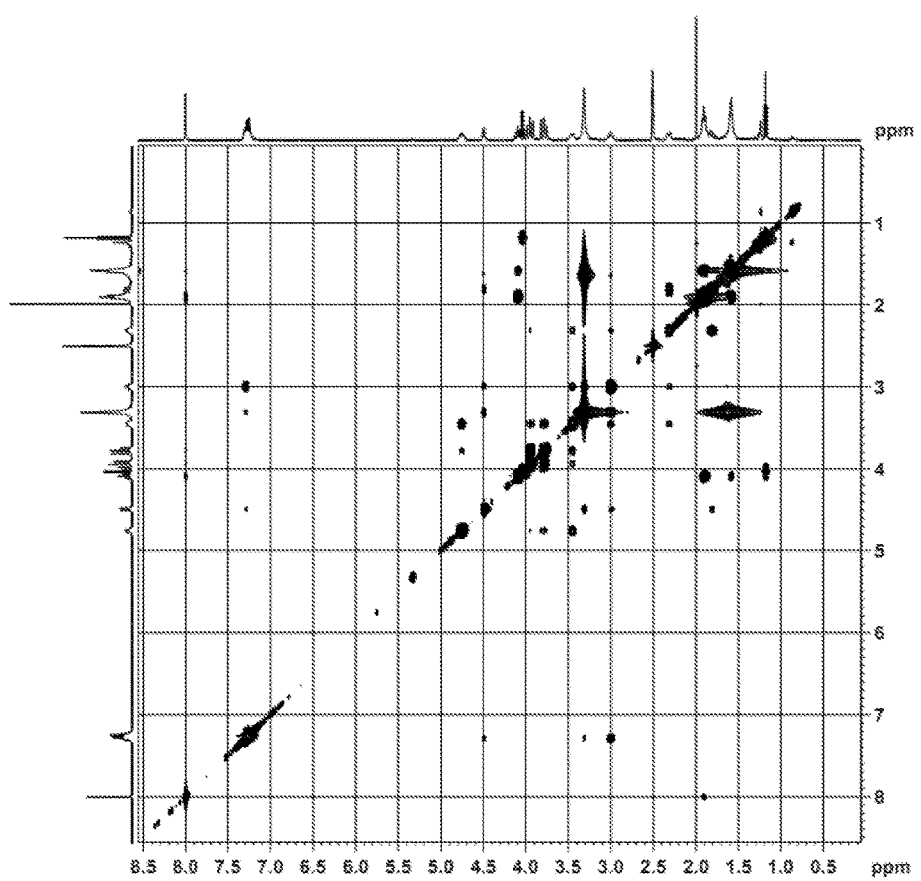
FIG. 11 is the $^1$H-$^1$H NOESY spectrum of Compound 6.
Figure 12:
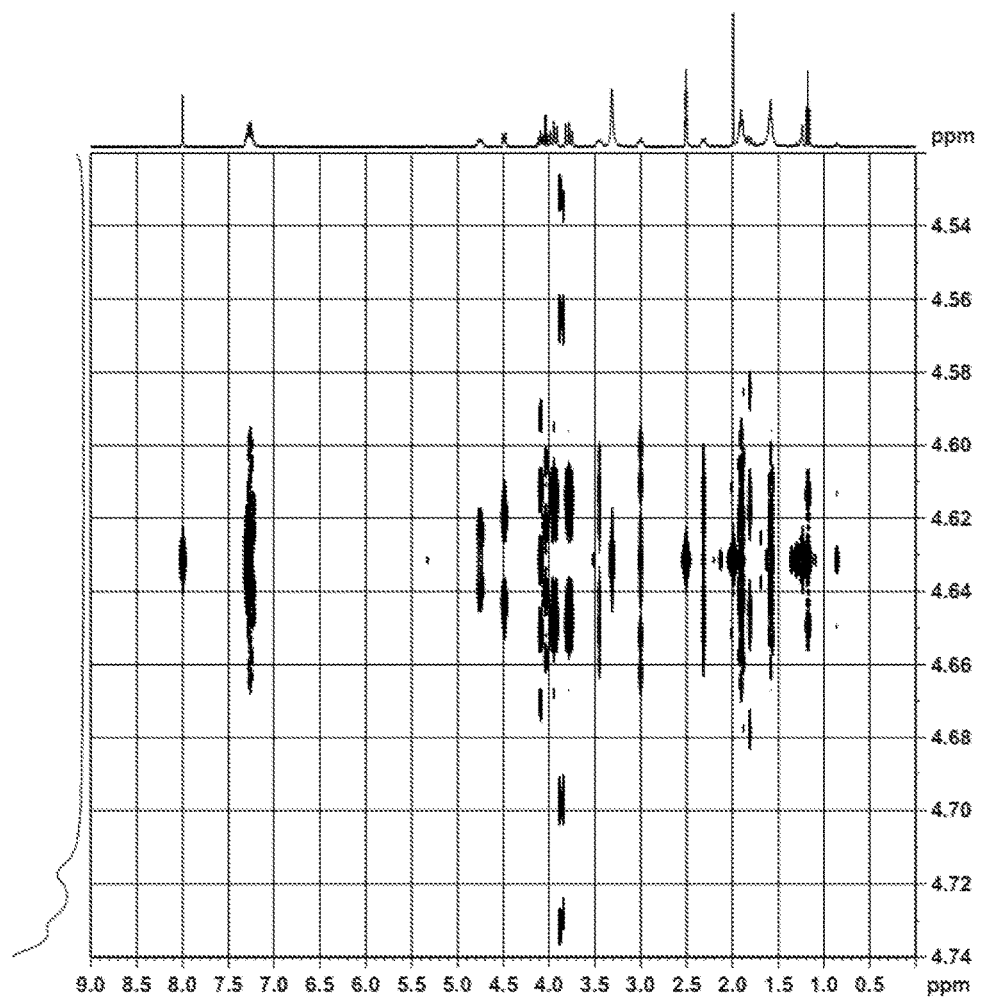
FIG. 12 is the $^1$H-$^1$H J-resolved spectrum of Compound 6.

The $^1$H-$^1$H COSY, $^1$H-$^1$H NOESY and $^1$H-$^1$H J-resolved spectra of Compound 6 are shown in FIGS. 10-12, and the data are shown in Table 4, demonstrating that Compound 6 has the following concentration:

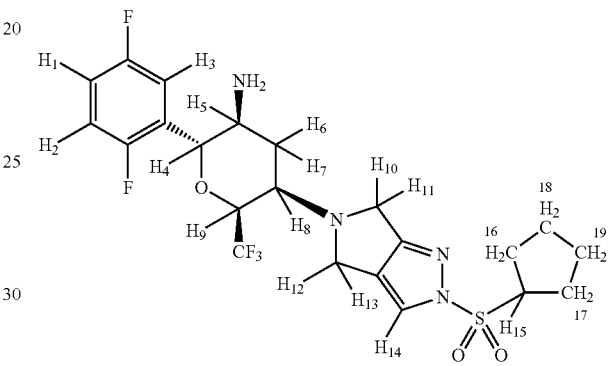

TABLE 4

Data of the $^1$H NMR, $^1$H-$^1$H COSY, and $^1$H-$^1$H NOESY of Compound 6 (DMSO-$d_6$, 400 MHz)

| | Shift | Multiplet | COSY | NOESY |
|---|---|---|---|---|
| H1, H2, H3 | 7.27 | m | — | H4, H5, NH2** |
| H4 | 4.50 | d(9.68 Hz*) | H5, H9 | H3, H7, NH2** |
| H5 | 3.00 | ddd(12.71, 9.68, 4.26 Hz*) | H4, H6, H7 | H3, H8 |
| H6 | 2.32 | m | H5, H7, H8 | — |
| H7 | 1.82 | m | H5, H, 6, H8 | H4 |
| H8 | 3.46 | m | H6, H7, H9 | H5, H10, H11 H12, H13 |
| H9 | 4.76 | qd(5.73 Hz*) | H4, H8 | H10, H11 H12, H13 |
| H10, H11 H12, H13 | 3.87 | m | H10, H11 H12, H13, H14 | H8, H9 |
| H14 | 8.00 | m | H10, H11 H12, H13 | H15, 16-CH$_2$ 17-CH$_2$ |
| H15 | 4.09 | m | 16-CH$_2$, 17-CH$_2$ | 18-CH$_2$, 19-CH$_2$ |
| 16-CH$_2$, 17-CH$_2$ | 1.90 | m | H15, 18-CH2 19-CH2 | H14 |
| 18-CH$_2$, 19-CH$_2$ | 1.60 | m | 16-CH2 17-CH2 | H15 |

*Read from $^1$H-$^1$H J-resolved spectra.
**NH$_2$ proton exchanged with the water peak.

EXAMPLE 7

(2R,3S,5S,6R)-2-(2,5-difluorophenyl)-5-(2-(methylsulfonyl)pyrrolo[3,4-c]pyrazol-5(2H, 4H,6H)-yl)-6-(trifluoromethyl)tetrahydro-2H-pyran-3-amine (Compound 7)

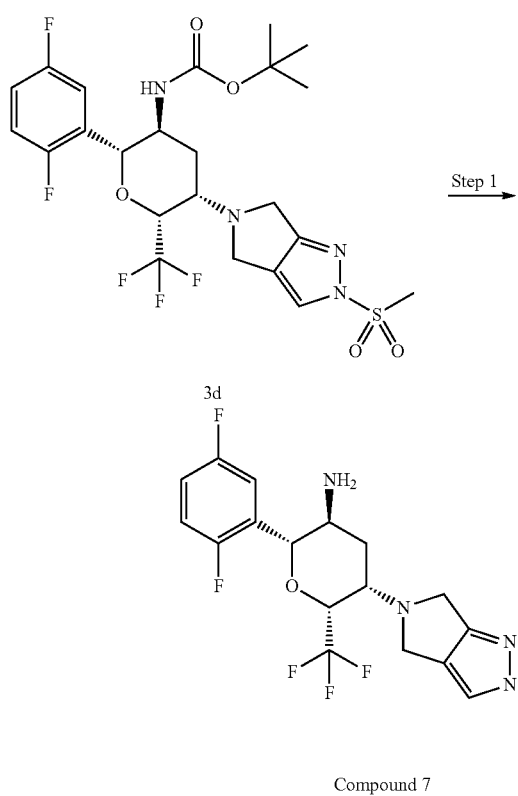

Step 1:
(2R,3S,5S,6R)-2-(2.5-fluorophenyl)-5-(2-(methylsulfonyl)pyrrolo[3,4-c]pyrazol-5(2H, 4H,6H)-yl)-6-(trifluoromethyl)tetrahydro-2H-pyran-3-amine (Compound 7)

3d (400 mg, 0.7 mmol) was dissolved in dichloromethane (6 ml) and trifluoroacetic acid (2 ml), followed by stirring at room temperature for 1 hour. The reaction was quenched by addition of a saturated sodium bicarbonate solution (30 ml) to the reaction solution, which was allowed to be partitioned. The aqueous phase was extracted with ethyl acetate (30 mL×2). The organic phases were combined, dried over anhydrous sodium sulfate, and concentrated. The concentrate was purified by silica gel column chromatography (dichloromethane/methanol (v/v)=30:1) to obtain Compound 7 as a white powdery solid (200 mg, yield 61%).

MS m/z (ESI):467.0[M+1];

NMR (400 MHz, DMSO-$d_6$): δ 7.94 (s, 1H), 7.39-7.06 (m, 3H), 4.52-4.41 (m, 2H), 4.07 (s, 2H), 4.01 (s, 2H), 3.49 (m, 4H), 3.28 (d, 1H), 2.48 (d, 1H), 1.75 (ddd, 1H), 1.38 (s, 2H).

Biological Tests

1. Evaluation of Pharmacokinetics in Rats

Male SD rats (purchased from Vital River Laboratory Animal Technology Co. LTD. License No. 11400700005540) each weighing 200 to 240 g were fasted overnight. On the day of experiments, 3 SD rats were each intragastrically administered with 5 mg/kg compound, and a 0.20 ml blood sample was taken from their jugular veins before the administration and 15 min, 30 min, 45 min, 1 h, 2 h, 4 h, 8 h, 12 h, and 24 h after the administration, to an EDTA tube. Acetonitrile containing an internal reference (verapamil 5.00 ng/ml, and glibenclamide 50.0 ng/ml) was added to the blood sample, followed by vigorous vortexing and centrifuging at 13,000 rpm for 10 min. The supernatant was taken for the LC-MS/MS assay. Pharmacokinetics parameters were calculated by using the non-compartment mode in Pharsight Phoenix 6.3. The experimental results are shown in Table 5.

TABLE 5

Results of pharmacokinetics evaluation in rats.

| Compound | Blood drug level Cmax (ng/mL) | AUC $AUC_{0-t}$ (ng · h · mL$^{-1}$) | Half-life $T_{1/2}$ (h) |
|---|---|---|---|
| Omarigliptin | 9292 | 66829 | 6.1 |
| Compound 3 | 11567 | 106470 | 7.1 |

Conclusion: compared with the positive control (Omarigliptin), the compound of the present invention showed a higher maximum concentration and an exposure amount, a longer half life, and a smaller clearance.

2. Oral Glucose Tolerance Test

The oral glucose tolerance test (OGTT) was performed to evaluate the hypoglycemic effect of the compounds of the present invention in mice. 8-week old male C57 mice were purchased from Beijing Vital River Laboratory Animal Technology Co., Ltd. (Laboratory Animal Certificate No. SCXK (Beijing) 2012-0001) and used in the test The mice were grouped based on the base level of blood sugar after fasted, with 10 animals per group. The test compounds were formulated into a 1 mg/ml suspension and administered intragastrically at a dose of 10 mg/kg, while a blank agent was administered to the blank control group. 60 min after the administration, a 50% aqueous solution of glucose was dosed (5 g/kg), and the blood sugar level of each mouse was measured with a OneTouch blood glucose meter manufactured by Johnson & Johnson at 0 min, 15 min, 30 min, 45 min, 60 min, and 120 min. The decrease (%) in area under the drug-time curve (AUC) was calculated, and the experimental results are shown in Table 6.

TABLE 6

Evaluation results of OGTT in mice.

| No. | Compound | Decrease in AUC (%) |
|---|---|---|
| 1 | Omarigliptin | 22.27 |
| 2 | Compound 1 | 27.20 |
| 3 | Compound 3 | 27.99 |

Conclusion: the compounds of the present invention showed a significant hypoglycemic effect in that they can significantly reduce the blood sugar level in mice after a single oral administration.

Figure 13:
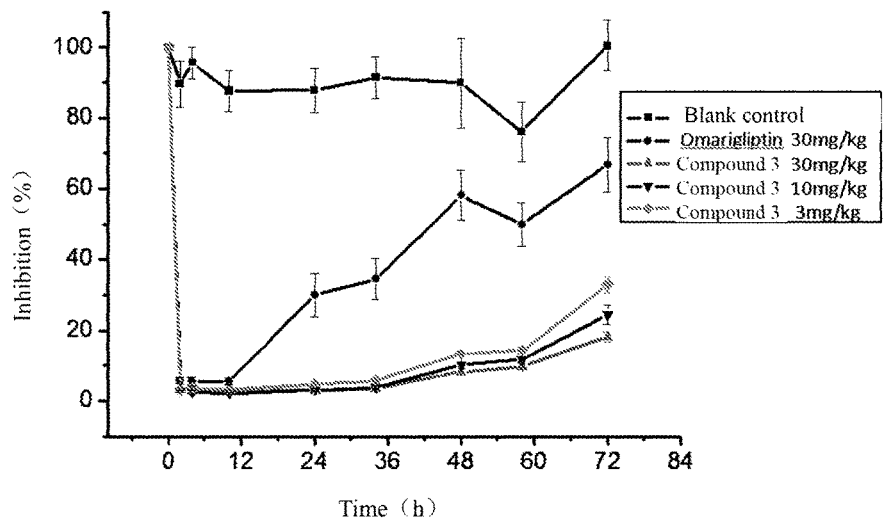
FIG. 13 shows the effect of a single oral administration on the DPP4 activity in ob/ob mice.

3. Effect of Single Oral Administration on the Enzymatic Activity of DPP-IV in Ob/Ob Mice The test compounds were formulated into solutions of 0.3 mg/ml, 1.0 mg/ml or 3.0 mg/ml with 0.5% CMC-Na. ob/ob mice from Shanghai Institute of Materia Medica were fasted for 16 hours in advance with free access to water, and were grouped into 5 groups based on the body weight on the next day. The test group was administered with the compounds at various doses, while the blank group was given a blank solvent at 10 ml/kg. Blood samples were taken from the orbit of the mice at 0 h, 2 h, 4 h, 10 h, 24 h, 34 h, 48 h, 58 h and 72 h. After EDTA-2Na anticoagulation, 40 μl plasma was taken and 10 μl AFC (0.2 mM) substrate was added thereto, followed by reaction at room temperature for 15 min. The enzymatic activity of DPP4 in the plasma was measured with a microplate reader, and the experimental results are shown in Table 7 and FIG. 13.

TABLE 7

Results of the enzymatic activity of DPP-IV in ob/ob mice after single oral administration.

| Compound | DPP-IV enzymatic activity | | | | | | | | |
|---|---|---|---|---|---|---|---|---|---|
| | 0 h | 2 h | 4 h | 10 h | 24 h | 34 h | 48 h | 58 h | 72 h |
| Blank group | 100% | 89.6% | 95.6% | 87.5% | 87.7% | 91.3% | 89.8% | 76.0% | 100.4% |
| Omarigliptin 30 mg/kg | 100% | 5.8% | 5.4% | 5.5% | 30.0% | 34.5% | 58.1% | 49.9% | 66.7% |
| Compound 3 30 mg/kg | 100% | 3.2% | 3.0% | 2.7% | 3.0% | 3.5% | 8.2% | 9.7% | 18.2% |
| Compound 3 10 mg/kg | 100% | 2.8% | 2.5% | 2.2% | 3.1% | 3.8% | 10.1% | 11.8% | 24.4% |
| Compound 3 3 mg/kg | 100% | 2.9% | 3.5% | 3.2% | 4.7% | 5.7% | 13.4% | 14.3% | 32.9% |

Conclusion: after a single oral administration to ob/ob mice, Compound 3 showed a more significant inhibitory effect on the enzymatic activity of DPP-IV than the positive control Omarigliptin; at: the same dose, Compound 3 showed a period of 80% inhibition of DPP-IV activity that is over 3 times longer than that of the positive control Omarigliptin; when the dose of Compound 3 was only ⅒ of that of the positive control Omarigliptin, Compound 3 still showed a more significant inhibitory effect on DPP-IV activity, exhibiting the potential of a longer acting period.

4. Enzymatic Screening Experiment on Plasma DPP-IV in Rats

The laboratory animals were 8-week old male SD rats purchased from Beijing Vital River Laboratory Animal Technology Co., Ltd. (Laboratory Animal Certificate No. SCXK (Beijing) 2012-0001). Fasted rats were grouped based on the body weight. Blood samples were taken from the orbit of the rats and subjected to anticoagulation with EDTA-2Na. The test group was orally administrated with the test compounds at a dose of 3.0 mg/kg, while the control group was orally administrated with a blank agent. Blood samples were taken at various time points after the administration, and centrifuged at 2,500 rpm for 15 min. Plasma was taken and preserved at −20° C. For the enzymatic activity assay, 40 μl plasma was taken from each test sample, and 10 μl H-Ala-Pro-AFC substrate (0.2 mM) was added thereto, followed by reaction for 15 min. The reaction was read with a microplate reader (Wavelength of excitation=405 nm, Wavelength of emission=535 nM), followed by statistic analysis with Origin 7.5. The period during which the inhibition of plasma DPP-IV enzymatic activity was ≥70% was calculated for the test compounds, and the results are shown in Table 8.

TABLE 8

Results of enzymatic screening experiment on plasma DPP-IV in rats.

| No. | Compound | Duration of Inhibition ≥70% (h) |
|---|---|---|
| 1 | Omarigliptin | 55 |
| 2 | Compound 1 | 55 |
| 3 | Compound 4 | >72 |

Conclusion: the compounds of the present invention can significantly inhibit the enzymatic activity of plasma DPP-IV in rats; and in particular, the period during which the inhibition of plasma DPP-IV activity by Compound 4 was ≥70% was significantly longer than that of the control compound.

5. Enzymatic Screening Experiment on Plasma DPP-IV in Dogs

The laboratory animals were male beagle dogs provided by Chengdu Dashuo Biological Sciences and Technology Co., Ltd. Fasted beagle dogs were grouped based on the body weight. The test group was orally administrated with the test compounds at a dose of 10.0 mg/kg. Blood samples were taken at various time points after the administration and subjected to anticoagulation with EDTA-2Na. Blood samples were centrifuged at 2,500 rpm for 15 min. Plasma was taken and preserved at −20° C. For the enzymatic activity assay, 40 μl plasma was taken from each test sample, and 10 μl H-Ala-Pro-AFC substrate (0.2 mM) was added thereto, followed by reaction for 15 nm. The reaction was read with a microplate reader (Wavelength of excitation=405 nm, Wavelength of emission=535 nM), followed by statistic analysis with Origin 7.5. The period during which the inhibition of plasma DPP-IV enzymatic activity was ≥80% was calculated for the test compounds, and the results are shown in Table 9.

TABLE 9

Results of enzymatic screening experiment on plasma DPP-IV in beagle dogs.

| No. | Compound | Duration of Inhibition ≥80% (h) |
|---|---|---|
| 1 | Omarigliptin | 162 |
| 2 | Compound 4 | 192 |

Conclusion: the compounds of the present invention showed a period of inhibition of plasma DPP-IV enzymatic activity in beagle dogs significantly longer than that of the control compound, exhibiting a higher potential of a long-acting effect.

6. Enzymatic Screening Experiment on Plasma DPP-IV in Monkeys

Figure 14:
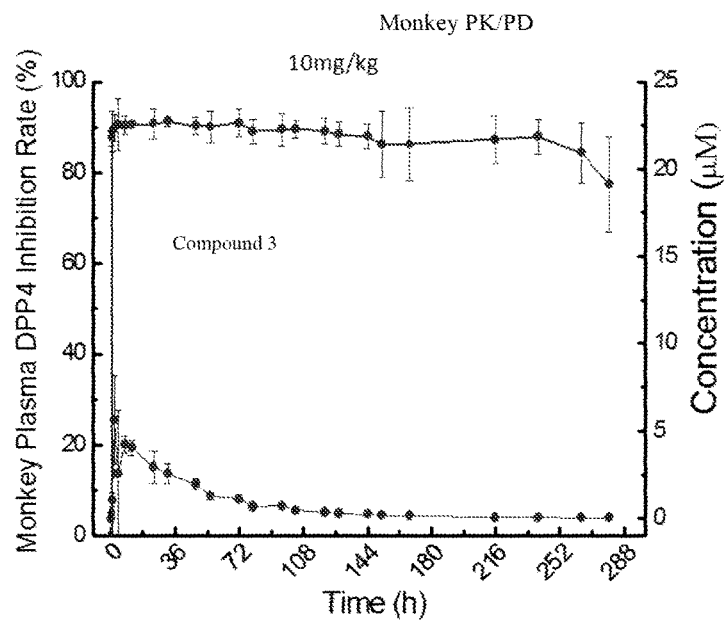
FIG. 14 is a curve chart showing the results of an enzymatic screening experiment on monkey blood plasma DPP-IV with Compound 3.

The laboratory animals were healthy male Rhesus monkeys each weighing about 5 kg, provided by Sichuan Primed Bio-tech Group Co. Ltd. Fasted Rhesus monkeys were grouped based on the body weight. The test group was orally administrated with the test compounds at a dose of 10.0 mg/kg. Blood samples were taken at various time points after the administration and subjected to anticoagulation with EDTA-2Na. Blood samples were centrifuged at 2,500 rpm for 15 min. Plasma was taken and preserved at −20° C. For the enzymatic activity assay, 40 µl plasma was taken from each test sample, and 10 µl H-Ala-Pro-AFC substrate (0.2 mM) was added thereto, followed by reaction for 15 min. The reaction was read with a microplate reader (Wavelength of excitation=405 nm, Wavelength of emission=535 nM), followed by statistic analysis with Origin 7.5. The period during which the inhibition of plasma. DPP-IV enzymatic activity was ≥80% was calculated for the test compounds, and the concentration of the compounds in plasma was measured by LC-MS/MS. The results are shown in FIG. 14 and Table 10 below.

TABLE 10

Results of enzymatic screening experiment on plasma DPP-IV in monkeys.

| | Compound 3 | | | Compound 3 | |
| --- | --- | --- | --- | --- | --- |
| Duration (h) | Inhibition (%) | Concentration (µM) | Duration (h) | Inhibition (%) | Concentration (µM) |
| 0 | 0 | 0 | 80 | 89.04 | 0.68 |
| 0.5 | 87.65 | 0.27 | 96 | 89.48 | 0.71 |
| 1 | 88.94 | 1.06 | 104 | 89.54 | 0.44 |
| 2 | 89.70 | 5.64 | 120 | 89.06 | 0.34 |
| 4 | 90.57 | 2.56 | 128 | 88.51 | 0.27 |
| 8 | 90.40 | 4.22 | 144 | 87.96 | 0.21 |
| 12 | 90.53 | 4.01 | 152 | 86.13 | 0.16 |
| 24 | 90.71 | 2.93 | 168 | 86.23 | 0.14 |
| 32 | 91.25 | 2.56 | 216 | 87.28 | 0.071 |
| 48 | 90.27 | 1.94 | 240 | 87.93 | 0.041 |
| 56 | 90.03 | 1.28 | 264 | 84.38 | 0.032 |
| 72 | 90.88 | 1.12 | — | — | — |

Conclusion: after a single oral administration, the compounds of the present invention can inhibit the enzymatic activity of plasma DPP-IV in monkeys for as long as 11 days or more, exhibiting an excellent potential of a long-acting effect.

What is claimed is:

1. An amino pyran ring derivative represented by general formula (I) or a stereoisomer, a pharmaceutically acceptable salt or a prodrug thereof:

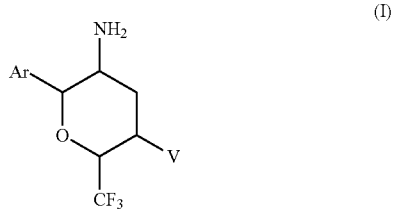

(I)

wherein
V is selected from the following groups:

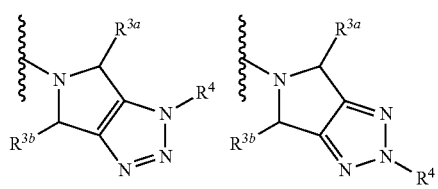

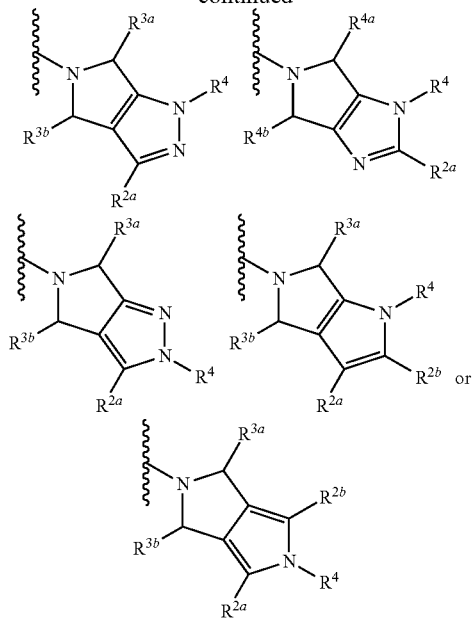

Ar is a phenyl substituted with 0 to 5 $R^1$;

$R^1$ is selected from H, F, Cl, Br, I, hydroxyl, cyano, $C_{1-8}$ alkyl, $C_{1-8}$ alkoxy, $C_{2-8}$ alkenyl, $C_{2-8}$ alkynyl, —$(CH_2)_m$—$C_{3-15}$ cycloalkyl, —$(CH_2)_m$—(3- to 15-membered heterocycloalkyl), —$(CH_2)_m$—$C_{6-10}$ aryl, —$(CH_2)_m$—(6- to 10-membered heteroaryl), —$(CH_2)_m$—C(=O)—$R^5$, —$(CH_2)_m$—$NR^6R^7$, —$(CH_2)_m$—C(=O)—$NR^6R^7$, —$(CH_2)_m$—O—C(=O)—$NR^6R^7$, —$(CH_2)_m$—S(=O)$_n$—$R^8$, —$(CH_2)_m$—$NR^9$—S(=O)$_n$—$R^8$, —$(CH_2)_m$—$NR^9$—C(=O)—$NR^6R^7$ or —$(CH_2)_m$—$NR^9$—C(=O)—$R^5$, wherein the alkyl, alkoxy, alkenyl, alkynyl, cycloalkyl, heterocycloalkyl, aryl or heteroaryl is optionally further substituted with 0 to 5 substituents selected from F, Cl, Br, I, —$CH_2F$, —$CHF_2$, —$CF_3$, hydroxyl, $C_{1-4}$ alkyl or $C_{1-4}$ alkoxy, the heterocycloalkyl or heteroaryl has 1 to 5 atoms or groups selected from N, O or S(=O)$_n$;

$R^{2a}$ and $R^{2b}$ are each independently selected from H, F, Cl, Br, I, hydroxyl, cyano, $C_{1-8}$ alkyl, $C_{1-8}$ alkoxy, $C_{2-8}$ alkenyl, $C_{2-8}$ alkynyl, —$(CH_2)_m$—$C_{3-15}$ cycloalkyl, —$(CH_2)_m$—(3- to 15-membered heterocycloalkyl), —$(CH_2)_m$—$C_{6-10}$ aryl, —$(CH_2)_m$—(6- to 10-membered heteroaryl), —$(CH_2)_m$—C(=O)—$R^5$, —$(CH_2)_m$—$NR^6R^7$, —$(CH_2)_m$—C(=O)—$NR^6R^7$, —$(CH_2)_m$—O—C(=O)—$NR^6R^7$, —$(CH_2)_n$—$R^8$, —$(CH_2)_m$—$NR^9$—S(=O)$_n$—$R^8$, —$(CH_2)_m$—$NR^9$—C(=O)—$NR^6R^7$ or —$(CH_2)_m$—$NR^9$—C(=O)—$R^5$, wherein the alkyl, alkoxy, alkenyl, alkynyl, cycloalkyl, heterocycloalkyl, aryl or heteroaryl is optionally further substituted with 0 to 3 substituents selected from F, Cl, Br, I, —$CH_2F$, —$CHF_2$, —$CF_3$, hydroxyl, $C_{1-4}$ alkyl or $C_{1-4}$ alkoxy, and the heterocycloalkyl or heteroaryl has 1 to 5 atoms or groups selected from N, O or S(=O)$_n$;

$R^{3a}$ and $R^{3b}$ are each independently selected from H, F, Cl, Br, I, hydroxyl, cyano or $C_{1-8}$ alkyl, wherein the alkyl is optionally further substituted with 0 to 5 substituents selected from F, Cl, Br, I, —$CH_2F$, —$CHF_2$, —$CF_3$, hydroxyl, $C_{1-4}$ alkyl or $C_{1-4}$ alkoxy;

$R^{4a}$ and $R^{4b}$ are each independently selected from H, F, Cl, Br, I, hydroxyl, cyano or $C_{1-8}$ alkyl, wherein the alkyl is optionally further substituted with 0 to 5 substituents selected from F, Cl, Br, I, —CH$_2$F, —CHF$_2$, —CF$_3$, hydroxyl, C$_{1-4}$ alkyl or C$_{1-4}$ alkoxy, and R$^{4a}$ and R$^{4b}$ are not at the same time H;

R$^4$ is selected from H, cyano, C$_{1-8}$ alkyl, C$_{1-8}$ alkoxy, C$_{2-8}$ alkenyl, C$_{2-8}$ alkynyl, —(CH$_2$)$_m$—C$_{3-15}$ cycloalkyl, —(CH$_2$)$_m$—(3- to 15-membered heterocycloalkyl), —(CH$_2$)$_m$—C$_{6-10}$ aryl, —(CH$_2$)$_m$-(6- to 10-membered heteroaryl), —(CH$_2$)$_m$—C(=O)—R$^5$, —(CH$_2$)$_m$—NR$^6$R$^7$, —(CH$_2$)$_m$—C(=O)—NR$^6$R$^7$, —(CH$_2$)$_m$—O—C(=O)—NR$^6$R$^7$, —(CH$_2$)$_m$—S(=O)$_n$—R$^8$, —(CH$_2$)$_m$—NR$^9$—S(=O)$_n$—R$^8$, —(CH$_2$)$_m$—NR$^9$—C(=O)—NR$^6$R$^7$ or —(CH$_2$)$_m$—NR$^9$—C(=O)—R$^5$, wherein the alkyl, alkoxy, alkenyl, alkynyl, cycloalkyl, heterocycloalkyl, aryl or heteroaryl is optionally further substituted with 0 to 3 substituents selected from F, Cl, Br, I, —CH$_2$F, —CHF$_2$, —CF$_3$, hydroxyl, C$_{1-4}$ alkyl or C$_{1-4}$ alkoxy, and the heterocycloalkyl or heteroaryl has 1 to 5 atoms or groups selected from N, O or S(=O)$_n$;

R$^5$ is selected from hydroxyl, C$_{1-8}$ alkyl, C$_{1-8}$ alkoxy, C$_{3-15}$ cycloalkyl, C$_{6-10}$ aryl, 6- to 10-membered heteroaryl, —O—C$_{3-15}$ cycloalkyl, —O—C$_{6-10}$ aryl or —O-(6- to 10-membered heteroaryl);

R$^6$, R$^7$ and R$^9$ are each independently selected from H, C$_{1-8}$ alkyl, C$_{3-15}$ cycloalkyl, C$_{6-10}$ aryl, 6- to 10-membered heteroaryl or 3- to 15-membered heterocycloalkyl;

R$^8$ is selected from C$_{1-8}$ alkyl, C$_{3-15}$ cycloalkyl, C$_{6-10}$ aryl, 6- to 10-membered heteroaryl or 3- to 15-membered heterocycloalkyl; wherein the alkyl, cycloalkyl, heterocycloalkyl, aryl or heteroaryl is optionally further substituted with 0 to 5 fluorine atoms, and the heterocycloalkyl or heteroaryl has 1 to 5 atoms or groups selected from N, O or S(=O)$_n$;

m is selected from 0, 1 or 2; and n is selected from 0, 1 or 2.

2. The amino pyran ring derivative represented by general formula (I) according to claim 1, or a stereoisomer, a pharmaceutically acceptable salt or a prodrug thereof, wherein R$^1$ is selected from H or F;

R$^{2a}$ and R$^{2b}$ are each independently selected from H, C$_{1-6}$ alkyl, C$_{3-6}$ cycloalkyl or 3- to 8-membered heterocycloalkyl, wherein the alkyl, cycloalkyl or heterocycloalkyl is optionally further substituted with 0 to 3 substituents selected from F, Cl, Br, I, —CH$_2$F, —CHF$_2$, —CF$_3$, hydroxyl, C$_{1-4}$ alkyl or C$_{1-4}$ alkoxy, and the heterocycloalkyl has 1 to 3 atoms or groups selected from N, O or S(=O)$_2$;

R$^{3a}$ and R$^{3b}$ are each independently selected from H or C$_{1-2}$ alkyl, wherein the alkyl is optionally further substituted with 0 to 3 substituents selected from F, hydroxyl or C$_{1-4}$ alkoxy;

R$^4$ is selected from H or —S(=O)$_2$—R$^8$;

R$^8$ is selected from C$_{1-6}$ alkyl, C$_{3-6}$ cycloalkyl, C$_{6-10}$ aryl, 6- to 10-membered heteroaryl or 3- to 8-membered heterocycloalkyl; wherein the alkyl, cycloalkyl, heterocycloalkyl, aryl or heteroaryl is optionally further substituted with 0 to 5 fluorine atoms, the heterocycloalkyl or heteroaryl has 1 to 5 atoms or groups selected from N, O or S(=O)$_2$.

3. The amino pyran ring derivative represented by general formula (I) according to claim 2, or a stereoisomer, a pharmaceutically acceptable salt or a prodrug thereof, wherein V is selected from:

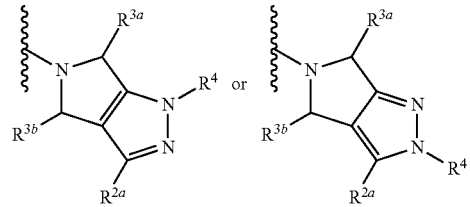

Ar is selected from 2,5-difluorophenyl or 2,4,5-trifluorophenyl;

R$^{2a}$ is selected from H, C$_{1-6}$ alkyl, or C$_{3-6}$ cycloalkyl, wherein the alkyl or cycloalkyl is optionally further substituted with 0 to 3 substituents selected from F, hydroxyl, C$_{1-4}$ alkyl or C$_{1-4}$ alkoxy;

R$^{1a}$ and R$^{1b}$ are each independently selected from H or C$_{1-2}$ alkyl, wherein the alkyl is optionally further substituted with 0 to 3 substituents selected from F, hydroxyl or C$_{1-4}$ alkoxy;

R$^4$ is —S(=O)$_2$—R$^8$;

R$^8$ is selected from C$_{1-2}$ alkyl, 3- to 6-membered heterocycloalkyl, or C$_{3-6}$ cycloalkyl;

wherein the alkyl, heterocycloalkyl, or cycloalkyl is optionally further substituted with 0 to 5 fluorine atoms, and the heterocycloalkyl has 1 to 3 atoms or groups selected from N, O or S(=O)$_2$.

4. The amino pyran ring derivative represented by general formula (I) according to claim 3, or a stereoisomer, a pharmaceutically acceptable salt or a prodrug thereof, wherein V is

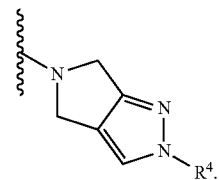

5. The amino pyran ring derivative represented by general formula (I) according to claim 4, or a stereoisomer, a pharmaceutically acceptable salt or a prodrug thereof, wherein R$^4$ is —S(=O)$_2$—R$^8$;

R$^8$ is selected from C$_{1-2}$ alkyl, 4- to 6-membered heterocycloalkyl , or C3-6 cycloalkyl;

wherein the alkyl, heterocycloalkyl , or cycloalkyl is optionally further substituted with 0 to 5 fluorine atoms, and the heterocycloalkyl has 1 to 3 atoms or groups selected from N, O or S(=O)$_2$.

6. The amino pyran ring derivative represented by general formula (I) according to claim 5, or a stereoisomer, a pharmaceutically acceptable salt or a prodrug thereof, wherein R$^8$ is selected from methyl, ethyl,

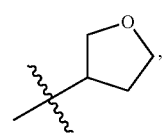

cyclopropyl, cyclobutyl, or cyclopentyl.

7. The amino pyran ring derivative represented by general formula (I) according to claim 1, or a stereoisomer, a pharmaceutically acceptable salt or a prodrug thereof, wherein the amino pyran ring derivative is selected from:

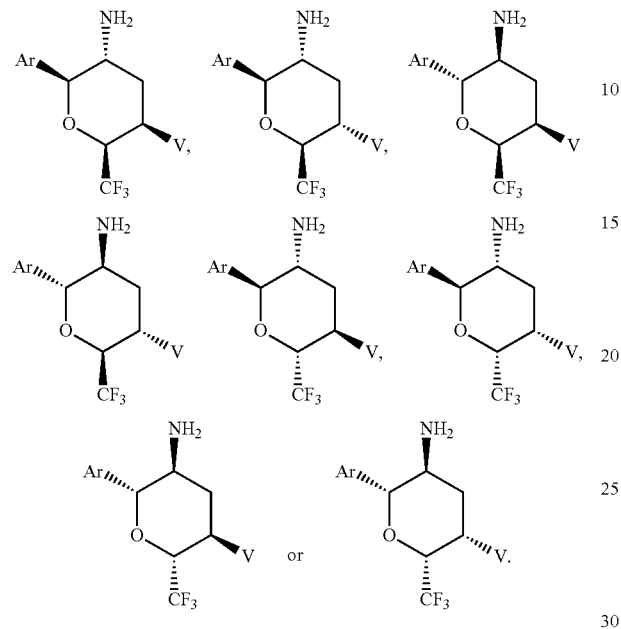

8. The amino pyran ring derivative represented by general formula (I) according to claim 7, or a stereoisomer, a pharmaceutically acceptable salt or a prodrug thereof, wherein the amino pyran ring derivative is selected from:

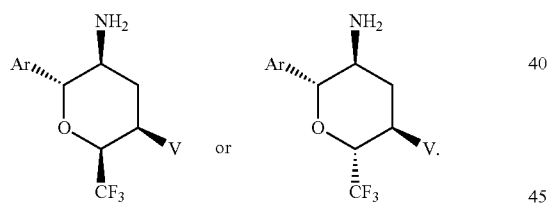

9. The amino pyran ring derivative represented by general formula (I) according to claim 8, or a stereoisomer, a pharmaceutically acceptable salt or a prodrug thereof, wherein the amino pyran ring derivative is selected from:

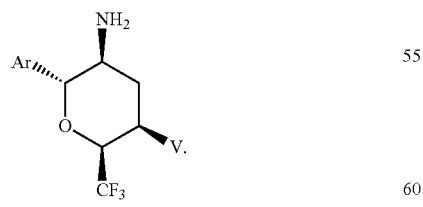

10. The amino pyran ring derivative represented by general formula (I) according to claim 1, or a stereoisomer, a pharmaceutically acceptable salt or a prodrug thereof, wherein the amino pyran ring derivative is selected from:

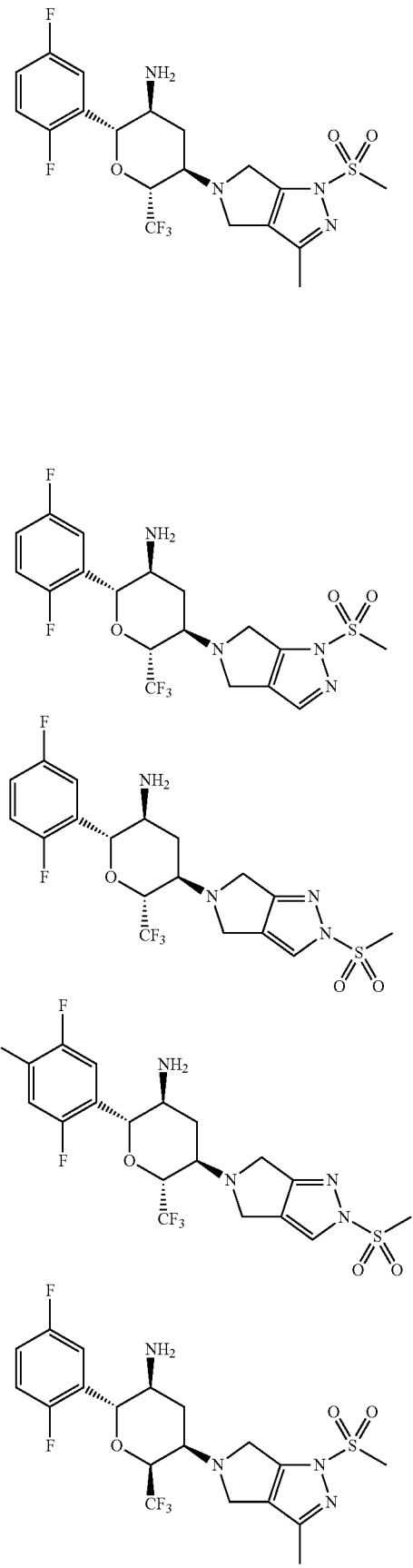

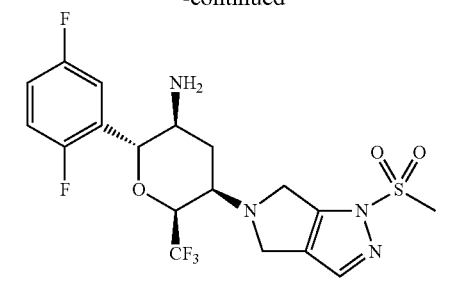
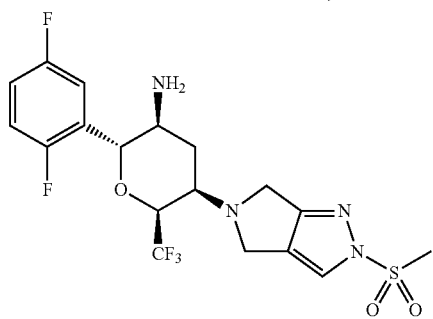
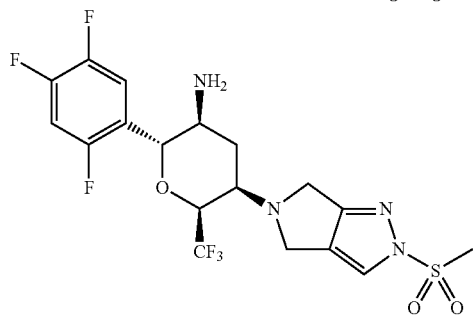
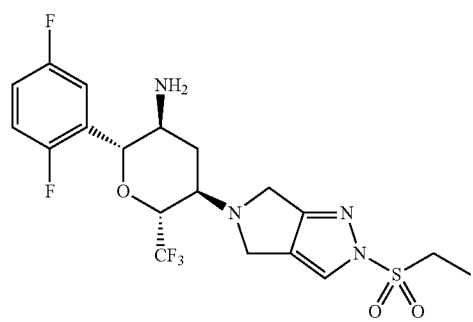
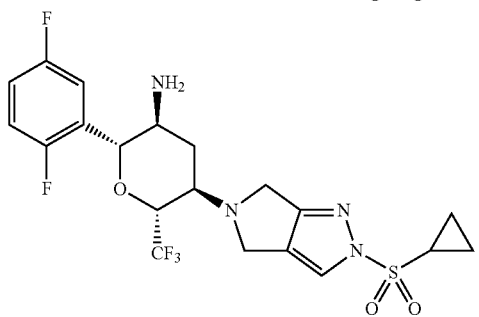
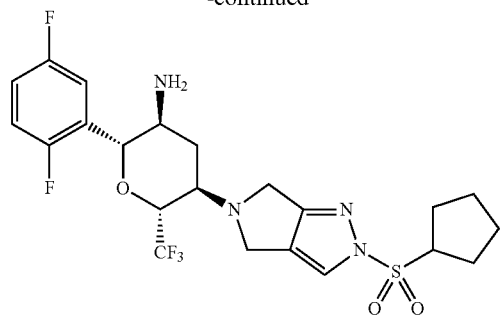
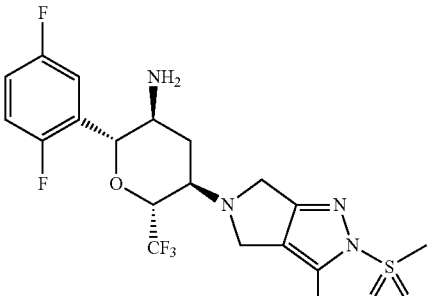
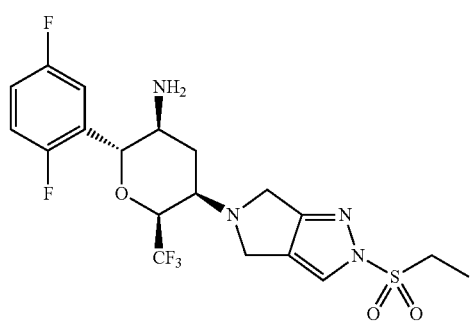
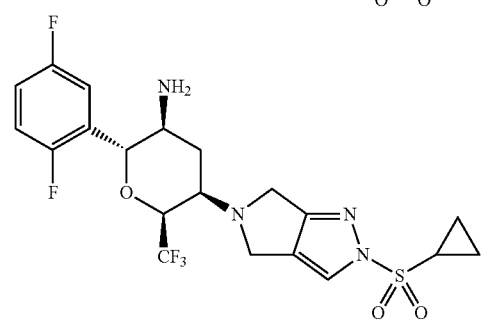
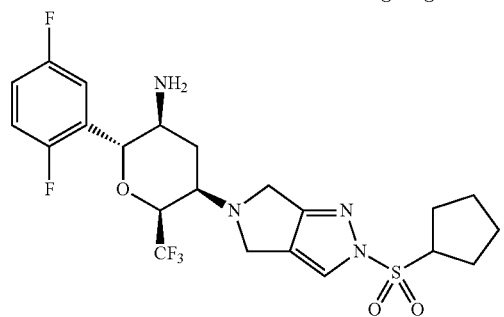

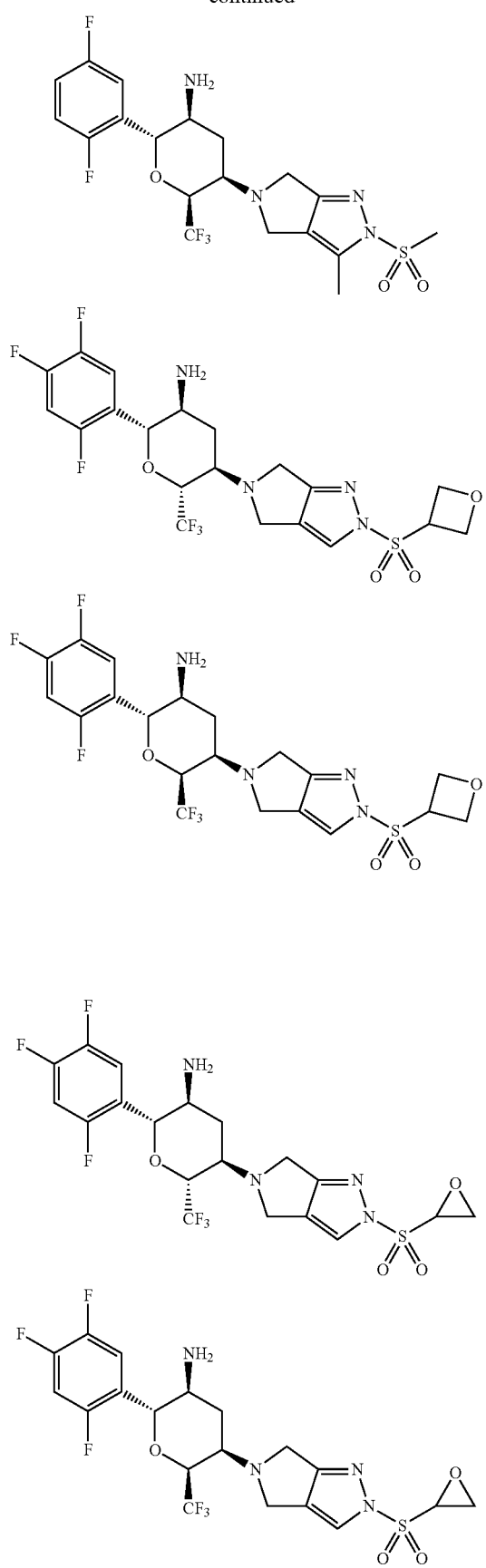
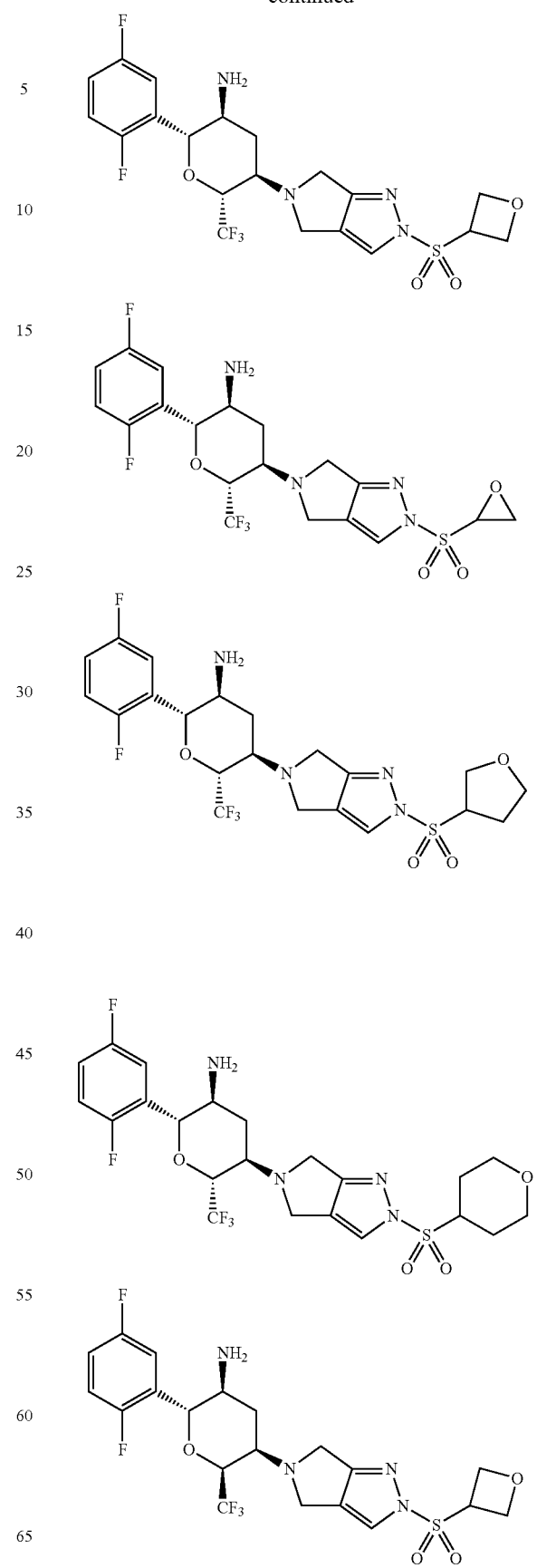

79
-continued
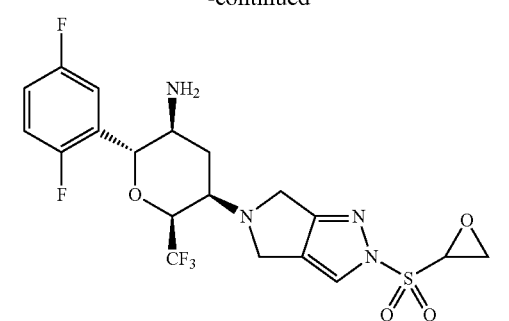
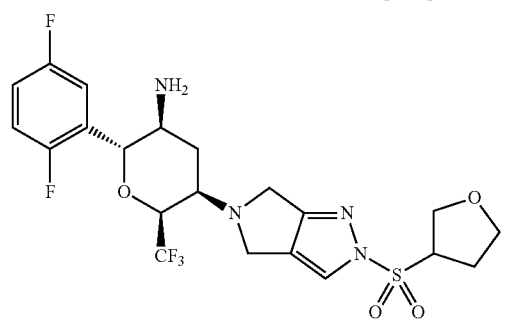
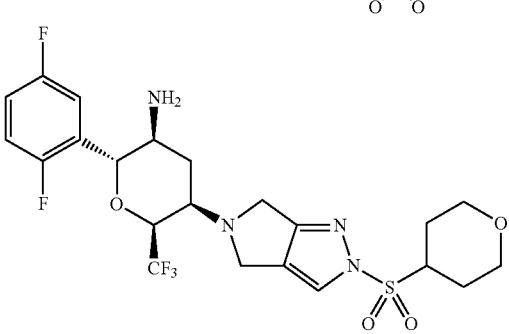
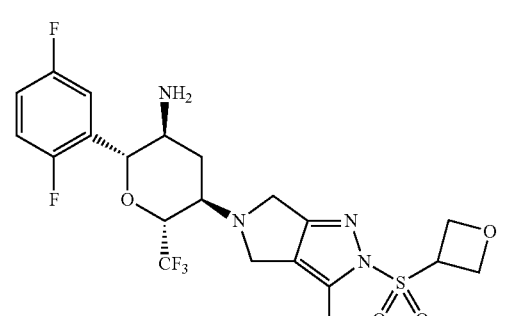
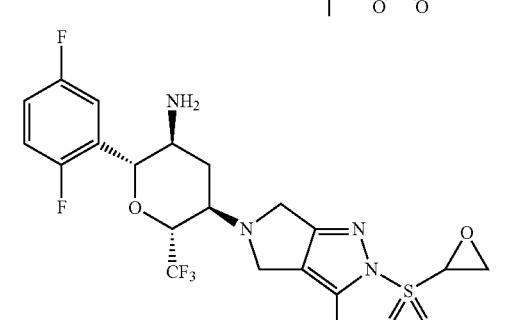
80
-continued
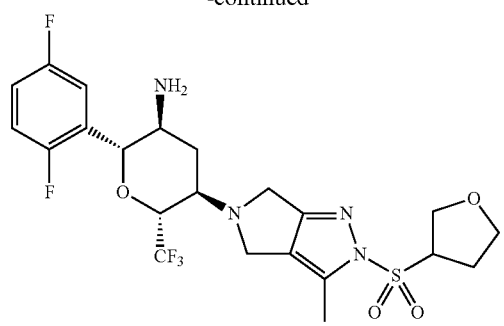
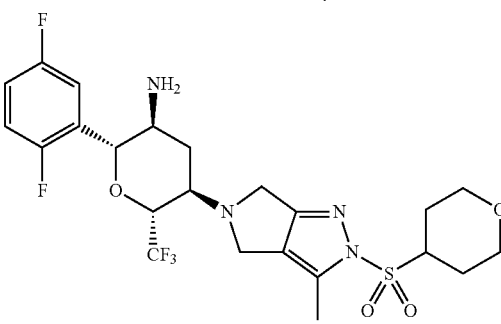
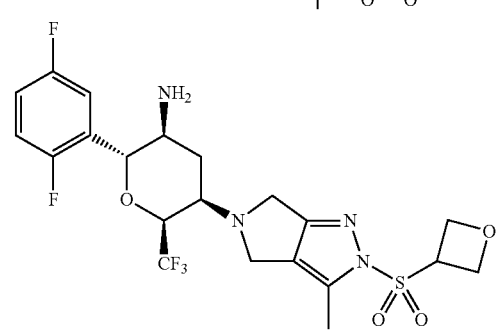
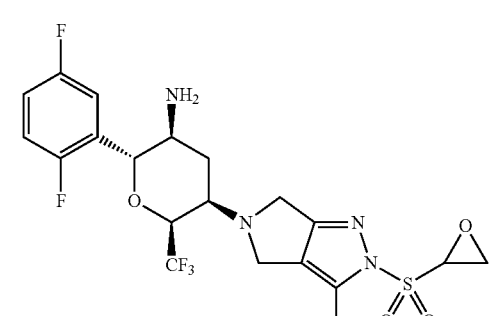
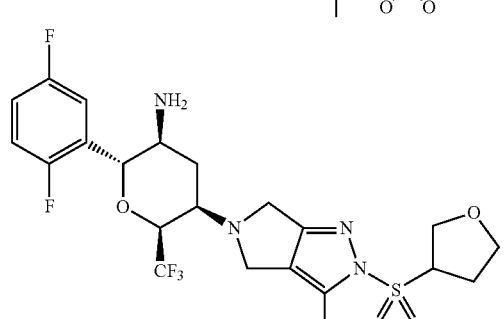

-continued

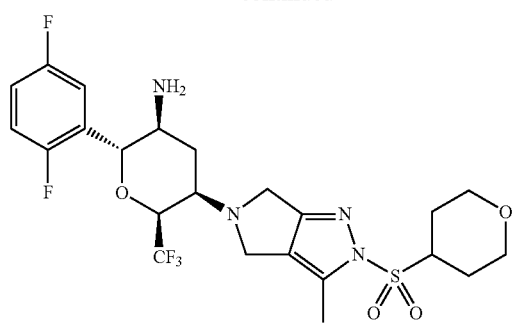

or

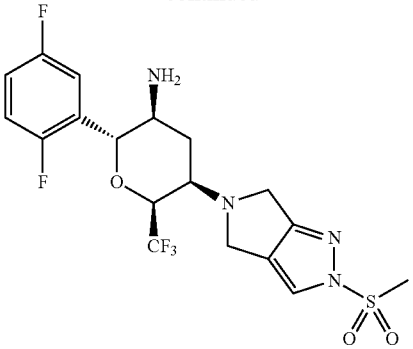

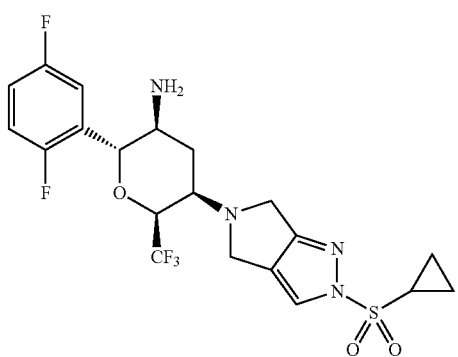

11. The amino pyran ring derivative represented by general formula (I) according to claim 10, or a stereoisomer, a pharmaceutically acceptable salt or a prodrug thereof, wherein the amino pyran ring derivative is selected from:

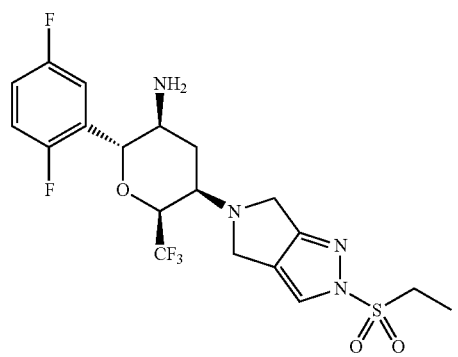

or

12. A pharmaceutical composition, comprising: an effective amount of the amino pyran ring derivative represented by general formula (I) according to claim 1 or a stereoisomer, a pharmaceutically acceptable salt or a prodrug thereof; and a pharmaceutically acceptable carrier or excipient.

13. Use of the amino pyran ring derivative represented by general formula (I) according to claim 1 or a stereoisomer, a pharmaceutically acceptable salt or a prodrug thereof, or a pharmaceutical composition comprising: an effective amount of the amino pyran ring derivative represented by general formula (I) according to claim 1 or a stereoisomer, a pharmaceutically acceptable salt or a prodrug thereof; and a pharmaceutically acceptable carrier or excipient, in the manufacture of a di-peptidyl peptidase IV inhibitor.

14. The use according to claim 13, wherein the di-peptidyl peptidase IV inhibitor is used to manufacture a medicament for treating a metabolic disease, wherein the metabolic disease includes diabetes, diabetic retinopathy, diabetic neuropathy, diabetic nephropathy, insulin resistance, hyperglycemia, hyperinsulinism, elevated levels of fatty acids or glycerol, hyperlipidemia, obesity, hypertriglyceridemia, X-syndrome, diabetic complications, atherosclerosis, or hypertension.

15. The use according to claim 14, wherein the diabetes is type II diabetes.

16. A method for treating a metabolic disease, comprising: administering an amino pyran ring derivative represented by general formula (I) according to claim 1 or a stereoisomer, a pharmaceutically acceptable salt, or a prodrug thereof; or a pharmaceutical composition comprising: an effective amount of the amino pyran ring derivative represented by general formula (I) according to claim 1 or a stereoisomer, a pharmaceutically acceptable salt or a prodrug thereof; and a pharmaceutically acceptable carrier or excipient.

17. The method according to claim 16, wherein the metabolic disease includes diabetes, diabetic retinopathy, diabetic neuropathy, diabetic nephropathy, insulin resistance, hyperglycemia, hyperinsulinism, elevated levels of fatty acids or glycerol, hyperlipidemia, obesity, hypertriglyceridemia, X-syndrome, diabetic complications, atherosclerosis, or hypertension.

18. The method according to claim 17, wherein the diabetes is type II diabetes.

* * * * *